United States Patent
Turner et al.

(10) Patent No.: US 7,387,896 B2
(45) Date of Patent: Jun. 17, 2008

(54) MICRORNA VECTORS

(75) Inventors: David Loyd Turner, Ann Arbor, MI (US); Kwan-Ho Chung, Ann Arbor, MI (US); Paresh D. Patel, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 9 days.

(21) Appl. No.: 11/158,201

(22) Filed: Jun. 21, 2005

(65) Prior Publication Data

US 2006/0063174 A1    Mar. 23, 2006

Related U.S. Application Data

(63) Continuation-in-part of application No. 10/397,943, filed on Mar. 26, 2003, now abandoned.

(60) Provisional application No. 60/581,504, filed on Jun. 21, 2004.

(51) Int. Cl.
  *C12N 15/63* (2006.01)
  *C12N 15/11* (2006.01)
(52) U.S. Cl. .................... 435/455; 435/320.1
(58) Field of Classification Search ................ None
  See application file for complete search history.

(56) References Cited

U.S. PATENT DOCUMENTS 6,471,957 B1  10/2002  Sim et al.
2002/0198362 A1  12/2002  Gaiger et al.

OTHER PUBLICATIONS

Zweiger, Transducing the Genome, 2001, McGraw-Hill, New York, p. 237.*
Molecular Biology Reagents/Protocols 1992, United States Biochemical Corporation, 1991, Cleveland, Ohio, p. 317.*
Nykanen, A. et al. ATP requirements and small interfering RNA structure in the RNA interference pathway. (2001) Cell 107, 309-21.
Elbashir, S. M. et al. Functional anatomy of siRNAs for mediating efficient RNAi in Drosophila melanogaster embryo lysate. (2001) Embo J 20, 6877-88.
Elbashir, S. M. et al. Duplexes of 21-nucleotide RNAs mediate RNA interference in cultured mammalian cells. (2001) Nature 411, 494-8.
Reddy, R. Transcription of a U6 small nuclear RNA gene in vitro. Transcription of a mouse U6 small nuclear RNA gene in vitro by RNA polymerase III is dependent on transcription factor(s) different from transcription factors IIIA, IIIB, and IIIC(1988) J Biol Chem 263, 15980-4).
Davis, R. L. et al. Molecular targets of vertebrate segmentation: two mechanisms control segmental expression of Xenopus hairy2 during somite (2001) Dev Cell 1, 553-65).
Rupp, R. A. et al. Xenopus embryos regulate the nuclear localization of XMyoD (1994) Genes Dev 8, 1311-1323).
Turner, D. L. & Weintraub, H. Expression of achaete-scute homolog 3 in Xenopus embryos converts ectodermal cells to a neural fate (1994) Genes Dev 8, 1434-1447.
Zeng et al., Both natural and designed micro RNAs can inhibit the expression of cognate mRNAs when expressed in human cells.; Molecular Cell 9:1327-1333 (2002).
Lipardi, C. et al. RNAi as random degradative PCR: siRNA primers convert mRNA into dsRNAs that are degraded to generate new siRNAs. (2001) Cell 107, 297-307).
Elbashir, S. M. et al. RNA interference is mediated by 21- and 22-nucleotide RNAs (2001) Genes Dev 15, 188-200.
Tam et al., bic, a novel gene activated by proviral insertions in avian leukosis virus-induced lymphomas, is likely to function; Mol. Cell. Biol. 17:1490 [1997].
Tam, Identification and characterization of human BIC, a gene on chromosome 21 that encodes a noncoding RNA.; Gene 274:157 [2001].
Lagos-Quintana et al., Identification of tissue-specific microRNAs from mouse.; Curr Biol. 12:735 [2002].
Tam et al., Avian bic, a Gene Isolated from a Common Retroviral Site in Avian Leukosis Virus-Induced Lymphomas That Encodes a Noncoding RNA, Cooperates with c-myc in Lymphomagenesis and Erythroleukemogenesis; J. Virol 76:4275 [2002].
Figueroa et al., Akt2 Negatively Regulates Assembly of the POSH-MLK-JNK Signaling Complex; J. Biol. Chem. 278:47922 [2003].
Tapon et al., A new rac target POSH is an SH3-containing scaffold protein involved in the JNK and NF-kappaB signalling pathways.; EMBO J. 17:1395 [1998].

* cited by examiner

*Primary Examiner*—James Martinell
(74) *Attorney, Agent, or Firm*—Casimir Jones, S.C.

(57) ABSTRACT

The present invention relates to gene silencing, and in particular to compositions of microRNA sequences and vectors and to methods of synthesizing such in vitro and in vivo, and to methods of using such to regulate gene expression.

16 Claims, 19 Drawing Sheets

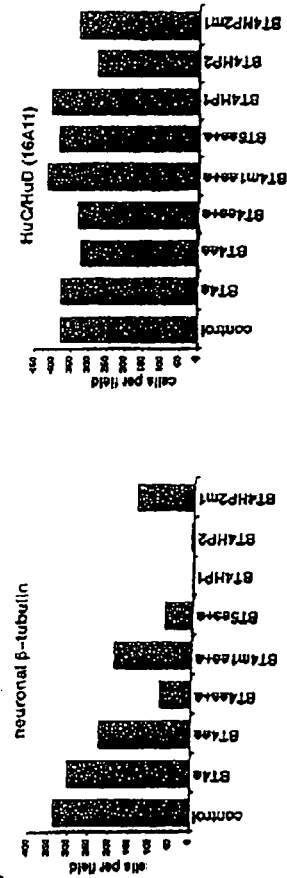

Figure 5A

T7pro20
GGTAATACGACTCACTATAG    SEQ ID NO: 95

T7BT4S
AAGACAGAGCCAAGTGACTCTATAGTGAGTCGTATTACC    SEQ ID NO: 107

T7BT4AS
GTGAGTCCACTGGCTCTGTCTATAGTGAGTCGTATTACC    SEQ ID NO: 108

FIGURE 5B-1

T7GFP5S
AAGAAGAAGTCGTGCTGCTTCTATAGTGAGTCGTATTACC    SEQ ID NO: 96

T7GFP5AS
ATGAAGCAGCACGACTTCTTCTATAGTGAGTCGTATTACC    SEQ ID NO: 97

T7GFP5m1S
AAGAAGAAGTCCAGCTGCTTCTATAGTGAGTCGTATTACC    SEQ ID NO: 98

T7GFP5m1AS
ATGAAGCAGCTGGACTTCTTCTATAGTGAGTCGTATTACC    SEQ ID NO: 99

T7GFP2S
AAGACCATGTGATCGCGTTCTATAGTGAGTCGTATTACC    SEQ ID NO: 100

T7GFP2AS
GAGAAGCGCGATCACATGGTCTATAGTGAGTCGTATTACC    SEQ ID NO: 101

T7GFP5HP1
AAGAAGAAGTCGTGCTGCTTCCATGAAGCAGCACGACTTCTTCTATAGTGAGTCGTATTA    SEQ ID NO: 102

T7GFP5HP1S
ATGAAGCAGCACGACTTCTTCTTGAAGAAGTCGTGCTGCTTCTATAGTGAGTCGTATTA    SEQ ID NO: 103

T7GFP5HP1m1
AAGAAGAAGTCCAGCTGCTTCCATGAAGCAGCTGGACTTCTTCTATAGTGAGTCGTATTA    SEQ ID NO: 104

T7GFP5HP1m2
AAGAAGAAGTCGTGCTGCTTCCATGAAGCAGCTCGACTTCTTCTATAGTGAGTCGTATTA    SEQ ID NO: 105

T7GFP5HP1m3
AAGAAGAAGTCCTGCTGCTTCCATGAAGCAGCAGACTCTTCTATAGTGAGTCGTATTA    SEQ ID NO: 106

FIGURE 5B-2

T7BT4m1s
AAGACAGAGCCTAGTGAGTCGACTCTATAGTGAGTCGTATTACC    SEQ ID NO: 109

T7BT4m1a
GTGAGTCCACTACGCCTCTGTCTATAGTGAGTCGTATTACC    SEQ ID NO: 110

T7BT4HP1
AAGACAGAGCCAAGTGGACTCTGTGAGTCCACTTGGCTCTGTCTATAGTGAGTCGTATTACC    SEQ ID NO: 111

T7BT4HP1m1
AAGACAGAGCCTAGTGGACTCTGTGAGTCCACTACGCCTCTGTCTATAGTGAGTCGTATTACC    SEQ ID NO: 112

FIGURE 5C-1

U6-BT4s
TTTGAGTCCACTTGGCTCTGTCTTTTT    SEQ ID NO: 113
    TCAGGTGAACCGAGACAGAAAAAGATC    SEQ ID NO: 114

U6-BT4as
TTTGACAGAGCCAAGTGGACTCTTTTT    SEQ ID NO: 115
    TGTCTCGGTTCACCTGAGAAAAAGATC    SEQ ID NO: 116

U6-BT4m1s
TTTGAGTCCACTTCCCTCTGTCTTTTT    SEQ ID NO: 117
    TCAGGTGAAGGGAGACAGAAAAAGATC    SEQ ID NO: 118

U6-BT4m1as
TTTGACAGAGGGAAGTGGACTCTTTTT    SEQ ID NO: 119
    TGTCTCCCTTCACCTGAGAAAAAGATC    SEQ ID NO: 120

U6-BT5as
TTTGGACTTTAACCTGGAGCCTTTTT    SEQ ID NO: 121
    CTGAAATTGGACCCTCGGAAAAAGATC    SEQ ID NO: 122

TTTGGCTCCCAGGTTAAAGTCCTTTT  SEQ ID NO: 123
CGAGGGTCCAATTTCAGGAAAAAGATC  SEQ ID NO: 124

U6-BT4HP1

TTTGACAGAGCCAAGTGGACTCACAGAGTCCACTTGGCTCTGTCTTTT  SEQ ID NO: 125
TGTCTCGGTTCACCTGAGTGTCTCAGGTGAACCGAGACAGAAAAGATC  SEQ ID NO: 126

U6-BT4HP2

TTTGACAGAGCCAAGTGGACTCACAGAGTCCACTTCGCTCTGTCTTTT  SEQ ID NO: 127
TGTCTCGGTTCACCTGAGTGTCTCAGGTGAAGCGAGACAGAAAAGATC  SEQ ID NO: 128

U6-BT4HP2m1

TTTGACAGAGCGTAGTGGACTCACAGAGTCCACTAGGCTCTGTCTTTT  SEQ ID NO: 129
TGTCTCGGATCACCTGAGTGTCTCAGGTGATCCGAGACAGAAAAGATC  SEQ ID NO: 130

```
U6-GSK3αHP1                                                U6-GSK3βHP1
5'      GUGGAUGUAGGCCAAGCUCC                        5'       GAUCUGGAGCUCUCGGUUCU
        ||||||||||||||||||| G                                |||||||||||||||||||| U
3' uuuuCACCUACAUCCGGUUCGAGG                         3' uuuuCUAGACCUCGAGAGCCAAGA
```

SEQ ID NO: 145                                    SEQ ID NO: 146

B

```
U6-GSK3αHP2                                                U6-GSK3βHP2
5'      GAUGGUUGGAUGACAGUUCA                       5'       GUGUUGCUGAGUGGCAGUCA
        |||||||||||||||||||| C                               |||||||||||||||||||| A
3' uuuuCUACCAACCUACCUGUCAAGU                        3' uuuuCACAACGACGACUCGUGAGG
```

SEQ ID NO: 147                                    SEQ ID NO: 148

```
U6-GSK3αβHP
5'      GUAGUACCGAGAGCGAGAUGU
        ||||||||||||||||||||| A
3' uuuuCAUCAUGGCUCUCGCUCUACU
```

SEQ ID NO: 149

C

```
GSK3α mRNA      5'...CCUACAUCUGCUCUCGGUACUACC...3'       SEQ ID NO: 150
                      |||||||||||||||||||||||
U6-GSK3αβHPas   3'  UAUGUAGACGAGAGCCAUGAUG  5'           SEQ ID NO: 151
                      ||||||||| |||||||||||
GSK3β mRNA      5'...CAUAUAUCUGUUCUCGGUACUACA...3'       SEQ ID NO: 152
```

FIG. 11

A. Primers for amplifying 471nt of mouse BIC exon 3 mBIC-F1 (forward)

SEQ ID NO: 153      5' GGGATCCGTGGTTAAGTTGCATATCCCT 3' mBIC-R1 (reverse)

SEQ ID NO: 154      5' GGTCTAGAGTGCATTCATTTTGTATTCTGG 3'

BamH1 and Xba1 sites underlined.

B. miR155 hairpin precursor, predicted fold (present within the BIC RNA):

SEQ ID NO: 155   5'   UUAAUGCUAAUUGUGAUAGGGGUU--UUGGC
                      |||||||||||:|:|||||||||:::|||  c
                  3'  AAUUACGAUUG-UCC-AUCCUCAGUCAGUCU underlined sequence is the expected 22nt miR155 miRNA. Watson-Crick base pairs indicated by lines, GU base pairs indicated by two dots. Dashes indicate gaps.

FIGURE 11

C. BIC hairpin cloning site:

```
            >Bbs1/Bbv2   >Eco57I                              >Bbs1/Bbv2
                                                                          Stu1
             10        20        30        40        50
SEQ ID NO: 156  GGCTTGCTGAAGGCTGTATGCTGTTGTCTTCAAGATCTGGAAGACACAGGACACAAGGCCTGTTACTAGCACT
                CCGAACGACTTCCGACATACGACAACAGAAGTTCTAGACCTTCTGTGTCCTGTGTTCCGGACAATGATCGTGA
```

Bbs1 cut:
```
SEQ ID NO: 157  GGCTTGCTGAAGGCTGTAT           AGGACACAAGGCCTG   SEQ ID NO: 159
SEQ ID NO: 158  CCGAACGACTTCCGACATACGAC           GTGTTCCGGAC   SEQ ID NO: 160
``` hairpin template with compatible ends:

```
SEQ ID NO: 161   GCTGNNNNNNNNNNNN...NNNNNNNNNNNC
SEQ ID NO: 162         NNNNNNNNNN...NNNNNNNNNNNNGTCCT
```

Numbering is arbitrary. Position of what would correspond to the first and last nt of miR155 is indicated in bold. Note that most of the miR155 sequence is missing, and the Bbs1 restriction sites allow precise replacement of the miR155 sequence with any sequence. Normally we would insert a DNA template for two complementary siRNA strands with an intervening loop. The loop can, but need not, match the miR155 loop. See fig. 2 for examples

FIG. 12 miR155 hairpin precursor, predicted fold (present within the BIC RNA):

SEQ ID NO: 163
```
     UUAAUGCUAAUUGUGAUAGGGGUU--UUGGC
     |||||||  |  ||||||||:  |::| C
  3' AAUUACGAUUG-UCC-AUCCUCAGUCAGUCU
```

ND1BHP1 hairpin precursor, predicted fold (present within the BIC RNA):

SEQ ID NO: 164
```
     UUGCAGCAAUCUUAGCAAAAGGUU--UUGGC
     ||||||| :|| ||||||:|:  |:::| C
     AACGUCGUUAG-gUC-UUUUnCAGUCAGUCU
```

64nt DNA templates for ND1BHP1 that were inserted into the CXS2+BIC23 vector at Bbs1 sites (see fig 1C):

SEQ ID NO: 165
SEQ ID NO: 166
```
GCTGTTGCAGCAATCTTAGCAAAAGTTTTGGCCTCTGACTGACTTTTCTGATTGCTGCAAC
AACGTCGTTAGAATCGTTTTCAAACGGAGACTGACTGAAAAAGACCTAACGACGTTGTCCT
```

ND1BHP2 hairpin precursor, predicted fold (present within the BIC RNA):

SEQ ID NO: 167
```
     UUGCAGCAAUCUUAGCAAAAGGUU--UUGGC
     |||||||||||||||||||||  |:::| C
     AACGUCGUUAGgUCGUUUUCCAGUCAGUCU
```

This version has some of the mismatches in ND1BHP1 removed.

Underlined sequences are the expected 22nt miR155 miRNA, or the expected neuroD1 complementary siRNA. Watson-Crick base pairs indicated by lines, GU

FIG. 13

Luciferase assays

A. 08/03/02 luciferase assay
target: CS2+Luc-miR155as

| siRNA vector | Luc | B-Gal | (Luc/B-Gal)*1000 | luc activity % |
|---|---|---|---|---|
| CS2BIC | 190311 | 779985 | 244 | 12 |
| CS2eGFPBIC | 204914 | 582670 | 352 | 18 |
| CS2BIC23-ND1BHP1 | 1097336 | 577074 | 1902 | 97 |
| CS2eGFP | 1007557 | 512409 | 1966 | 100 |

B. 08/03/02 luciferase assay
target: CS2+Luc-ND3'UTR

| siRNA vector | Luc | B-Gal | (Luc/B-Gal)*1000 | luc activity % |
|---|---|---|---|---|
| CS2BIC23-ND1BHP1 | 79720 | 692039 | 115 | 11 |
| CS2BIC23-ND1BHP2 | 173555 | 781916 | 222 | 21 |
| CS2BIC | 1055765 | 1007735 | 1048 | 100 |

C. 07/30/02 luciferase assay
target: CS2+Luc-miR155as

| siRNA vector | Luc | B-Gal | (Luc/B-Gal)*1000 | luc activity % |
|---|---|---|---|---|
| CS2BIC | 214964 | 1797957 | 120 | 7 |
| CS2eGFPBIC | 211888 | 1549509 | 137 | 8 |
| CS2BICshort | 1573144 | 1558825 | 1009 | 61 |
| CS2BIC23-ND1BHP1 | 1446892 | 872082 | 1659 | 100 |

Mouse BIC sequences inserted into the CS2+ vector between the BamH1 andXba1 sites. The 22 nt miR155 siRNA is underlined.

SEQ ID NO: 168

GTGGTTTAAGTTGCATATCCCTTATCCTCTGGCTGCTGGAGGCTTGCTGAAGGCTGTAT
GCTGTTAATGCTAATTGTGATAGGGGTTTTGGCCTCTGACTGACTCCTACCTGTTAGCA
TTAACAGGACACAAGGCCTGTTACTAGCACTCACATGAACATGAACAAATGGCCACCGTGGGAG
GATGACAAGTCCAAGAGTCACCCTGCTGGATGAACGTAGATGTCAGACTCTATCATTTA
ATGTGCTAGTCATAACCTGGTTACTAGGATAGTCCACTGTAAGTGTTACGATAAATGTC
ATTTAAAAGATAGCAGCAGTATCCTAAACAACATCTCAACTTCAAGCCCACATGTTT
ATTTTTATCTTGAATGGAAAGTGAAACTTGTATCATTTTTATTTCAAAATTATGTTCA
TAACCATCTTCAATGATTCAACCAGAATACAAATGAATGCACT

B.

BIC23. Modified version of the mouse BIC sequences inserted into the CS2+ vector between the BamH1 andXba1 sites. Most of the miR155 hairpin has been replaced by a synthetic sequence (underlined) to allow insertion of new hairpin siRNA templates between two Bbs1 restriction sites.

SEQ ID NO: 169

GTGGTTTAAGTTGCATATCCCTTATCCTCTGGCTGCTGGAGGCTTGCTGAAGGCTGTAT
GCTGTTGTCTTCAAGATCTGGAAGACACAGGACACAAGGCCTGTTACTAGCACTCACAT
GGAACAAATGGCCACCGTGGGAGGATGACAAGTCCAAGAGTCACCCTGCTGGATGAACG
TAGATGTCAGACTCTATCATTTAATGTGCTAGTCATAACCTGGTTACTAGGATAGTCCA
CTGTAAGTGTTACGATAAATGTCATTTAAAAGATAGATCAGCAGTATCCTAAACAACAT
CTCAACTTCAAGCCCACATGTTTATTTTTATCTTGAATGGAAAGTGAAACTTGTATCA
TTTTTATTTCAAAATTATGTTCATAACCATCTCAATGATTCAACCAGAATACAAAATG
AATGCACT

US 7,387,896 B2

MICRORNA VECTORS

This application is a continuation in part of U.S. patent application Ser. No. 10/397,943, filed Mar. 26, 2003 now abandoned and claims priority to provisional patent application Ser. No. 60/581,504, filed Jun. 21, 2004, each of which is herein incorporated by reference in its entirety.

The present application was funded in part with government support under grant numbers RO1-NS38698 and MH063992 awarded by the National Institutes of Health. The government has certain rights in this invention.

FIELD OF THE INVENTION

The present invention relates to gene silencing, and in particular to compositions of microRNA sequences and vectors and to methods of synthesizing such in vitro and in vivo, and to methods of using such to regulate gene expression.

BACKGROUND OF THE INVENTION

Recently the field of reverse genetic analysis, or gene silencing, has been revolutionized by the discovery of potent, sequence specific inactivation of gene function, which can be induced by double-stranded RNA (dsRNA). This mechanism of gene silencing is termed RNA interference (RNAi), and it has become a powerful and widely used tool for the analysis of gene function in invertebrates and plants (reviewed in Sharp, P. A. (2001) *Genes Dev* 15, 485-90). Introduction of double-stranded RNA (dsRNA) into the cells of these organisms leads to the sequence-specific destruction of endogenous RNAs, when one of the strands of the dsRNA corresponds to or is complementary to an endogenous RNA. The result is inhibition of the expression of the endogenous RNA. Endogenous RNA can thus be targeted for inhibition, by selecting dsRNA of which one strand is complementary to the sense strand of an endogenous RNA. During RNAi, long dsRNA molecules are processed into 19-23 nucleotide (nt) RNAs known as short-interfering RNAs (siRNAs) that serve as guides for enzymatic cleavage of complementary RNAs (Elbashir, S. M. et al. (2001) *Genes Dev* 15, 188-2000; Parrish, S. et al. (2000) *Mol Cell* 6, 1077-87; Nykanen, A. et al. (2001) *Cell* 107, 309-21; Elbashir, S. M. et al. (2001) *Embo J* 20, 6877-88; Hammond, S. M. et al. (2000) *Nature* 404, 293-6; Zamore, P. D. et al. (2000) *Cell* 101, 25-33; Bass, B. L. (2001) *Nature* 411,428-9; and Yang, D. et al. (2000) *Curr Biol* 10, 1191-200). In addition, siRNAs can function as primers for an RNA-dependent RNA polymerase, leading to the synthesis of additional dsRNA, which in turn is processed into siRNAs to amplify the effects of the original siRNAs (Sijen, T. et al. (2001) *Cell* 107, 465-76; and Lipardi, C. et al. (2001) *Cell* 107, 297-307). Although the overall process of siRNA inhibition has been characterized, the specific enzymes that mediate siRNA function remain to be identified.

In mammalian cells, dsRNA is processed into siRNAs (Elbashir, S. M. et al. (2001) *Nature* 411, 494-8; Billy, E. et al. (2001) *Proc Natl Acad Sci USA* 98, 14428-33; and Yang, S. et al. (2001) *Mol Cell Biol* 21, 7807-16), but RNAi was not successful in most cell types due to nonspecific responses elicited by dsRNA molecules longer than about 30 nt (Robertson, H. D. & Mathews, M. B. (1996) *Biochimie* 78, 909-14). However, Tuschl and coworkers recently made the remarkable observation that transfection of synthetic 21-nt siRNA duplexes into mammalian cells effectively inhibits endogenous genes in a sequence specific manner (Elbashir, S. M. et al. (2001) *Nature* 411, 494-8; and Harborth, J. et al. (2001) *J Cell Sci* 114, 4557-65). These siRNA duplexes are too short to trigger the nonspecific dsRNA responses, but they still trigger destruction of complementary RNA sequences (Hutvagner, G. et al. (2001) *Science* 293, 834-8). This was a stunning discovery, and was followed by its utilization by several laboratories to knock out different genes in mammalian cells. The reported results demonstrate that siRNA appears to work quite well in most instances. However, a major limitation to the use of siRNA in host cells, and in particular in mammalian cells, is the method of delivery.

Currently, the synthesis of the siRNA is expensive. Moreover, inducing cells to take up exogenous nucleic acids is a short-term treatment and is very difficult to achieve in some cultured cell types. This methodology does not permit long-term expression of the siRNA in cells or use of siRNA in tissues, organs, and whole organisms. It had also not been demonstrated that siRNA could effectively be expressed from recombinant DNA constructs to suppress expression of a target gene. Thus, what is needed is more economical methods of synthesizing siRNAs. What is also needed are compositions and methods to express and deliver siRNA intracellularly in mammalian cells, and indeed in other cells as well. Such compositions and methods would have great utility not only as research tools, but also as a potent therapy for both infectious agents and for genetic diseases, by inhibiting expression of targeted genes.

SUMMARY OF THE INVENTION

The present invention relates to gene silencing, and in particular to compositions of microRNA sequences and vectors and to methods of synthesizing such in vitro and in vivo, and to methods of using such to regulate gene expression.

The present invention provides improved compositions and methods for inhibiting the expression of gene of interest. In some embodiments, the present invention provides vectors utilizing minimal BIC miRNA precursor sequences for use in expressing a miRNA complementary to a target gene and methods of using the vectors to inhibit expression of the target gene. In other embodiments, the present invention provides compositions and methods for expressing a miRNA within a intron or mRNA of a gene of interest, while still allowing protein expression from the gene.

For example, in some embodiments, the present invention provides a composition comprising a vector, the vector comprising a sequence encoding an least a portion of a BIC miRNA precursor molecule operably linked to a promoter, wherein the portion comprises at least nucleotides 1-111 of SEQ ID NO:47, and wherein the promoter permits expression of the miRNA in a cell. In some embodiments, the portion comprises SEQ ID NO: 49. In certain embodiments, bases 29-50 and 68-87 of SEQ ID NO:47 are replaced with sequences complementary to the target mRNA, and wherein the bases 29-50 are at least partially complementary to the bases 62-87. In some embodiments, miRNA is produced from the DNA molecule as a hairpin RNA. In some embodiments, miRNA includes at least a portion of a miR155 miRNA. In some embodiments, the promoter is a RNA polymerase III promoter (e.g., a U6 promoter). In other embodiments, the promoter is a RNA polymerase II promoter (e.g., a simian CMV promoter, a human ubiquitin promoter, or a mouse PGK promoter).

The present invention further provides a composition comprising a vector, the vector comprising a sequence encoding at least a portion of a miRNA precursor molecule operably linked to a promoter, and wherein the sequence is located within an intron or an untranslated region of an mRNA. In some embodiments, the miRNA precursor is a BIC miRNA (e.g., SEQ ID NO: 47 or 49). In some embodiments, the mRNA encodes a protein. In preferred embodiments, the protein is expressed. In some embodiments, miRNA is produced from the DNA molecule as a hairpin RNA. In some embodiments, miRNA includes at least a portion of a miR155 miRNA. In some embodiments, the promoter is a RNA polymerase III promoter (e.g., a U6 promoter). In other embodiments, the promoter is a RNA polymerase II promoter (e.g., a simian CMV promoter, a human ubiquitin promoter, or a mouse PGK promoter).

The present invention additionally provides a method for inhibiting the function of a target RNA molecule, comprising transfecting a cell with a DNA molecule comprising a sequence encoding an least a portion of a BIC miRNA precursor molecule operably linked to a promoter, wherein the portion comprises at least nucleotides 1-111 of SEQ ID NO:47, and wherein the promoter can be expressed in the cell, wherein the BIC miRNA encodes an miRNA complementary to a portion of the target RNA molecule. In some embodiments, the portion comprises SEQ ID NO:49. In certain embodiments, bases 29-50 and 68-87 of SEQ ID NO:47 are replaced with sequences complementary to the target mRNA, and wherein the bases 29-50 are at least partially complementary to the bases 62-87. In some embodiments, miRNA is produced from the DNA molecule as a hairpin RNA. In some embodiments, miRNA includes at least a portion of a miR155 miRNA. In some embodiments, the promoter is a RNA polymerase III promoter (e.g., a U6 promoter). In other embodiments, the promoter is a RNA polymerase II promoter (e.g., a simian CMV promoter, a human ubiquitin promoter, or a mouse PGK promoter). In some embodiments, the cell is a mammalian (e.g., human). In some embodiments, the cell is in an organism.

In yet other embodiments, the present invention provides a method for inhibiting the function of a target RNA molecule, comprising transfecting a cell with a DNA vector, the vector comprising a sequence encoding an least a portion of a miRNA precursor molecule operably linked to a promoter, and wherein the sequence is located within an intron or an untranslated region of an mRNA, and wherein the promoter can be expressed in the cell, and wherein the miRNA encodes an miRNA complementary to a portion of the target RNA molecule. In some embodiments, the miRNA precursor is a BIC miRNA (e.g., having the nucleic acid sequence of SEQ ID NO:47 or 49). In some embodiments, the mRNA encodes a protein. In preferred embodiments, the protein is expressed. In some embodiments, miRNA is produced from the DNA molecule as a hairpin RNA. In some embodiments, miRNA includes at least a portion of a miR155 miRNA. In some embodiments, the promoter is a RNA polymerase III promoter (e.g., a U6 promoter). In other embodiments, the promoter is a RNA polymerase II promoter (e.g., a simian CMV promoter, a human ubiquitin promoter, or a mouse PGK promoter). In some embodiments, the cell is a mammalian (e.g., human). In some embodiments, the cell is in an organism.

DESCRIPTION OF THE FIGURES

FIG. 4 shows RNAi using ds siRNAs and hairpin siRNAs expressed in cells from an RNA polymerase III promoter. Panel A (SEQ ID NOS:83-85) shows an example of the transcribed region of a mouse U6 promoter siRNA vector (U6-BT4as). The first nucleotide of the U6 transcript corresponds to the first nucleotide of the siRNA (+1), while the siRNA terminates at a stretch of 5 T residues in the vector (term). Panel B (SEQ ID NOS:86-94) shows sequences for the ds siRNAs and hairpin siRNAs to neuronal β-tubulin synthesized from the U6 vector. Expected RNA duplexes are shown for the hairpin siRNAs and for pairs of single strand siRNAs (notation as in FIG. 1). Panel C shows quantitation of cells with detectable neuronal β-tubulin and HuC/HuD after co-transfection of biCS2+MASH1/GFP and various U6 vectors (as described in FIG. 3). The expression of either siRNA hairpin reduces the number of positive cells at least 100-fold, while co-transfection of two vectors expressing individual siRNA strands (resulting is ds siRNA) reduces the number of neuronal β-tubulin cells about 5-fold. HuC/D expression is unaltered.

FIG. 5. Panel A (SEQ ID NO:95) shows the common T7 promoter oligonucleotide used for all T7 siRNA templates; the 17-nt minimal T7 promoter sequence is underlined. Oligonucleotide length was increased to 20 nt to increase duplex stability in the 37° T7 synthesis reaction and improve siRNA yield (based upon experimental observations). Panel B (SEQ ID NOS:96-112) shows the sequences of DNA oligonucleotide template strands for each siRNA synthesized by in vitro transcription. Panel C (SEQ ID NOS:113-130) shows the sequences of DNA inserted in the mU6pro vector to create various U6 siRNA expression vectors. The sequences shown are annealed oligonucleotide duplexes with overhanging ends compatible with the Bbs1 and Xba1 sites in the vector.

FIG. 9. Sequences of hairpin siRNAs targeted against GSK3α and GSK3β. (A) Predicted structures of hairpin siRNAs targeted against either GSK3α or GSK3β (SEQ ID NOS:145-148). (B) Predicted structure of a hairpin siRNAs targeted against both GSK3α and GSK3β by using alternate GC or GU base pairing with the two underlined Gs (SEQ ID No:149. (C) Potential base pairing of the antisense sequence of the GSK3α/β HP with the sequences of the mouse GSK3α and GSK3β mRNAs, including GU base pairs with GSK3β. (SEQ ID NOS:150-152). Sequence notation as in FIG. 1.

FIG. 11(A) shows primers (SEQ ID NOS:153-154) use for amplifying exon 3 of the mouse BIC gene.

FIG. 11(B) shows a predicted structure (SEQ ID NOS: 155) for the miR155 hairpin precursor.

FIG. 11(C) shows the BIC hairpin cloning site (SEQ ID NOS:156-162).

FIG. 12 shows the predicted structures for the miR155 (SEQ ID NOS:163), ND1BHP1 (SEQ ID NOS:164-166), and ND1BHP2 (SEQ ID NOS:167) hairpin precursor molecules.

FIGS. 13A-13C show the effects of co-transfection of the indicated constructs on luciferase activity expressed from target vectors.

FIGS. 14A-14B show 2 unmodified and modified mouse BIC sequences (SEQ ID NOS:168-169).

DEFINITIONS

Figure 1:
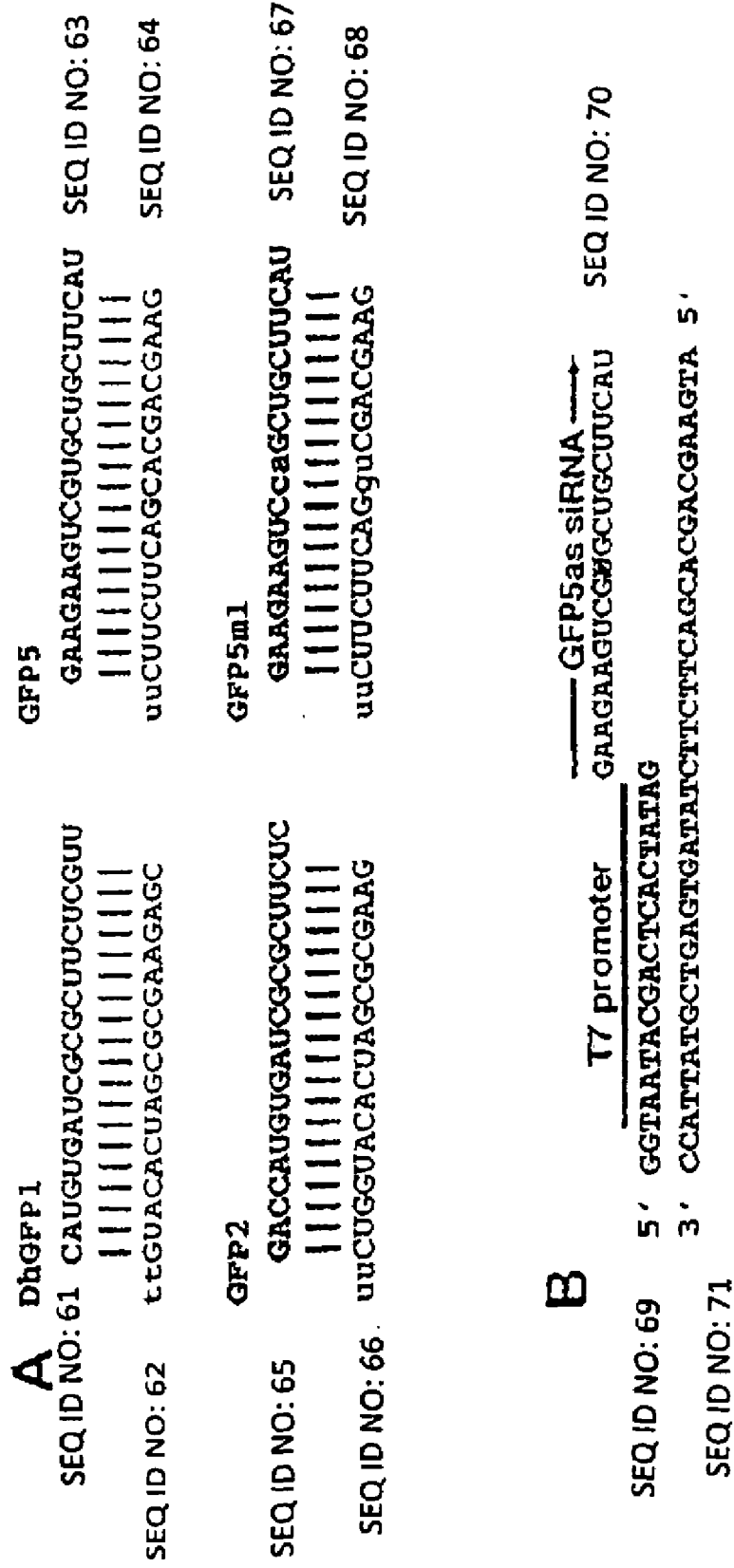
FIG. 1 shows the results of RNA interference using 21 nt siRNAs synthesized by in vitro transcription. Panel A (SEQ ID NOS:61-68) shows the sequences and expected duplexes for siRNAs targeted to GFP. Both DhGFP1 strands were chemically synthesized, while other siRNA strands were synthesized by in vitro transcription with T7 RNA polymerase. GFP5m1 contains a two base mismatch with the GFP target. Nucleotides corresponding to the antisense strand of GFP are in bold; nucleotides mismatched with the target are lower case. Panel B (SEQ ID NOS:69-71) shows an example of the structure of a DNA oligonucleotide template for T7 transcription. Panel C shows the quantitation of siRNA inhibition of luciferase activity from vectors with and without GFP sequences inserted into the 3' untranslated region of luciferase (luc: luciferase; pA: SV40 polyadenylation site). siRNAs synthesized either chemically or by in vitro transcription show similar effectiveness at inhibiting luciferase if GFP sequences are present in the luciferase mRNA, while the mismatched GFP5m1 siRNA does not inhibit effectively. The "no siRNA" control is set to 100% for each set of transfections. Data is averaged from 3 experiments with standard errors indicated.
Figure 1:
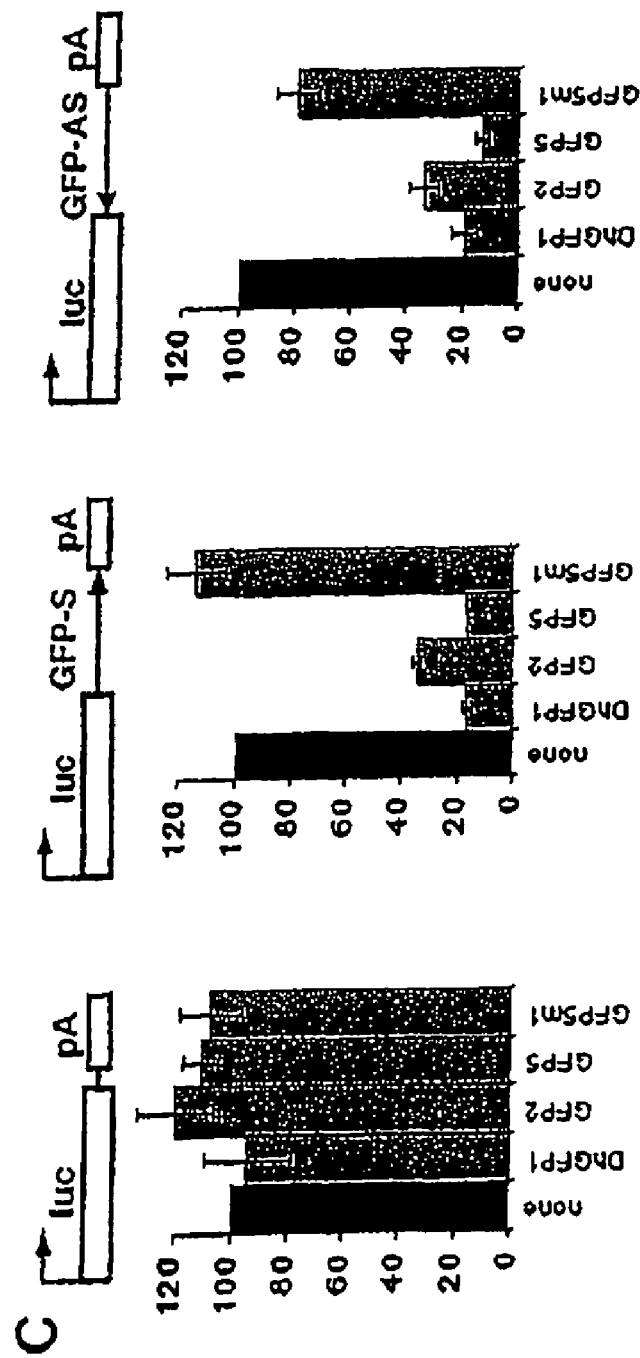

To facilitate an understanding of the present invention, a number of terms and phrases as used herein are defined below:

The terms "protein" and "polypeptide" refer to compounds comprising amino acids joined via peptide bonds and are used interchangeably.

As used herein, where "amino acid sequence" is recited herein to refer to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycolsylations and addition of lipid moieties.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, and/or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in 0 reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" may also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise a gene sequence that comprise cDNA forms of the gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The terms "region" or "portion" when used in reference to a nucleic acid molecule refer to a set of linked nucleotides that is less than the entire length of the molecule.

The term "strand" when used in reference to a nucleic acid molecule refers to a set of linked nucleotides which comprises either the entire length or less than or the entire length of the molecule.

The term "links" when used in reference to a nucleic acid molecule refers to a nucleotide region which joins two other regions or portions of the nucleic acid molecule; such connecting means are typically though not necessarily a region of a nucleotide. In a hairpin siRNA molecule, such a linking region may join two other regions of the RNA molecule which are complementary to each other and which therefore can form a double stranded or duplex stretch of the molecule in the regions of complementarity; such links are usually though not necessarily a single stranded nucleotide region contiguous with both strands of the duplex stretch, and are referred to as "loops".

The term "linker" when used in reference to a multiplex siRNA molecule refers to a connecting means that joins two siRNA molecules. Such connecting means are typically though not necessarily a region of a nucleotide contiguous with a strand of each siRNA molecule; the region of contiguous nucleotide is referred to as a "joining sequence."

The term "a polynucleotide having a nucleotide sequence encoding a gene" or "a polynucleotide having a nucleotide sequence encoding a gene" or "a nucleic acid sequence encoding" a specified RNA molecule or polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. This is also of importance in efficacy of siRNA inhibition of gene expression or of RNA function.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions)

for optimal alignment of the two sequences. Optimal alignment of sequences for aligning a comparison window may be conducted by the local homology algorithm of Smith and Waterman (Smith and Waterman, *Adv. Appl. Math.* 2: 482 (1981)) by the homology alignment algorithm of Needleman and Wunsch (Needleman and Wunsch, *J. Mol. Biol.* 48:443 (1970)), by the search for similarity method of Pearson and Lipman (Pearson and Lipman, *Proc. Natl. Acad. Sci.* (U.S.A.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$(% G+C), when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5× SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q_replicase, MDV-1 RNA is the specific template for the replicase (Kacian et al., Proc. Natl. Acad. Sci. USA, 69:3038 (1972)). Other nucleic acids will not be replicated by this amplification enzyme. Similarly, in the case of T7 RNA polymerase, this amplification enzyme has a stringent specificity for its own promoters (Chamberlin et al., Nature, 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press (1989)).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and, where the RNA encodes a protein, into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "RNA function" refers to the role of an RNA molecule in a cell. For example, the function of mRNA is translation into a protein. Other RNAs are not translated into a protein, and have other functions; such RNAs include but are not limited to transfer RNA (tRNA), ribosomal RNA (rRNA), and small nuclear RNAs (snRNAs). An RNA molecule may have more than one role in a cell.

The term "inhibition" when used in reference to gene expression or RNA function refers to a decrease in the level of gene expression or RNA function as the result of some interference with or interaction with gene expression or RNA function as compared to the level of expression or function in the absence of the interference or interaction. The inhibition may be complete, in which there is no detectable expression or function, or it may be partial. Partial inhibition can range from near complete inhibition to near absence of inhibition; typically, inhibition is at least about 50% inhibition, or at least about 80% inhibition, or at least about 90% inhibition.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap, Plant Mol. Biol. 24:119-127 (1994)) promoters. Such promoters have been used successfully to direct the expression of heterologous nucleic acid sequences in transformed plant tissue.

In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York (1989) pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s) from one cell to another. The term "vehicle" is sometimes used interchangeably with "vector." A vector may be used to transfer an expression cassette into a cell; in addition or alternatively, a vector may comprise additional genes, including but not limited to genes which encode cell marker proteins, by which cell transfection can be determined, selection proteins, be means of which transfected cells may be selected from non-transfected cells, or reporter proteins, by means of which an effect on expression or activity or function of the reporter protein can be monitored.

The term "expression cassette" refers to a chemically synthesized or recombinant DNA molecule containing a desired coding sequence and appropriate nucleic acid sequences necessary for the expression of the operably linked coding sequence either in vitro or in vivo. Expression in vitro includes expression in transcription systems and in transcription/translation systems. Expression in vivo includes expression in a particular host cell and/or organism. Nucleic acid sequences necessary for expression in prokaryotic cell or in vitro expression system usually include a promoter, an operator (optional), and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases, referred to as a transcription template in the art, include a template DNA strand which has a polymerase promoter region followed by the complement of the RNA sequence desired. In order to create a transcription template, a complementary strand is annealed to the promoter portion of the template strand.

The term "expression vector" refers to a vector comprising one or more expression cassettes. Such expression cassettes include those of the present invention, where expression results in an siRNA transcript.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, bacterial infection, viral infection, biolistics (i.e., particle bombardment) and the like. The terms "transfect" and "transform" (and grammatical equivalents, such as "transfected" and "transformed") are used interchangeably.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos. 6,074, 859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, $\beta$-galactosidase, alkaline phosphatase, and horse radish peroxidase.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" when used in reference to DNA refers to a sequence that is complementary to a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The term "ds siRNA" refers to a siRNA molecule that comprises two separate unlinked strands of RNA which form a duplex structure, such that the siRNA molecule comprises two RNA polynucleotides.

The term "hairpin siRNA" refers to a siRNA molecule that comprises at least one duplex region where the strands of the duplex are connected or contiguous at one or both ends, such that the siRNA molecule comprises a single RNA polynucleotide. The antisense sequence, or sequence which is complementary to a target RNA, is a part of the at least one double stranded region.

The term "fill hairpin siRNA" refers to a hairpin siRNA that comprises a duplex or double stranded region of about 18-25 base pairs long, where the two strands are joined at one end by a linking sequence, or loop. At least one strand of the duplex region is an antisense strand, and either strand of the duplex region may be the antisense strand. The region linking the strands of the duplex, also referred to as a loop, comprises at least three nucleotides. The sequence of the loop may also a part of the antisense strand of the duplex region, and thus is itself complementary to a target RNA molecule.

The term "partial hairpin siRNA" refers to a hairpin siRNA which comprises an antisense sequence (or a region or strand complementary to a target RNA) of about 18-25 bases long, and which forms less than a fill hairpin structure with the antisense sequence. In some embodiments, the antisense sequence itself forms a duplex structure of some or most of the antisense sequence. In other embodiments, the siRNA comprises at least one additional contiguous sequence or region, where at least part of the additional sequence(s) is complementary to part of the antisense sequence.

The term "mismatch" when used in reference to siRNAs refers to the presence of a base in one strand of a duplex region of which at least one strand of an siRNA is a member, where the mismatched base does not pair with the corresponding base in the complementary strand, where pairing is determined by the general base-pairing rules. The term "mismatch" also refers to the presence of at least one additional base in one strand of a duplex region of which at least one strand of an siRNA is a member, where the mismatched base does not pair with any base in the complementary strand, or to a deletion of at least one base in one strand of a duplex region which results in at least one base of the complementary strand being without a base pair. A mismatch may be present in either the sense strand, or antisense strand, or both strands, of an siRNA. If more than one mismatch is present in a duplex region, the mismatches may be immediately adjacent to each other, or they may be separated by from one to more than one nucleotide. Thus, in some embodiments, a mismatch is the presence of a base in the antisense strand of an siRNA which does not pair with the corresponding base in the complementary strand of the target siRNA. In other embodiments, a mismatch is the presence of a base in the sense strand, when present, which does not pair with the corresponding base in the antisense strand of the siRNA. In yet other embodiments, a mismatch is the presence of a base in the antisense strand that does not pair with the corresponding base in the same antisense strand in a foldback hairpin siRNA.

The terms "nucleotide" and "base" are used interchangeably when used in reference to a nucleic acid sequence.

The term "strand selectivity" refers to the presence of at least one mismatch in either an antisense or a sense strand of a siRNA molecule. The presence of at least one mismatch in an antisense strand results in decreased inhibition of target gene expression.

The term "cellular destination signal" is a portion of an RNA molecule that directs the transport of an RNA molecule out of the nucleus, or that directs the retention of an RNA molecule in the nucleus; such signals may also direct an RNA molecule to a particular subcellular location. Such a signal may be an encoded signal, or it might be added post-transciptionally.

The term "enhancing the function" when used in reference to an siRNA molecule means that the effectiveness of an siRNA molecule in silencing gene expression is increased. Such enhancements include but are not limited to increased rates of formation of an siRNA molecule, decreased susceptibility to degradation, and increased transport throughout the cell. An increased rate of formation might result from a transcript which possesses sequences that enhance folding or the formation of a duplex strand.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "posttranscriptional gene silencing" or "PTGS" refers to silencing of gene expression in plants after transcription, and appears to involve the specific degradation of mRNAs synthesized from gene repeats.

The term "sequence-nonspecific gene silencing" refers to silencing gene expression in mammalian cells after transcription, and is induced by dsRNA of greater than about 30 base pairs. This appears to be due to an interferon response, in which dsRNA of greater than about 30 base pairs binds and activates the protein PKR and 2',5'-oligonucleotide synthetase (2',5'-AS). Activated PKR stalls translation by phosphorylation of the translation initiation factors eIF2alpha, and activated 2',5'-AS causes mRNA degradation by 2',5'-oligonucleeotide-activated ribonuclease L. These responses are intrinsically sequence-nonspecific to the inducing dsRNA.

The term "overexpression" refers to the production of a gene product in transgenic organisms that exceeds levels of production in normal or non-transformed organisms. The term "cosuppression" refers to the expression of a foreign gene that has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31-9.58).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DESCRIPTION OF THE INVENTION

The present invention relates to gene silencing, and in particular to compositions of hairpin siRNAs. The present invention also relates to methods of synthesizing hairpin siRNAs and double-stranded siRNAs in vitro and in vivo, and to methods of using such siRNAs to inhibit gene expression. In some embodiments, hairpin siRNAs possess strand selectivity. In other embodiments, more than one hairpin siRNAs is present in a single RNA structure/molecule.

I. Development of the Invention

The use of siRNAs to inhibit gene expression in host cells, and in particular in mammalian cells, is a promising new approach for the analysis of gene function. However, current methods suffer from several disadvantages, which include an expensive chemical synthesis of siRNA and the requirement that cells be induced to take up exogenous nucleic acids, which is a short-term treatment and is very difficult to achieve in some cultured cell types, and which does not permit long-term expression of the siRNA in cells or use of siRNA in tissues, organs, and whole organisms. It had also not been demonstrated that siRNA could effectively be expressed from recombinant DNA constructs to suppress expression of a target gene.

During the development of the present invention, the possibility of synthesizing siRNAs within host cells, and in particular within mammalian cells, using an expression vector was explored as a means to facilitate the delivery of siRNAs. A siRNA expression vector would facilitate transfection experiments in cell culture, as well as allow the use of transgenic or viral delivery systems. As a first step, siRNA designs better suited to expression vectors were evaluated; one such design is a hairpin RNA, in which both strands of a siRNA duplex are included within a single RNA molecule and the strands connected by a loop at one end. To facilitate testing different siRNA designs, a method was developed for an inexpensive and rapid procedure for siRNA synthesis; this method comprises the use of RNA transcription by bacteriophage RNA polymerases. In particular, the T7 in vitro transcription from oligonucleotide templates (Milligan, J. F. et al. (1987) *Nucleic Acids Res* 15, 8783-98) was used. This method was used to synthesize both conventional (or double stranded, or ds) and hairpin siRNAs, as well as mutant versions of these molecules. Gene inhibition was demonstrated by in vitro transcribed ds siRNAs and hairpin siRNAs using transfection into mouse P19 cells (mouse P19 cells are a model system for neuronal differentiation).

For synthesis of siRNAs in cells, an objective was to express short RNAs with defined ends in cells.

Transcriptional termination by RNA polymerase III is known to occur at runs of four consecutive T residues in the DNA template (Tazi, J. et al. (1993) *Mol Cell Biol* 13, 1641-50; and Booth, B. L., Jr. & Pugh, B. F. (1997) *J Biol Chem* 272, 984-91), providing one mechanism to end a siRNA transcript at a specific sequence. In addition, previous studies have demonstrated that the RNA polymerase III based expression vectors could be used for the synthesis of short RNA molecules in mammalian cells (Noonberg, S. B. et al. (1994) *Nucleic Acids Res* 22, 2830-6; and Good, P. D. et al. (1997) *Gene Ther* 4, 45-54). While most genes transcribed by RNA polymerase III require cis-acting regulatory elements within their transcribed regions, the regulatory elements for the U6 small nuclear RNA gene are contained in a discrete promoter located 5' to the U6 transcript (Reddy, R. (1988) *J Biol Chem* 263, 15980-4).

Using an expression vector with a mouse U6 promoter, as described in more detail below and in Examples 1, 5 and 6, it was discovered that both hairpin siRNAs and pairs of single-stranded siRNAs expressed in cells (which are contemplated to form duplex or ds siRNA) can inhibit gene expression. Inhibition by hairpin siRNAs expressed from the U6 promoter was discovered to be more effective than the other methods tested, including the transfection of in vitro synthesized ds siRNA. Moreover, inhibition by hairpin siRNAs is sequence-specific, as a two base mismatch between an in vitro synthesized hairpin siRNA and its target abolished inhibition, and even a single base mismatch in one hairpin strand allowed differential inhibition of sense and antisense target strands.

Experiments conducted during the course of development of the present invention resulted in the development of an RNA polymerase (pol) II based hairpin expression vector system for production of siRNAs in vivo. In some embodiments, the use of RNA pol II instead of RNA pol III for hairpin synthesis offers several advantages, including but not limited to the following:

1) The technology for expression of RNA pol II synthesized mRNAs in a tissue specific or inducible manner is well-characterized and extensive, while such technology is more primitive for RNA pol III synthesized RNAs;

2) RNA pol II hairpin siRNA precursors may be more suitable than RNA pol III hairpin siRNA precursors for retroviral delivery, since retroviruses contain pol II promoters; and 3) RNA pol II does not terminate at runs of 4+ Ts in a template sequence. This will allow greater flexibility in siRNA design. For example, in some embodiments it may be desirable to include 3 or more consecutive U nucleotides within an siRNA. Such an RNA could not be synthesized using a polIII expression system, because the consecutive Us would cause termination of transcription.

For inhibition of an endogenous gene by in vivo production of a hairpin siRNAs, expression of the siRNAs from a transfected U6 expression vector was one particularly effective method tested. For example, inhibition of the expression of neuronal β-tubulin protein in differentiating mouse P19 cells by in vivo synthesized hairpin siRNA resulted in a 100-fold decrease in the number of cells with detectable protein. The cells without detectable neuronal β-tubulin were still viable and expressed other markers of neuronal differentiation. It should be noted that neuronal β-tubulin expression is not detected until two days after transfection of bHLH expression vectors in most cells (Farah, M. H. et al. (2000) *Development* 127, 693-702). This delay probably allowed time for the expression of the hairpin siRNA from the cotransfected U6 vector prior to target gene expression, and may have facilitated detection of neuronal β-tubulin inhibition, since turnover of preexisting protein was not required.

Furthermore, in the present invention under the conditions described in the Examples, the inhibition of neuronal β-tubulin by a hairpin siRNA expressed from the U6 promoter in transfected cells was more effective than inhibition by two siRNA strands expressed from separate U6 vectors. It is believed that two siRNA strands must form a duplex (or ds siRNA) for inhibition of a target gene by RNAi. Although as described in the Examples, siRNA duplex formation in cells was not directly assessed, indirect support for duplex formation was provided by the observation that co-transfection of both sense and antisense U6 siRNA vectors was required for effective inhibition, consistent with a requirement for duplex formation by the two siRNAs. However, formation of a duplex by folding back of a hairpin siRNA transcript should be rapid and efficient, while formation of a duplex between two separate siRNA strand transcripts synthesized separately within a cell is likely to be less efficient. Thus, it is contemplated that duplex formation is the limiting event for inhibition by siRNAs synthesized within cells, resulting in more efficient function of the hairpin design under the conditions described in the Examples.

In other embodiments for in vivo expression, a pol II expression system has been used. In some preferred embodiments, a microRNA (miRNA) hairpin precursor is used wherein the miRNA therein encoded and its complements a target RNA of interest.

When siRNAs are produced in vitro (as for example by in vitro transcription), inhibition by a transfected siRNA duplex comprised of two in vitro synthesized siRNA strands was somewhat more effective than transfection of an in vitro synthesized hairpin siRNA against the same target sequence. Although it is not necessary to understand the underlying mechanism, and the invention is not intended to be limited to any particular theory of any mechanism, it is speculated that this difference might be due to more efficient recognition of a siRNA duplex, composed of two separate siRNA strands, by the cellular machinery that mediates RNAi and/or other events subsequent to duplex formation. Recognition of a target sequence by a siRNA strand includes unwinding of the siRNA duplex and formation of a new duplex with the target RNA (Nykanen, A. et al. (2001) *Cell* 107, 309-21). For hairpin siRNA molecules, it is speculated that under the conditions described in the Examples, this process could be less efficient. Alternately, it is speculated that under these conditions, hairpin siRNAs might need additional processing, such as cleavage within the loop, prior to functioning. It is also possible the synthesis of siRNAs in the nucleus directs these molecules to cellular compartments distinct from those accessible to siRNAs introduced by lipid-mediated transfection, thus altering their effectiveness (Bertrand, E. et al. (1997) *Rna* 3, 75-88).

The methods provided by the present invention of synthesizing siRNAs by transcription, either in vitro with an RNA dependent polymerase such as T7, or in vivo from an expression vector such as a U6 expression vector, provide economical alternatives to the chemical synthesis of siRNAs, Moreover, the methods and compositions of the present invention permit inhibition of gene function by RNAi using hairpin siRNAs synthesized in host cells, and in particular in mammalian cells, and are contemplated to have broad application. In some embodiments, this approach facilitates studies of gene function in transfectable cell lines. In other embodiments, this approach is adaptable to situations for which delivery of in vitro synthesized siRNAs by transfection may not be practical, such as primary cell cultures, studies in intact animals, and gene therapy.

Therefore, the present invention provides compositions comprising novel hairpin siRNAs, as described in more detail below. The present invention also provides compositions comprising expression cassettes and expression vectors comprising sequences from which novel hairpin siRNAs of the present invention can be transcribed. The present invention further provides compositions comprising expression cassettes and expression vectors comprising sequences from which separate stranded duplex siRNAs as described previously in published reports can also be transcribed. Moreover, the present invention provides methods of synthesizing siRNAs by transcription, either in vitro with an RNA dependent polymerase such as T7, or in vivo from an expression vector such as a U6 expression vector; these methods are described in more detail below. Both separate stranded duplex siRNAs, as described previously in published reports, and novel hairpin siRNAs of the present invention, can be synthesized both in vitro, such as by T7 transcription, or in vitro, as from an expression vector such as a U6 expression vector. The compositions and methods of the present invention have broad utility and applicability, as described in more detail above and below.

An RNA polymerase (pol) II based hairpin expression vector system was also developed as an extension to the RNA pol III based system. The use of RNA pol II instead of RNA pol III for hairpin synthesis potentially provides several advantages:

1) The technology for expression of RNA pol II synthesized mRNAs in a tissue specific or inducible manner is well-characterized and extensive, while such technology is more primitive for RNA pol III synthesized RNAs. However, we have not as of yet constructed inducible or tissue specific expression systems.

2) RNA pol II hairpin siRNA precursors may be more suitable than RNA pol III hairpin siRNA precursors for retroviral delivery, since retroviruses contain pol II promoters.

3) RNA pol II does not terminate at runs of 4+ Ts in a template sequence, potentially allowing additional flexibility in siRNA design (RNA pol III synthesized hairpin siRNAs cannot include more than 3 consecutive Us).

II. Compositions

A. siRNA siRNAs are involved in RNA interference (as described above), where one strand of a duplex (the antisense strand) is complementary to a target gene RNA. The siRNA molecules described to date are a duplex of short, complementary strands. Such duplexes are prepared by separately chemically synthesizing the two separate complementary strands, and then combining them in such a way that the two separate strands form duplexes. These duplex siRNAs are then used to transfect cells. Although there is much that remains unknown about the process of RNAi (such as the enzymes involved, as noted above), a recent report provides "rules" for the "rational" design of siRNAs which are the most potent siRNA duplexes (Elbashir et al. (2001) The EMBO J. 20(23): 6877-6888), where the rules were derived from siRNA mediation of RNAi in *Drosophila melanogaster* embryo lysate. These rules include that the siRNA duplexes be composed of 21 nucleotide sense and 21 nucleotide antisense siRNA strands selected to form a 19 base pair double helix with 2 nucleotide 3' end overhangs. Target recognition is highly sequence-specific, but the 3' most nucleotide of the guide (or antisense) siRNA does not contribute to the specificity of target recognition, whereas the penultimate nucleotide of the 3' overhang affects target RNA cleavage. The 5' end also appears more permissive for mismatched target RNA recognition when compared with the 3' end. Nucleotides in the center of the siRNA, located opposite to the target RNA cleavage site, are important determinants, and even single nucleotide changes essentially abolish RNAi. Identical 3' overhanging sequences are suggested to minimize sequence effects that may affect the ratio of sense- and anti-sense-targeting (and cleaving) siRNAs. Such rules, where applicable, may be useful in the design of the siRNAs of the present invention.

Hairpin siRNAs

In one aspect, the present invention provides a composition comprising a hairpin small interfering RNA (or siRNA). A hairpin siRNA comprises a double-stranded or duplex region, where most but not necessarily all of the bases in the duplex region are base-paired, and where the two strands of the duplex are connected by a third strand; the duplex region comprises a sequence complementary to a target RNA. The sequence complementary to a target RNA is an antisense sequence, and is frequently from about 18 to about 29 nucleotides long. Hairpin siRNA can be prepared as a single strand, which is contemplated to fold back into a hairpin structure. Different hairpin embodiments are contemplated.

Full hairpin siRNAs. In some aspects, a hairpin siRNA comprises a duplex (or double stranded) RNA region, where the two strands of the duplex are joined at one end by a third strand of RNA which is contiguous with each strand and which is not part of the duplex. One strand of the duplex region in the hairpin siRNA comprises a sequence complementary to a target RNA; thus, the target complementary sequence is an antisense sequence to the target RNA, and the strand comprising the antisense sequence is also referred to as an antisense strand. The antisense sequence in the duplex region is from about 18 to about 29 nucleotides long. The opposite paired strand of the duplex region of the hairpin siRNA comprises a sequence substantially complementary to the antisense sequence; thus the sequence complementary to the antisense sequence is a sense sequence, and the strand comprising the sense sequence is also referred to as the sense strand. The sense sequence is also substantially the same sequence as the target RNA. Either strand of the hairpin siRNA may comprise the antisense strand, as the order of the sense and antisense strands within a hairpin siRNA does not generally alter its inhibitory ability. For use in mammalian cells, in some embodiments the antisense sequence in the duplex region is about 18-23 bases long, and in other embodiments, the antisense sequence in the duplex region is about 19-21 bases long, and in yet other embodiments, the antisense sequence in the duplex region is about 19 bases long. In still other embodiments, the antisense sequence in the duplex region is about 23-29 bases long, whereas in other embodiments, the antisense sequence in the duplex region is about 25-28 bases long.

The third strand which joins the two strands of the duplex region of the hairpin siRNA is typically though not necessarily a loop of single stranded RNA. The loop comprises at least about 3 nucleotides; in some embodiments, it comprises from 3 to about 10 nucleotides, and in some other embodiments, it comprises 3 to about 7 nucleotides, and in yet other embodiments it comprises from 3 to 4 nucleotides. In some embodiments, at least some of the nucleotides of the loop are part of the antisense sequence which is complementary to the target RNA; therefore, these loop nucleotides which are part of the antisense sequence are themselves generally complementary to the target RNA, and are contemplated to contribute to the ability of the siRNA to silence genes. Thus, in different embodiments, from none to some to all of the loop nucleotides are part of the antisense sequence. For example, in some embodiments, two nucleotides of a three nucleotide loop are part of the antisense sequence; in some embodiments, the nucleotides of the antisense sequence in the duplex antisense strand and in the loop are contiguous. It is contemplated that in some embodiments, the loop provides stability, either temporal (as, for example, in preventing degradation) or structural (as, for example, in maintaining a certain configuration, or assisting in binding to RNA or protein). The loop may be subject to processing in vivo, such as cleavage. If the loop is cleaved, it may be cleaved off entirely, or in such a fashion as to leave an overhang; in some embodiments, the overhanging portion is part of the siRNA antisense sequence complementary to a target gene.

In other embodiments, the hairpin siRNA molecule comprises additional sequences of overhanging nucleotides at either the 3' end or the 5' end or both ends. Preferably, the nucleotide overhang is at the 3' end. Preferably, the nucleotide overhang is about two to five nucleotides; most preferably, the overhang is about two to three nucleotides. In some embodiments, the nucleotide overhang comprises a sequence of Us.

These embodiments are referred to as "full hairpin" siRNAs, where by "full hairpin" it is meant that a target complementary or antisense sequence is substantially completely paired or duplexed with a sense sequence, such that the duplex region is about as long as the antisense sequence, or from about 18 to about 29 base pairs long. "Substantially" completely paired includes the presence of at least one mismatch in the duplex region, where mismatch is defined above and below. Moreover, an antisense sequence may also include from one to all of the nucleotides in the loop sequence, which are generally not part of the duplex structure.

An example of a full hairpin siRNA sequence is shown below, where the loop comprises 3 nucleotides, and where:

N represents ribonucleotides complementary to target RNA (anti-sense sequence or strand, or N-sequence or strand);

C represents ribonucleotides complementary to the N-strand (sense sequence or strand, or C-sequence or strand); and n represents any nucleotide (it can be complementary to the target RNA).

(SEQ ID NO:3)
5' NNNNNNNNNNNNNNNNNNNNNnnnCCCCCCCCCCCCCCCCCCCCnn 3'

The expected folded structure of SEQ ID NO:3 is shown below, where the symbol "|" represents base pair interaction:

Note that the C ribonucleotides are by definition complementary to any cellular RNA strand that is complementary to the target RNA. Also, note that it is possible for some of the C nucleotides to be complementary to the target strand, depending on target sequence (e.g. some of the C nucleotides of the sense strand might be complementary to a palindromic target RNA sequence).

In designing a gene encoding a siRNA sequence, it is important to avoid sequences that bind to unintended targets. Therefore, the sequence of a hairpin siRNA molecule should be specific to the target gene; such specificity is usually achieved by a double-stranded region of about 19 nucleotide pairs. It has also been observed that the siRNA duplex region generally must have about 100% homology with the target gene, meaning that the antisense sequence must be completely or almost completely homologous or complementary to a segment or region of the RNA of the target gene for greatest inhibition of gene expression or RNA function.

Partial hairpin siRNAs. In another aspect, the present invention provides a composition comprising a partial hairpin siRNA. By "partial hairpin" it is meant that the siRNA comprises a sequence (or a strand) complementary to a target RNA (an antisense sequence), and if present, one or two additional sequences at one or both ends of the antisense sequence which may or may not contain nucleotides complementary to the antisense sequence, where the antisense sequence alone or together with the additional sequence(s) form(s) less than a full hairpin structure with the target complementary, or antisense, sequence. The target complementary or anti-sense sequence is about 18-29 bases long; in some embodiments, the sequence is about 19-23 bases long, and in other embodiments, the sequence is about 19 bases long. In yet other embodiments, the sequence is about 23-29 bases long, and in other embodiments, it is about 25-28 bases long, and in still other embodiments, it is about 28 bases long.

In some embodiments, the partial hairpin siRNA is a "partial foldback" siRNA. In this siRNA, the hairpin comprises short additions (extra nucleotides) at either or each end of an antisense sequence, where the additions are designed to fold back and form at least one or two short duplex regions; these duplex regions may be formed between the addition and the antisense strand, or between two portions of the addition. The ends of these short duplexes do not abut (i.e. the 5' and 3' nucleotides are not base-paired to adjacent bases). From none to all of the nucleotides in an addition may be complementary to the target RNA; thus, from none to all of the nucleotides in an addition may be part of an antisense sequence. From none to all of the nucleotides in an addition may be complementary to the antisense sequence; thus, from none to all of the nucleotides in an addition may be part of a sense sequence. Part of the antisense sequence and/or part of an addition forms a loop of single stranded nucleotides which effectively joins two strands of a duplex region; these loops are as described above for complete hairpin siRNAs, and thus from none to all of the nucleotides of a loop may be complementary to a target RNA.

An example of a partial foldback siRNA sequence is shown below, where X represents added nucleotides in each addition:

```
                                           (SEQ ID NO:4)
  5' XXX-NNNNNNNNNNNNNNNNNNNNNNNN-XXX 3'
```

The expected folded structure of SEQ ID NO:4 is shown below, where the 5' most nucleotide is shown in bold type.

```
        NNNNNNNNNNNNNNNNNNNN
      N |||                ||| N
        NXXX 5'        3'XXXN
```

The number of added nucleotides (Xs) in each addition can be smaller or larger than the 3 nucleotides exemplified; when two additions are present, they may but need not have the same number of nucleotides. At least one mismatch can be present in any duplex region formed by an addition, either with a portion of the antisense strand, or with a portion of the addition.

A partial foldback siRNA can also be designed in which the base pair regions at one or both ends of the structure includes sequences that are not complementary to the target RNA; these base pair regions are typically though not necessarily joined by a loop which is also not complementary to the target RNA. Of the many different embodiments possible, one is illustrated below, where:

X represents ribonucleotides added to create base pairs near the ends of the foldback RNA and which are not necessarily complementary to the target RNA; and x represents ribonucleotides of a loop region, which are not necessarily complementary to the target RNA.:

```
                                                (SEQ ID NO:5)
  5' XXXxxxXXX-NNNNNNNNNNNNNNNNNNNNNNNN-XXXxxxXXX 3'
```

The expected folded structure of SEQ ID NO:5 is shown below:

```
        xXXXNNNNNNNNNNNNNNNNNNNNNNNNXXXx
      x |||                          ||| x
        xXXX 5'                  3'XXXx
```

In other embodiments, the partial hairpin siRNA is a "complete foldback" siRNA. In these embodiments, siRNA antisense sequences are designed to fold back and form a partial duplex in which the 5' and 3' end nucleotides of the siRNA are base paired to adjacent bases elsewhere in the siRNA. Such an siRNA can be created by choosing an siRNA sequence complementary to a target RNA sequence (an antisense sequence) that permits appropriate base pairing. Not all bases in the complete foldback siRNA need to be paired with an opposing base. In some embodiments, a sequence of about 19 to 23 contiguous nucleotides (as illustrated by Ns below) are complementary to the target RNA. In other embodiments, the target complementary sequence is slightly longer than 23 nucleotides, from about 23 to about 29 contiguous nucleotides long.

An example of a complete foldback siRNA sequence is illustrated below, where the 5' most nucleotide is indicated by bold type:

```
  5' NNNNNNNNNNNNNNNNNNNNNNNN 3'  (SEQ ID NO:6)
```

The expected folded structure of SEQ ID NO:6 is shown below, where the symbol "|" represents possible base pair interaction (of which some but not all are required; the symbol ":" is included to emphasize the border between the 5' and 3' ends):

```
        NNNNNNNNNN
      N ||||::|||| N
        NNNNNNNNNN
           / |
          5' 3'
```

The design depicted above places some constraints upon the choice of sequence for a complete foldback siRNA. In some cases, an appropriate sequence complementary to a desired target may not exist. Thus, in other embodiments, a more general approach to the design of a complete foldback siRNA is to add one or more additional non-target complementary ribonucleotides (X) to one or both the ends of the RNA sequence to form a partial duplex in which the 5' and 3' end nucleotides of the RNA are base paired to adjacent bases elsewhere in the RNA. Note that mismatches between duplex regions are possible, especially if additional nucleotides are present.

An embodiment of a more general complete foldback siRNA sequence is illustrated below, in which 3 nucleotides (Xs) are added to each end of the target complementary RNA sequence; in this embodiment, the 5' most nucleotide is shown in bold type, and X represents potential ribonucleotides added to create base pairs near 5' and 3' ends, where the Xs need not be complementary to the target RNA:

```
  5' XXX-NNNNNNNNNNNNNNNNNNNNNNNN-XXX 3'  (SEQ ID NO:7)
```

The expected folded structure is shown below, where the symbol ":" is included to emphasize the border between the added bases and the sequence complementary to the target RNA:

```
        NNNNNNNNNNNN
      N ||||||::|||| N
        NNNNXXXXXXNN
           / |
          5' 3'
```

Intermediate embodiments between the two examples illustrated above are also contemplated, as are variant embodiments in which there are additional nucleotides added (Xs). In some embodiments, a complete foldback siRNA molecule is contemplated in which there is a 3' extension to the complete foldback siRNA (see below).

Hairpin siRNAs Extensions. In yet other embodiments, any of the hairpin siRNAs described above further comprise at least one extension at either the 3' or 5' end of the hairpin siRNA, where the extensions are not part of an RNA:RNA duplex. Such extensions are contemplated to facilitate the synthesis by different strategies for hairpin siRNAs. For example, a hairpin siRNA synthesized in a mammalian cell by RNA polymerase III is likely to end in a run of 4 Us. These 4 Us can be a part of the target complementary or antisense siRNA strand, or they can be part of a sense strand of the siRNA (when present); alternatively, these 4 bases can be an extension of the siRNA (i.e., not part of either antisense or sense strand), thus allowing additional flexibility in target sequence selection for the hairpin siRNA.

An embodiment is illustrated below for a 3' extension to a partial hairpin siRNA, where the 5' most nucleotide is shown in bold type, and the lower case x's denote added nucleotides to the target complementary sequence siRNA strand (Ns) that do not necessarily form an RNA duplex in the siRNA.

```
                                               (SEQ ID NO:8)
   5' XXX-NNNNNNNNNNNNNNNNNNNNNNNNNN-XXXxxxx 3'
```

The expected folded structure is shown below.

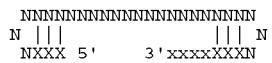

However, extensions of other lengths are contemplated for any of the hairpin siRNAs described above, at either the 5' or 3' end.

Hairpin siRNAs with Strand Specificity.

In other embodiments, the present invention provides a composition comprising any hairpin small interfering RNA (or siRNA) as described above, where at least one of the strands of the duplex comprises at least one mismatch. By "mismatch" it is meant the presence of a base in one strand of a duplex region of which at least one strand of an siRNA is a member, where the mismatched base does not pair with the corresponding base in the complementary strand, when pairing is determined by the general base-pairing rules. "Mismatch" also refers to the presence of at least one additional base in one strand of a duplex region of which at least one strand of an siRNA is a member, where the mismatched base does not pair with any base in the complementary strand, or to a deletion of at least one base in one strand of a duplex region which results in at least one base of the complementary strand being without a base pair. A mismatch may be present in either the sense strand, or antisense strand, or both strands, of an siRNA. If more than one mismatch is present in a duplex region, the mismatches may be immediately adjacent to each other, or they may be separated by from one to more than one nucleotide. Thus, in some embodiments, a mismatch is the presence of a base in the antisense strand of an siRNA which does not pair with the corresponding base in the complementary strand of the target siRNA. In other embodiments, a mismatch is the presence of a base in the sense strand, when present, which does not pair with the corresponding base in the antisense strand of the siRNA. In yet other embodiments, a mismatch is the presence of a base in the antisense strand that does not pair with the corresponding base in the same antisense strand in a foldback hairpin siRNA.

Although it is not necessary to understand the underlying mechanism to practice the invention, and the invention is not intended to be limited to any particular mechanism, it is thought that the presence of at least one missing base in one strand a duplex region results in a "bubble" formed by the extra base(s) in the opposite strand, and that this bubble might be at or near to a processing site. It is contemplated that processing includes cleavage of the duplex region. Thus, it is contemplated that in some embodiments, the inclusion of at least one missing base or a bubble might be used to signal processing of a duplex region.

Inhibition of gene expression by hairpin siRNA is sequence specific (as described in Examples 3 and 4); thus, the presence of a mismatch in a hairpin siRNA strand complementary to a target RNA can greatly decrease the resulting gene inhibition of the siRNA, and the presence of two mismatches can completely abolish inhibition of gene expression. The presence of even a single base mismatch in one hairpin duplex strand allows differential inhibition of sense and antisense target strands. Moreover, the presence of a single mismatch in a strand otherwise complementary to a non-targeted RNA allows inhibition of the desired target RNA that is highly homologous to a non-targeted RNA, without inhibiting the non-targeted RNA. Preferably, the location of a mismatched base is near the center of the strand of the siRNA.

The presence of at least one mismatch in a strand of a hairpin siRNA results in increased strand specificity; such specificity provides advantages of reduced self-targeting of vectors expressing siRNAs. For example, hairpin siRNAs designed with strand specificity permits the inclusion of strand specific hairpin siRNAs in retroviral vectors containing a U6 promoter without self-targeting of the viral genomic RNA. Moreover, the presence of at least one mismatch results in a hairpin siRNA which can preferentially inhibit one strand of a target gene; this also indicates that base pairing within the hairpin siRNA duplex need not be perfect to trigger inhibition. Preferably, at least one mismatch is in a sense strand which otherwise is complementary to an antisense strand. A hairpin siRNA can also comprise at least two mismatches in a sense strand. If more than one mismatched base is present in a single strand, the two mismatched bases need not be contiguous; preferably, the bases are contiguous.

The presence of one or two mismatches in the sense strand also facilitates sequencing the hairpin siRNAs. Some perfect duplex hairpin siRNAs cannot be sequenced with standard automated sequencing methods; this appears to depend upon both the specific sequence and the GC content.

An embodiment of a hairpin siRNA with a single base mismatch (in the sense strand) is shown below, where R=non-paired base (SEQ ID NO:9)

Multi-inhibition siRNA: A Single Hairpin siRNA with Multiple Targets

In yet other embodiments, the present invention provides a composition comprising an siRNA, where the siRNA targets more than one gene, or more than one target in a single gene; such an siRNA is also referred to as a multi-target siRNA. Note that in the following description, the source of the target RNA" can be different genes, or different sections of a single gene, or a combination of either or both.

Generally, these embodiments utilize shared identical sequences of different target RNAs, or nearly identical sequences with non-standard base pairing of siRNA with different target RNAs, or overlapping antisense sequences in the siRNA such that the antisense sequence targets different RNA expressed from different genes, or a combination of any or all of these strategies. In other embodiments, an siRNA comprises more than one non-overlapping antisense sequence; these embodiments may also utilize a combination of any or all of the strategies involving shared identical sequences of different target RNAs, or nearly identical sequences with non-standard base pairing of siRNA with different target RNAs, or overlapping antisense sequences in the siRNA to different target RNAs. In some embodiments, the siRNA is a hairpin siRNA according to any of the embodiments described above.

In some embodiments, the siRNA antisense strand utilizes non-standard Watson-Crick base pairing in at least one base pair to hybridize to at least one of at least two different target RNAs. In standard Watson-Crick base pairing in RNA duplexes, U pairs with A, and G pairs with C. Thus, for a target RNA sequence of UAGC, the antisense siRNA sequence is AUCG. However, many non-standard Watson-Crick base pairs can exist for RNA duplexes, of which the most common include GU, UU, and GG, with GU reportedly being the most common naturally occurring non-standard base pair (Nagaswamy, U et al. (2002) Nucleic Acids Res 30(1):395-397; referring to non-canonical base-base interactions in secondary and tertiary RNA structures, of which known occurrences are tabulated in the NCIR database; and Kierzek, R et al. (1999) Biochem 38: 14214-14223) Thus, the presence of a G in an siRNA antisense strand could pair with either a C (in a standard base pair) or a U (in a non-standard base pair) in a target RNA strand. Therefore, for example, it is contemplated that two different target RNA strands, encoded by different DNA sequences, which share an identical target sequence of from about 19 to about 29 nucleotides except that they differ in at least one position (a non-identical position), where in one target sequence in the target RNA the non-identical position is occupied by a C and in the other target sequence in the target RNA the same non-identical position is occupied by a U, can be targeted by a single siRNA which is complementary to the shared target sequence of about 19 to about 29 nucleotides, where the siRNA antisense strand has a G at the position complementary to the non-identical positions occupied by the C or the U of the target sequences of the target RNAs. In other embodiments, the non-identical position in the target sequence of the target RNAs is occupied by an A or by a U, where the target RNAs are targeted by a single siRNA which is complementary to the target sequence, and where the siRNA antisense strand has a U at the position complementary to the non-identical position occupied by the A or the U of the target sequence of the target RNAs. In yet other embodiments, the non-identical position in the target sequence of the target RNAs is occupied by a C or by a G, where the target RNAs are targeted by a single siRNA which is complementary to the target sequence, where the siRNA antisense strand has a G at the position complementary to the non-identical position occupied by the C or the G of the target sequence of the target RNAs.

In further embodiments, in which an siRNA antisense strand utilizes non-standard Watson-Crick base pairing with a target RNA as described above, a first target RNA comprises more than one non-identical position with a second target RNA within an otherwise identical shared target sequence of from about 19 to about 29 nucleotides present in both target RNAs. It is contemplated that both the first and second non-identical position in the target sequence of the first target RNA may be occupied by the same nucleotide, or they may be occupied by different nucleotides, as long as these nucleotides and the comparable nucleotides in the target sequence of the second target RNA in the comparable non-identical positions are capable of forming either a standard or a non-standard base pair with the nucleotides in an siRNA antisense strand at the comparable non-identical positions. For example, the nucleotides in the first and second non-identical positions in the target sequence of the first target RNA can both be a C, and the nucleotides in the first and second non-identical positions in the target sequence of the second target RNA can both be a U, where the siRNA antisense strand has a G in the positions complementary to the first and second non-identical positions. Alternatively, the nucleotide in the first and second non-identical positions in the target sequence of the first target RNA can both be a C and a U, respectively, and the nucleotides in the first and second non-identical positions in the target sequence of the second target RNA can be a U and a C, respectively, where the siRNA antisense strand has a G in the positions complementary to the first and second non-identical positions. Other combinations are also contemplated, as long as the nucleotide in the siRNA antisense strand is capable of forming a standard or a non-standard base pair with the nucleotide present in each non-identical position of the target sequence of each target RNA.

In yet further embodiments, in which an siRNA antisense strand utilizes non-standard Watson-Crick base pairing with a target sequence of a target RNA, three target RNAs share an identical target sequence of from about 19 to about 29 nucleotides, except that that a first and a second target RNA differ in at least one position (a first non-identical position), and the first and a third target RNA differ in at least one position (a second non-identical position), which may or may not be the same as the first non-identical position. Various base pairings are contemplated as described above, as long as the nucleotide in the siRNA antisense strand is capable of forming a standard or a non-standard base pair with the nucleotide present in each non-identical position of each target sequence of each target RNA. In this way, a single siRNA can target three different genes.

In other embodiments, an siRNA targets at least two different genes at a shared identical target sequence. In these embodiments, it is contemplated that different target RNA strands, encoded by different DNA sequences, share an identical target sequence of from about 19 to about 29 nucleotides, which is the target of an siRNA which comprises a complementary or antisense strand to this identical target sequence. It is preferable that this shared identical sequence be unique to the target RNAs.

In other embodiments, an siRNA targets at least two different genes where the target sequences in the target RNAs are different but overlap at a region of shared identical sequence homology. In these embodiments, the target sequences share a region of identical sequence homology with each other, and each further comprises a contiguous region of non-homologous sequences, such that the total length of the homologous and non-homologous regions of all the target sequences is no longer than about 29 nucleotides long, where the total length comprises the length of the homologous region plus the length of each non-homologous region, and where the siRNA antisense strand is longer than each target sequence such that each target sequence is complementary to a portion of an siRNA antisense strand. Typically, the non-homologous region of a first target sequence is located at the opposite end of the non-homologous region of a second target sequence. For example, a first target sequence may comprise, from 3' to 5', a non-homologous region of about 6 nucleotides and a homologous region of about 14 nucleotides, and a second target sequence may comprise, from 3' to 5', the homologous region of the about 14 nucleotides and a second non-homologous region of about 6 nucleotides, such that the total length of the homologous and non-homologous regions is about 28 nucleotides long, and where each target sequences is complementary to a 20 nucleotide portion of an siRNA antisense strand of about 28 nucleotides long. The length of the two non-homologous regions need not be the same. It is contemplated that, within the parameters described above, the length of the homologous sequence region varies but is typically less than about 18 nucleotides long, and the length of the non-homologous sequence regions vary but are typically at least about one nucleotide long.

In yet other embodiments, an siRNA targets more than two different genes by a combination of any or all of the embodiments described above. For example, it is contemplated that two different target RNA strands share an identical target sequence of from about 19 to about 29 nucleotides, which is the target of an siRNA which comprises a complementary or antisense strand to this identical target sequence, and moreover, that a third different target RNA strand shares the same identical target sequence except that it differs in at least one position (a non-identical position), which is occupied by a nucleotide which can form a non-standard base pair with the nucleotide in the siRNA antisense strand in the comparable position.

In yet other embodiments, an siRNA comprises at least two different non-overlapping antisense sequences. Each antisense sequence is from about 18 to about 29 nucleotides long. The antisense sequences may be adjacent to each other in one strand of an siRNA; in these embodiments, the antisense sequences may be contiguous, or they may be separated from each other by from about one to several nucleotides. In alternative embodiments, for an siRNA comprising two antisense sequences, the antisense sequences are on separate strands of an siRNA; in these embodiments, a typical arrangement would be antisense sequence 1-sense sequence 2-loop-antisense sequence 2-sense sequence 1, where antisense sequence 1 is substantially complementary to sense sequence 1, and antisense sequence 2 is substantially complementary to sense sequence 2. The opposite arrangement is also contemplated, which is sense sequence 1-antisense sequence 2-loop-sense sequence 2-antisense sequence 1. In embodiments where one antisense sequence is adjacent to a sense sequence for a second or different antisense sequence, the two adjacent sequences may be contiguous, or they may be separated by from about one to several nucleotides. Similar variations are contemplated for siRNAs comprising more than two antisense sequences. A combination of an antisense sequence/sense sequence duplex region can be considered an "inhibitory module." Thus, in different embodiments, an siRNA comprises at least two inhibitory modules, as described above. In any of the embodiments, from none to all of the nucleotides in the loop may be part of an antisense sequence. It is further contemplated that any of the antisense sequences may also comprise a set of two overlapping antisense sequences against two different target RNAs. It is also contemplated that any of the duplex regions comprising at least a portion of an antisense sequence may further comprise at least one mismatch or non-standard base pairing, as described above. In some embodiments, a processing signal is incorporated into an antisense sequence, such that a duplex region comprising at least one antisense sequence is cleaved from the siRNA; typically, a processing signal is at or near one end of an antisense sequence. In some embodiments, a processing signal is incorporated into an inhibitory module, such that a duplex region comprising at least one inhibitory module is cleaved from the siRNA; typically, a processing signal is at or near one end of an inhibitory module. Exemplary processing signals are contemplated to include but not be limited to a mismatch comprising at least one missing base in one strand, where the missing base is at or near the end of an antisense sequence or inhibitory module, and results in the presence of a bubble in the opposite strand. In some of these embodiments, the presence of the bubble is a signal to cleave a duplex region at or near the bubble, resulting in a separate duplex region comprising an antisense sequence, or an inhibitory module.

With these embodiments, it is possible to target more than one RNA target with a single siRNA. Thus, a multi-target siRNA targets more than one gene, or more than one target in a single gene. In some embodiments, a pair of genes is targeted by a single siRNA. In other embodiments, three or more genes are targeted by a single siRNA. In other embodiments, more than one region of a target RNA is targeted by a single siRNA; in these embodiments, it is contemplated that more complete inhibition of gene function will result. In other embodiments, a combination of more than one target in a single gene and more than one gene are targeted by a single siRNA. In any of these embodiments, the siRNA is a hairpin RNA, as described above.

Multiplex Hairpin siRNAs

In yet other embodiments, the present invention provides a composition comprising a single complex comprising two or more siRNAs. Such a complex is referred to as a multiplex of more than one siRNA. Preferably, the siRNA in the multiplex comprises one or more hairpin siRNAs. Each hairpin siRNA is any of the hairpin siRNAs described above, and may or may not possess strand selectivity, as described above. Each hairpin siRNA is joined by a linker to at least one other hairpin siRNA. In some embodiments, the linker comprises non-nucleotide linkers. In other embodiments, the linker is an RNA sequence (a joining sequence). The joining sequence comprises at least one, and preferably three or more, nucleotides. The joining sequence nucleotides may be unpaired, or some of the nucleotides may be paired, resulting in a joining sequence with regions of paired nucleotides or other three-dimensional structure. The joining sequence may possess cleavage sites, resulting in separation of the multiplex structure into at least two parts. In some embodiments, the multiplex hairpin siRNA comprises two hairpin siRNAs, with a joining sequence linking the 3' end of one hairpin siRNA to the 5' end of the other hairpin siRNA. In other embodiments, the multiplex hairpin siRNA comprises three hairpin siRNAs, with a first joining sequence linking the 3' end of a first hairpin siRNA to the 5' end of a second hairpin siRNA, and a second joining sequence linking the 3' end of a second siRNA hairpin to the 5' end of a third hairpin siRNA.

A multiplex comprising two or more siRNAs may target different sections of the same gene, or different genes, or both.

Other Design Considerations

Several additional considerations are useful in designing hairpin siRNAs with optimal performance. No more than three consecutive U nucleotides should be present anywhere within an siRNA hairpin sequence when expressed from an RNA pol III promoter, as RNA pol III terminates at runs of four or more Ts in the DNA template. Templates should include four or more Ts (such as five Ts) at the 3' end for termination. A GC content in the 45-70% range is frequently used, though other GC contents, of for example, greater than 70% and less than 45%, are also contemplated. Checking for possible matching sequences in other genes or target gene sequence polymorphisms using an EST database is suggested.

B. Target Genes

A target gene is any gene that encodes RNA; the RNA may be mRNA, or it may be any other RNA susceptible to functional inhibition by siRNA. The target of the siRNA may be an endogenous gene, for which the function is either known or unknown, or an exogenous gene, such as a viral or pathogenic gene or a transfected gene. A known gene is one for which the coding sequence is known; the function of such a gene may be known or unknown. Endogenous genes include but are not limited to, for example, disease-causing genes, such as oncogenes, or genetic lesions or defects which result in a disabling conditions. Exogenous genes include but are not limited to reporter genes, marker genes, selection genes, and functional genes.

Particularly useful reporter genes include, but are not limited to, firefly luciferase, *Renilla* luciferase, β-gal, green fluorescent protein, chloramphenicol acetyltransferase, β-glucuronidase, alkaline phosphatase, secreted alkaline phosphatase, and human growth hormone. The origin of these genes, their protein characteristics, and the assay for their detection and quantitation are all well known. (See, for example, *Current Protocols in Molecular Biology* (1995), Chapter 9, "Introduction of DNA into Mammalian Cells," Section II, "Uses of Fusion Genes in Mammalian Transfection," (ed: Ausabel, F. M., et al.; John Wiley & Sons, USA), pp. 9.6.1-9.6.12). The latter two proteins are of particular interest, as they are secreted from transfected culture cells into the culture medium. Therefore, the amount of secreted protein can be quantitated from a small sample of the culture medium. However, human growth hormone is not an enzyme, and the protein must therefore be measured directly by an antibody-based assay.

C. Expression Cassette

Hairpin siRNAs of the present invention may be synthesized chemically; chemical synthesis can be achieved by any method known or discovered in the art (exemplary methods are provided in Example 1). Alternatively, hairpin siRNAs of the present invention may be synthesized by methods provided by the present invention, which comprise synthesis by transcription. In some embodiments, transcription is in vitro, as from a DNA template and bacteriophage RNA polymerase promoter, as described further below; in other embodiments, synthesis is in vivo, as from a gene and a promoter, as described further below. Separate-stranded duplex siRNA, where the two strands are synthesized separately and annealed, can also be synthesized chemically by any method known or discovered in the art (see Example 1). Alternatively, ds siRNA are synthesized by methods provided by the present invention, which comprise synthesis by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a siRNA. In some embodiments, the transcribed siRNA forms a single strand of a separate-stranded duplex (or double-stranded, or ds) siRNA of about 18 to 25 base pairs long; thus, formation of ds siRNA requires transcription of each of the two different strands of a ds siRNA. In other embodiments, the transcribed siRNA forms a hairpin siRNA, as described in any of the embodiments above. The hairpin siRNA is initially transcribed as a single RNA strand, which is contemplated to then fold into a hairpin structure. The initial RNA transcript may be processed before or after folding into a hairpin to form a mature hairpin structure; processing includes but is not limited to cleavage to remove at least one base from at least one position, addition of at least one nucleotide, and/or the addition or removal of phosphate groups. Thus, a gene encoding a hairpin siRNA may encode additional RNA bases or fragments that are not present in a mature, processed siRNA. Alternatively, a newly synthesized transcript of siRNA may fold into a partial hairpin siRNA as described above, to which at least one additional nucleotide is added.

The term "gene" in the expression cassette refers to a nucleic acid sequence that comprises coding sequences necessary for the production of a siRNA. Thus, a gene includes but is not limited to coding sequences for a strand of a ds siRNA, or for a hairpin siRNA. Such genes are referred to generically as "siRNA genes."

A DNA expression cassette comprises a chemically synthesized or recombinant DNA molecule containing at least one gene, or desired coding sequence for a single strand of a ds siRNA or for a hairpin siRNA as described above, and appropriate nucleic acid sequences necessary for the expression of the operably linked coding sequence, either in vitro or in vivo. Expression in vitro includes expression in transcription systems and in transcription/translation systems. Expression in vivo includes expression in a particular host cell and/or organism. Nucleic acid sequences necessary for expression in a prokaryotic cell or in a prokaryotic in vitro expression system are well known and usually include a promoter, an operator (optional), and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand. Exemplary expression cassettes, including a T7 promoter oligonucleotide and DNA oligonucleotide templates for T7 transcription, are provided in Example 1, FIG. 1, and FIG. 5. In some embodiments, 40 nucleotide DNA template oligonucleotides (or expression cassettes) are designed to produce 21-nt siRNAs. siRNA sequences of the form $GN_{17}CN_2$ are selected for each target, since efficient T7 RNA polymerase initiation requires the first nucleotide of each RNA to be G (Milligan, J. F. et al. (1987) *Nucleic Acids Res* 15, 8783-98). The last two nucleotides form the 3' overhang of the siRNA duplex and are changed to U for the sense strand (Elbashir, S. M. et al. (2001) *Nature* 411, 494-8). For hairpin siRNAs, only the first nucleotide needs to be G.

In any of the expression cassettes described above, the gene may encode a transcript that contains at least one cleavage site, such that when cleaved results in at least two cleavage products. Such products can include the two opposite strands of a ds siRNA, or two different hairpin siRNAs directed against the same or different target RNA sequences.

In an expression system suitable for expression in a eukaryotic cell, the promoter may be constitutive or inducible; the promoter may also be tissue or organ specific, or specific to a developmental phase. Preferably, the promoter is positioned 5' to the transcribed region; in one preferred embodiment, the promoter is the U6 gene promoter. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

D. Vectors

In other aspects of the present invention, the compositions comprise a vector comprising at least one expression cassette comprising a promoter and a gene which encodes a sequence necessary for the production of a siRNA (an siRNA gene), as described above; the vectors may further comprise marker genes, reporter genes, selection genes, or genes of interest, such as experimental genes. Vectors of the present invention include cloning vectors and expression vectors; expression vectors are used in in vitro transcription/translation systems, as well as in in vivo in a host cell. Expression vectors used in vivo in a host cell are transfected into a host cell, either transiently, or stably. Thus, a vector may also include sites for stable integration into a host cell genome.

In some embodiments, it is useful to clone a siRNA gene downstream of a bacteriophage RNA polymerase promoter into a multicopy plasmid; a variety of transcription vectors containing bacteriophage RNA polymerase promoters (such as T7 promoters) are available. Alternatively, DNA synthesis can be used to add a bacteriophage RNA polymerase promoter upstream of a siRNA coding sequence. The cloned plasmid DNA, linearized with a restriction enzyme, can then be used as a transcription template (See for example Milligan, J F and Uhlenbeck, O C (1989) Methods in Enzymology 180: 51-64).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements. Examples of U6 siRNA expression vectors, in which a mouse U6 promoter was cloned into the vector RARE3E, with an introduced Bbs1 site which allowed insertion of siRNA sequences at the first nucleotide of the U6 transcript, are provided in Example 1, FIG. 4, and FIG. 5. Note that these vectors express either a single strand of ds siRNA, or a hairpin siRNA. For vectors encoding a single strand of a ds siRNA, formation of ds siRNA in a cell requires co-transfection of a single cell with two vectors, each encoding one of the two strands; upon expression of the vectors, the two strands combine to form ds siRNA. Examples of co-transfection with two vectors, each encoding a single strand of a ds siRNA, are provided in Example 4; two vectors utilized included U6-BT4as and U6-BT4s vectors, which encoded complementary single stranded RNAs with 19 nucleotide corresponding to the sense ("s") or antisense ("as") strands of the BT4 ds siRNA directed against neuronal β-tubulin. In other embodiments, a single vector expresses both strands of a ds siRNA; in this vector, each coding sequence for a single strand of the ds siRNA may be under control of its own promoter (for example, a U6 promoter), or the two coding sequences may be encoded by a single sequence which has a cleavage site between the two strands and which is under control of a single promoter. An example of the former embodiment is provided in Example 4, in which a single vector encodes the two complementary strands of the BT4 ds siRNA directed against neuronal β-tubulin, each under control a U6 promoter, where each promoter-gene construct is located in tandem in the vector. In the latter embodiment, the single transcript is cleaved into two separate strands, which can then combine in vivo to produce a ds siRNA.

In certain embodiments of the present invention, a gene sequence in an expression vector which is not part of an expression cassette comprising a siRNA gene is operatively linked to an appropriate expression control sequence(s) (promoter) to direct mRNA synthesis. In some embodiments, the gene sequence is a marker gene or a selection gene. Promoters useful in the present invention include, but are not limited to, the cytomegalovirus (CMV) immediate early, herpes simplex virus (HSV) thymidine kinase, and mouse metallothionein-I promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of DNA encoding a gene is increased by inserting an enhancer sequence into the vector. Enhancers are cis-acting elements of DNA, usually about from 10 to 300 bp that act on a promoter to increase its transcription. Enhancers useful in the present invention include, but are not limited to, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

Exemplary vectors include, but are not limited to, the following eukaryotic vectors: pWLNEO, pSV2CAT, pOG44, PXT1, pSG (Stratagene) pSVK3, pBPV, pMSG, pSVL (Pharmacia), and pCS2 vectors and its derivatives, as described in the Examples. Other plasmids are the Adenovirus vector (AAV; pCWRSV, Chatterjee et al. (1992) Science 258: 1485), a retroviral vector derived from MoMuLV (pG1Na, Zhou et al. (1994) Gene 149: 3-39), and pTZ18U (BioRad, Hercules, Calif., USA). Particularly useful vectors comprise U6 promoters, as described in the Examples.

E. Transfected Cells

In yet other aspects, the present invention provides compositions comprising cells transfected by an expression cassette of the present invention as described above, or by a vector of the present invention, where the vector comprises an expression cassette of the present invention, as described above. In some embodiments of the present invention, the host cell is a mammalian cell. A transfected cell may be a cultured cell or a tissue, organ, or organismal cell. Specific examples of cultured host cells include, but are not limited to, Chinese hamster ovary (CHO) cells, COS-7 lines of monkey kidney fibroblasts, (Gluzman, Cell 23:175 (1981)), 293T, C127, 3T3, HeLa and BHK cell lines. Specific examples of host cells in vivo include tumor tissue. Exemplary transfected cells are mouse P19 cells, as described in Example 1.

The cells are transfected transiently or stably; the cells are also transfected with an expression cassette of the present invention, or they are transfected with an expression vector of the present invention. In some embodiments, transfected cells are cultured mammalian cells, preferably human cells; in other embodiments, they are tissue, organ, or organismal cells.

F. Kits

The present invention also provides kits comprising at least one expression cassette comprising a siRNA gene. In some aspects, a transcript from the expression cassette forms a double stranded siRNA of about 18 to 25 base pairs long. In other embodiments, the transcribed siRNA forms any of the hairpin siRNAs as described above. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a siRNA gene, such that at least one gene encodes one strand of a siRNA that combines with a strand encoded by a second cassette to form a ds siRNA; the ds siRNA so produced is any of the embodiments described above. These cassettes thus comprise a promoter and a sequence encoding one strand of a ds siRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a ds siRNA and a processing site between the sequences encoding each strand such that, when the gene is transcribed, the transcript is processed, such as by cleavage, to result in two separate strands which can combine to form a ds siRNA, as described above.

III. Methods

The present invention also provides methods of synthesizing siRNAs. The siRNAs are synthesized in vitro or in vivo. In vitro synthesis includes chemical synthesis, and by methods of the present invention, synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The siRNAs synthesized in vitro, either chemically or by transcription, are used to transfect cells, as described below. Therefore, the present invention also provides methods of transfecting host cells with siRNAs synthesized in vitro; in particular embodiments, the siRNAs are synthesized by in vitro transcription. The present invention further provides methods of silencing genes in vivo by transfecting cells with siRNAs synthesized in vitro. In other embodiments, the present invention provides methods of silencing genes in vitro, by using in vitro synthesized siRNAs in test systems, as for example to examine the efficacy of a siRNA in silencing expression of a gene, where the gene is a reporter gene expressed in a transcription and/or translation system and the siRNAs are added to the expression system. In other methods, the siRNAs is expressed in vitro in a transcription/translation system from an expression cassette or expression vector, along with an expression vector encoding and expressing a reporter gene.

The present invention also provides methods of expressing siRNAs in vivo by transfecting cells with expression cassettes or vectors which direct synthesis of siRNAs in vivo. The present invention also provides methods of silencing genes in vivo by transfecting cells with expression cassettes or vectors that direct synthesis of siRNAs in vivo; target genes are described above.

A. Synthesis of siRNA by In Vitro Transcription

The present invention provides methods of synthesis of siRNA by in vitro transcription. In some embodiments, siRNA is synthesized in vitro by transcription from a DNA template and a bacteriophage RNA polymerase promoter, where either ds siRNA or hairpin siRNA is synthesized.

In vitro transcription includes transcription by bacteriophage RNA polymerases such as T3, T7, and SP6 by methods well known in the art (as for example is described by Milligan, J F and Uhlenbeck, O C (1989) Methods in Enzymology 180: 51-64) from an expression cassette. For use in such systems, an expression cassette comprises a DNA template and an RNA-dependent polymerase promoter region for in vitro transcription by a bacteriophage RNA polymerase, as described above. The RNA transcripts can be purified after synthesis, to remove undesirable products.

Synthesis of hairpin siRNA is achieved by transcription from an expression cassette, as described above; the siRNA transcript is contemplated to fold into a hairpin structure during or after synthesis.

Synthesis of separate-stranded duplex siRNA is achieved by synthesizing the two strands separately. In some embodiments, the two strands are encoded by different expression cassettes, as described above, and annealed after synthesis by transcription; in other embodiments, the two strands of the double-stranded region of a siRNA are expressed separately from two different expression vectors, as described above, and then annealed.

Exemplary methods of the present invention for the synthesis of siRNA by in vitro transcription are provided in Example 1. In these methods, each template and a 20-nt T7 promoter oligonucleotide are mixed in equimolar amounts, heated for 5 min at 95° C., then gradually cooled to room temperature in annealing buffer (10 mM Tris-HCl and 100 mM NaCl). In vitro transcription is then carried out using the AmpliScribe T7 High Yield Transcription Kit (Epicentre, Madison, Wis.) with 50 ng of oligonucleotide template in a 20 µl reaction for 6 hours or overnight. RNA products are purified by QIAquick Nucleotide Removal kit (Qiagen, Valencia, Calif.). For annealing of siRNA duplexes, siRNA strands (150-300 ng/µl in annealing buffer) are heated for 5 min at 95° C., then cooled slowly to room temperature. Short RNA products are produced during in vitro transcription reactions (Booth, B. L., Jr. & Pugh, B. F. (1997) *J Biol Chem* 272, 984-91), and have been observed by the inventors to sometimes reduce transfection efficiency; therefore, siRNA duplexes and hairpin siRNAs are optionally further gel purified using 4% NuSieve GTG agarose (BMA, Rockland, Me.). RNA duplexes are identified by co-migration with a chemically synthesized RNA duplex of the same length, and recovered from the gel by β-agarase digestion (New England Biolabs, Beverly, Mass.). Other embodiments utilize any known or discovered methods of in vitro transcription (see, for example, Milligan, J. F. et al. (1987) *Nucleic Acids Res* 15, 8783-98; and Milligan, J F and Uhlenbeck, O C (1989) Methods in Enzymology 180: 51-64).

In other embodiments, siRNA is synthesized by in vivo transcription from an expression cassette as described above or from an expression vector as described above, in any in vitro transcription and/or translation system which is known or developed. Exemplary transcription/translation systems include but are not limited to reticulate lysate sand wheat germ agglutinin systems, and TnT (Promega, Madison, Wis.).

B. Synthesis of siRNA by In Vivo Transcription

In other embodiments, the present invention provides a method for transcription of siRNA in vivo, where either ds siRNA or hairpin siRNA is synthesized. Synthesis in vivo involves transfection of a suitable expression vehicle, such as an expression vector encoding a siRNA gene as described above, into a host cell, where the encoded siRNA gene is expressed. Therefore, the present invention also provides methods of transfecting a host cell with an expression cassette or with an expression vector as described above. The present invention also provides methods of expressing siRNA in a host cell by transfecting the cell with an expression cassette or with an expression vector as described above. The present invention also provides methods of silencing a gene in a host cell by transfecting the cell with an expression cassette as described above or with an expression vector as described above, where a siRNA encoded by the expression cassette targets a gene. In different embodiments of any of these methods, the cell is transfected either transiently or stably, and in some embodiments, the cell is a cultured mammalian cell, preferably a human cell, or it is a tissue, organ, or organismal cell. Moreover, in different embodiments of these methods, the target of a siRNA is an endogenous gene, an exogenous gene, such as a viral or pathogenic gene or a transfected gene, or a gene of unknown function.

In other embodiments, the present invention provides a method for inhibiting gene expression while concomitantly expressing a visible or selectable marker, wherein the marker DNA harbors an miRNA precursor molecule in an intron. Thus, a single construct expresses both the siRNA and the marker gene. In another embodiment, the present invention provides a method for the identification and selection of cells expressing different levels of an exogenous siRNA, based on determination of the level of a coexpressed visible or selectable marker that harbors the siRNA in an intron. In still another embodiment, the present invention provides a method for inhibiting expression of a deleterious endogenous gene by siRNA, while simultaneously expressing an improved version of that gene that is also siRNA inhibition-resistant.

Furthermore, in different embodiments of the methods, a transcript from a siRNA gene in an expression cassette or in an expression vector forms a hairpin siRNA, as described above, or forms a ds siRNA, as described above. In some embodiments in which encoded siRNA forms a ds siRNA, two complementary strands of the double-stranded region of the siRNA are expressed separately by two different expression cassettes or by two different expression vectors, as described above, which are co-transfected into a host cell; the two different strands then form a duplex in the cell. An illustration of co-transfection with two vectors, each encoding a single strand of a ds siRNA, is provided in Example 4, where the two vectors utilized included U6-BT4 as and U6-BT4s vectors, which encoded complementary single stranded RNAs with 19 nucleotide corresponding to the sense ("s") or antisense ("as") strands of the BT4 ds siRNA directed against neuronal β-tubulin.

In other embodiments, two complementary strands of a double-stranded region of a ds siRNA are encoded by a single expression cassette or vector, as described above. When the coding sequence for each strand is under control of its own promoter, expression of the transfected cassette or vector results in the synthesis of the two complementary strands, which then form a duplex in the transfected cell. An illustration of this embodiment is provided in Example 4, in which a vector in which the two complementary strands of the BT4 ds siRNA directed against neuronal β-tubulin were expressed from tandem U6 promoters on a single plasmid. Alternatively, when each strand is encoded by a single sequence comprising the two coding sequences linked by a processing site under control of a single promoter (described above), expression of the transfected cassette or vector results in the synthesis of single strand, which is then processed to form two single strands which then form a duplex in the transfected cell.

Thus, any of the vectors described above can be used for cell transfection and in vivo expression of an encoded siRNA.

C. Transfection

The compositions and methods of the present invention are applicable to situations in which short-term effects of siRNA are to be examined in vitro; such effects are observed by adding synthetic siRNA or by expressing siRNA intracellularly. In situations in which long-term effects of siRNA are to be examined, it is preferable and in fact necessary to utilize intracellular expression of siRNA. Moreover, it is also necessary to use intracellular expression of siRNA for in vivo effects, as in gene therapy and research applications.

In the present invention, cells to be transfected in vitro are typically cultured prior to transfection according to methods which are well known in the art, as for example by the preferred methods as defined by the American Tissue Culture Collection or as described (for example, Morton, H. J., *In Vitro* 9: 468-469 (1974). Exemplary culture conditions are provided in Example 1; in these methods, mouse P19 cells (Davis, R. L. et al. (2001) *Dev Cell* 1, 553-65) are first cultured as described (Rupp, R. A. et al. (1994) *Genes Dev* 8, 1311-1323); then for transfection, cells are plated on dishes coated with murine laminin (Invitrogen, Carlsbad, Calif.) at 70-90% confluency without antibiotics. When cells to be transfected are in vivo, as in a tissue, organ, or organism, the cells are transfected under conditions appropriate for the specific organ or tissue in vivo; preferably, transfection occurs passively. In different embodiments of the present invention, cells are transfected with siRNAs that are synthesized exogenously (or in vitro, as by chemical methods or in vitro transcription methods), or they are transfected with expression cassettes or vectors (described above), which express siRNAs within the transfected cell.

In some embodiments, cells are transfected with siRNAs by any means known or discovered in the art which allows a cell to take up exogenous RNA and remain viable; non-limiting examples include electroporation, microinjection, transduction, cell fusion, DEAE dextran, calcium phosphate precipitation, use of a gene gun, osmotic shock, temperature shock, and electroporation, and pressure treatment. In alternative, embodiments, the siRNAs are introduced in vivo by lipofection, as has been reported (as, for example, by Elbashir et al. (2001) Nature 411: 494-498) and as described in more detail below. Exemplary methods for transfection of cells with siRNA by lipofection are provided in Example 1; in these methods, transfections are performed with Lipofectamine 2000 (Invitrogen) as directed by the manufacturer.

In other embodiments expression cassettes or vectors comprising at least one expression cassette, as described above, are introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267:963; Wu and Wu (1988) J. Biol. Chem., 263:14621; and Williams et al. (1991) Proc. Natl. Acad. Sci. USA 88:272). Receptor-mediated DNA delivery approaches are also used (Curiel et al. (1992) Hum. Gene Ther., 3:147; and Wu and Wu (1987) J. Biol. Chem., 262:4429).

In some embodiments, various methods are used to enhance transfection of the cells. These methods include but are not limited to osmotic shock, temperature shock, and electroporation, and pressure treatment. In pressure treatment, plated cells are placed in a chamber under a piston, and subjected to increased atmospheric pressures (for example, as described in Mann et al., Proc Natl Acad Sci USA 96: 6411-6 (1999)). Electroporation of the cells in situ following plating may be used to increase transfection efficiency. Plate electrodes are available from BTX/Genetronics for this purpose.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. (1987) Proc. Natl. Acad. Sci. USA 84:7413-7417; See also, Mackey, et al. (1988) Proc. Natl. Acad. Sci. USA 85:8027-8031; Ulmer et al. (1993) Science 259:1745-174). The use of cationic lipids may promote encapsulation of negatively charged nucleic acids, and also promote fusion with negatively charged cell membranes (Felgner and Ringold (1989) Science 337:387-388). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a sequence encoding a siRNA in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure; typically, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

D. Detection of Inhibition of Gene Expression or Inhibition of RNA Function

The effectiveness of siRNA in vitro, as in a test system, or in a cell can be determined by measuring the degree of inhibition of gene expression (or gene silencing) or inhibition of RNA function. Both gene silencing and inhibition of RNA function can be monitored by a number of similar means. A "silenced" gene, or inhibition of gene expression, and inhibition of RNA function, are evidenced by the disappearance of the RNA, or less directly by the disappearance of a protein translated from the RNA where the gene or RNA encode a protein product. For endogenous protein coding genes, rapid protein turnover allows monitoring of gene silencing by protein disappearance; slower protein turnover may be better monitored by measuring mRNA. For exogenous genes, measuring either RNA or protein disappearance would be appropriate.

Detection of the loss of RNA is a more direct measure of both gene silencing and inhibition of RNA function than is detection of protein disappearance for genes and RNA which encode proteins, as it avoids possible artifacts that may be the results of downstream processing. RNA can be detected by Northern blot analysis, ribonuclease protection assays, or RT-PCR. However, measurement of RNA is cumbersome. Moreover, if the objective is to determine the function of a gene or the function of the gene product where the gene encodes a protein, then eliminating the presence of the protein is the a preferred initial step in determining gene function. Therefore, in many embodiments, preferred assays measure the presence or amount of a gene protein product for protein encoding genes.

Proteins can be assayed indirectly by detecting endogenous characteristics, such as enzymatic activity or spectrophotometric characteristics, or directly by using antibody-based assays. Enzymatic assays are generally quite sensitive due to the small amount of \enzyme required to generate the products of the reaction. However, endogenous enzyme activity will result in a high background. Antibody-based assays are usually less sensitive, but will detect a gene protein whether it is enzymatically active or not.

Exemplary methods of detecting gene silencing are provided in Example 1; these methods include assaying a reporter gene (for example luciferase) by measuring the activity of the expressed protein, and assaying an endogenous gene (for example tubulin) by antibody staining and immunohistochemistry.

E. Test Systems

In other embodiments, the present invention provides methods of silencing genes in vitro, by using in vitro synthesized siRNAs in test systems, as for example to examine the efficacy of a siRNA in silencing expression of a gene, where the gene is a reporter gene expressed in a transcription and/or translation system and the siRNAs are added to the expression system. In other methods, the siRNAs is expressed in vitro in a transcription/translation system from an expression cassette or expression vector, along with an expression vector encoding and expressing a reporter gene.

Exemplary test systems include but are not limited to in vitro transcription/translation systems such as reticulocyte lysate and wheat germ agglutinin lysate. Other systems include siRNA mediation of RNAi in *Drosophila melanogaster* embryo lysate (Elbashir et al. (2001) The EMBO J. 20(23): 6877-6888) and lysates of cultured *Drosophila* S2 cells (Hammond, S. M. et al. (2000) Nature 404: 293-298).

In vitro synthesis of siRNAs, expression cassettes and vectors, and target genes are described above, as are methods of detecting gene silencing or inhibition of RNA function.

F. Target Strategies

In some embodiments, a single siRNA is directed against two or more genes that share sufficient sequence homology such that a single siRNA can inhibit expression of these genes. This is particularly useful for homologous genes, as for example in mammalian systems, which contain long stretches of identical sequences; such genes may be members of a gene family. In these embodiments, a single siRNA can recognize several members of a gene family.

In other embodiments, a single siRNA is directed against a single gene. In these cases, siRNA is directed against a unique sequence found only in the target gene.

In other embodiments, siRNA is used in conjunction with gene replacement, in which the function of a silenced gene is restored. Examples of restoration include adding a gene encoding the same protein but with a slightly different sequence, by using codon wobble to change the nucleotide at the third base position in the codon. Restoration is particularly useful when several homologous genes are known, but the different function of the different family member is not known.

In other embodiments, siRNA is present in a multiplex structure that comprises two or more siRNAs, as described above. The siRNAs in a multiplex structure are directed against different regions of a target single gene, against different target genes, or both. The target genes are endogenous genes or exogenous genes or both genes. In other embodiments, multiple siRNAs are used in a test system, as described above, or transfected into a cell, as described above, simultaneously; transfected siRNA is synthesized in vitro or in vivo, as described above. The multiple siRNAs are directed against different regions of a target single gene, against different target genes, or both. The target genes are endogenous genes or exogenous genes or both genes. The use of multiplex structures or multiple siRNAs simultaneously allows coordinate targeting of multiple components of a pathway (for example, a signal transduction pathway). The use of multiplex structures is contemplated to provide an effective therapeutic approach, as for example only one structure need be incorporated into or expressed in a test system or in a cell. The use of multiplex structures is also contemplated to provide a powerful research tool to understand cellular metabolic and other biochemical and physiologic pathways, as for example only one structure need be incorporated into or expressed in a test system or in a cell.

IV. Applications

The ability to inhibit gene function by RNAi using siRNAs synthesized in host cells is contemplated to have broad application. In some embodiments, this approach should facilitate studies of gene function in transfectable cell lines. In other embodiments, this approach is adaptable to situations for which delivery of in vitro synthesized siRNAs by transfection may not be practical, such as primary cell cultures, studies in intact animals, and gene therapy (ex vivo and in vivo).

Previous results with siRNA suggest that intracellular expression of siRNA against a wide variety of targets will be effective at reducing or eliminating expression of the targets. In some embodiments of the present invention, an expression cassette is used in combination with different recombinant DNA vectors to target different cell populations. It is contemplated that either one or more than one expression cassettes are inserted in a vector (the cassettes are relatively small); the siRNA encoded by the expression cassette is directed either to the same target (different stretches of RNA on the same target RNA) or to entirely different targets (e.g., multiple gene products of a virus). It is further contemplated that this method of expressing siRNAs from various expression gene cassettes is useful in both experimental and therapeutic applications. Experimental applications include the use of the compositions and methods of the present invention to the field of reverse genetic analysis of genes found in the human genome sequence. Therapeutic applications include the use of the compositions and methods of the present invention as antiviral agents, antibacterial agents, and as means to silence undesirable genes such as oncogenes.

A. Research Applications

The compositions and methods of the present invention are applicable to the field of reverse genetic analysis, by gene silencing. In some embodiments, the present inventions provides methods for in vitro synthesis of siRNA, of either ds siRNA or hairpin siRNA, by in vitro transcription; such methods provide efficient and economical alternatives to chemical synthesis, and the siRNAs so synthesized can be used to transfect cells. In other embodiments, a siRNA construct (for either ds siRNA or hairpin siRNA) can be designed to silence a gene of unknown function, inserted into at least one expression cassette, and transfected into the cell in which the target gene is expressed. The effect of the lack of or disappearance of an expressed gene product in the transfected cell can then be assessed; such results often lead to elucidation of the function of the gene. Application of siRNA to genes of known function is also contemplated to further examine the effects of the absence of the targeted gene function in a transfected cell.

In some embodiments, research applications are in vivo in cells or tissues, as when cultured cells or tissues are transfected with either synthetic siRNA or siRNA expression constructs, as described above. In other embodiments, research applications are in vivo, as when organisms such as mammals are transfected with siRNA expression constructs, as described in further detail below.

In other embodiments, siRNAs are used in high throughput screening. In these embodiments, the effects of libraries of siRNAs are screened for gene involvement in a particular process, for example in a known process. The siRNAs are either synthesized in vivo, from expression cassettes or vectors, or in vitro, from expression cassettes or vectors or chemically. Screening is done in vitro, or preferably in vivo, in transfected cells. Thus, in some embodiments, cells are transfected with a collection or library of siRNAs or with a collection or library of expression vectors encoding siRNA, and the effects of the siRNA determined; preferably, the siRNA is a hairpin siRNA of the present invention.

In some embodiments, the target gene confers a readily perceived phenotype upon the mammal. In these embodiments, a siRNA expression cassette is designed to target the gene for the phenotype. The expression cassette is injected directly into mammalian embryos, and the embryos implanted into a surrogate female parent by well known techniques. Expression of the siRNA gene results in a phenotype displayed in patterns (because the gene is injected into an embryo, as opposed to a fertilized egg, the result is an individual composed of a mosaic of cells, some of which are transfected with the siRNA gene). The expression of the siRNA gene is confirmed by PCR analysis, and the transgenic mosaic individuals are bred to produce homozygous individuals. This procedure greatly reduces the amount of time required to produce a knock-out line of mammals, which depending upon the mammal, may be decreased by from about fifty percent to ninety percent or more.

In particular embodiments of the present invention, the U6 siRNA expression cassette exemplified herein is small (<400 nt), and is suitable for delivery into cells by DNA based viral vectors (20, 33 Tazi, J. et al. (1993) Mol Cell Biol 13, 1641-50; and Potter, P. M. et al. (2000) Mol Biotechnol 15, 105-14). The ability to design hairpin siRNAs with strand specificity also permits the inclusion of hairpin siRNAs in retroviral vectors containing a U6 promoter (Ilves, H. et al. (1996) Gene 171, 203-8) without self-targeting of the viral genomic RNA. In some embodiments, the combination of a marker gene and one (or more) U6 hairpin expression cassettes in a viral vector facilitate single-cell or mosaic analysis of gene function. In other embodiments, the combination includes a single expression cassette directing the synthesis of a single strand of RNA containing multiple hairpin siRNAs, each targeted to a separate gene; the separate hairpin siRNAs may further be cleavable from the initially synthesized RNA strand. This is particularly useful for tissue or stage specific analysis of genes with broad roles in development. In particular embodiments, the methods and compositions of the present invention are applied to studies of neurogenesis and differentiation in mammals; these embodiments are supported by the observations that it is possible to inhibit a neuron specific gene in a model system for neuronal differentiation, as described in Examples 1, 4 and 5.

B. Therapeutic Applications

The present invention also provides methods and compositions suitable for gene therapy to alter gene expression, production, or function. As described above, the present invention provides compositions comprising expression cassettes comprising a gene encoding a siRNA, and vectors comprising such expression cassettes. The methods described below are generally applicable across many species.

Viral vectors commonly used for in vivo or ex vivo targeting and therapy procedures are DNA-based vectors and retroviral vectors. Methods for constructing and using viral vectors are known in the art (See e.g., Miller and Rosman (1992) BioTech., 7:980-990). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. (1991) Mol. Cell. Neurosci., 2:320-330), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. ((1992) J. Clin. Invest., 90:626-630; See also, La Salle et al. (1993) Science 259: 988-990); and a defective adeno-associated virus vector (Samulski et al. (1987) J. Virol., 61:3096-3101; Samulski et al. (1989) J. Virol., 63:3822-3828; and Lebkowski et al. (1988) Mol. Cell. Biol., 8:3988-3996).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In some embodiments, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol. (1990) 75-81), ovine, porcine, avian, and simian (e.g., SAV) origin.

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In particular embodiments, the adenoviral vector has a deletion in the E1 region (Ad 1.0). Examples of E1-deleted adenoviruses are disclosed in EP 185,573, the contents of which are incorporated herein by reference. In another embodiment, the adenoviral vector has a deletion in the E1 and E4 regions (Ad 3.0). Examples of E1/E4-deleted adenoviruses are disclosed in WO 95/02697 and WO 96/22378. In still another embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al. (1991) Gene 101:195; EP 185 573; and Graham (1984) EMBO J., 3:2917). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al. (1977) J. Gen. Virol., 36:59), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al. (1983) Cell 33:153; Markowitz et al. (1988) J. Virol., 62:1120; PCT/US95/14575; EP 453242; EP178220; Bernstein et al. (1985) Genet. Eng., 7:235; McCormick (1985) BioTechnol., 3:689; WO 95/07358; and Kuo et al. (1993) Blood 82:845). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al. (1987) J. Virol., 61:1639). Recombinant retroviral vectors are purified by standard techniques known to those having ordinary skill in the art. In some embodiments, retroviral vectors encode siRNAs with strand specificity; this avoids self-targeting of the viral genomic RNA; in particular embodiments, the retroviral vector comprise a U6 promoter (Ilves, H. et al. (1996) Gene 171, 203-8).

In some embodiments, siRNA gene therapy is used to knock out a mutant allele, leaving a wild-type allele intact. This is based on the observation that in order to be effective, the siRNA generally must have about 100% homology with the sequence of the target gene.

In other embodiments, siRNA gene therapy is used to transfect every cell of an organism, preferably of mammalian livestock.

In other embodiments, siRNA is operably linked to a developmentally specific promoter, and/or a tissue specific promoter, and is therefore expressed in a developmentally specific manner, and/or in a specific tissue.

In yet other embodiments, siRNA therapy is used to inhibit pathogenic genes. Such genes include, for example, bacterial and viral genes; preferred genes are those which are necessary to support growth of the organism and infection of a host. In alternative embodiments, siRNA gene therapy is used to target a host gene which is utilized by a pathogen to infect the host. In some embodiments, the siRNA transcripts are hairpin siRNAs, with a 19 nucleotide pair which is 100% homologous to a specific sequence of the target gene. The siRNA genes are then inserted into an expression cassette, such as is described above and in the Examples. This cassette is then placed into an appropriate vector for transient transfection; appropriate vectors are described above and in the Examples. The time course of the transfection is preferably sufficient to prevent infection of the host by the pathogen. The vector is then used to transfect the organism in vivo. In alternative aspects, the vector is used to transfect cells collected from the host in vitro, and the transfected cells are then cultured and re-implanted into the host organism. Such cells include, for example, cells from the immune system.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); μmol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); DS (dextran sulfate); ° C. (degrees Centigrade); nt, nucleotide; RNAi, RNA interference; siRNA, small (or short) interfering RNA; ds siRNA, double-stranded siRNA; and Sigma (Sigma Chemical Co., St. Louis, Mo.).

Example 1

Materials and Methods siRNA Synthesis

For in vitro transcription, 40-nt DNA template oligonucleotides were designed to produce 21-nt siRNAs. siRNA sequences of the form $GN_{17}CN_2$ were selected for each target, since efficient T7 RNA polymerase initiation requires the first nt of each RNA to be G (Milligan, J. F. et al. (1987) *Nucleic Acids Res* 15, 8783-98). The last two nt form the 3' overhang of the siRNA duplex and were changed to U for the sense strand (Elbashir, S. M. et al. (2001) *Nature* 411, 494-8) (see FIGS. 1A and 1B and FIG. 5 for sequences). For hairpin siRNAs, only the first nt needs to be G (FIG. 2A). Each template and a 20-nt T7 promoter oligonucleotide (FIG. 1B) were mixed in equimolar amounts, heated for 5 min at 95° C., then gradually cooled to room temperature in annealing buffer (10 mM Tris-HCl and 100 mM NaCl). In vitro transcription was carried out using the AmpliScribe T7 High Yield Transcription Kit (Epicentre, Madison, Wis.) with 50 ng of oligonucleotide template in a 20 μl reaction for 6 hours or overnight. RNA products were purified by QIAquick Nucleotide Removal kit (Qiagen, Valencia, Calif.). For annealing of siRNA duplexes, siRNA strands (150-300 ng/μl in annealing buffer) were heated for 5 min at 95° C., then cooled slowly to room temperature. Short products from the in vitro transcription reactions (Milligan, J. F. et al. (1987) *Nucleic Acids Res* 15, 8783-98) were observed to sometimes reduce transfection efficiency, so siRNA duplexes and hairpin siRNAs were gel purified using 4% NuSieve GTG agarose (BMA, Rockland, Me.). RNA duplexes were identified on the gel by co-migration with a chemically synthesized RNA duplex of the same length, and recovered from the gel by β-agarase digestion (New England Biolabs, Beverly, Mass.). The DhGFP1 siRNAs were chemically synthesized (Dharmacon Research, Lafayette, Colo.) deprotected as directed by the manufacturer and annealed as described above. RNAs were quantified using RiboGreen fluorescence (Molecular Probes, Eugene, Oreg.).

Cell Culture and Transfections

Mouse P19 cells (McBurney, M. W. (1993) *Int J Dev Biol* 37, 135-40) were cultured as previously described (Farah, M. H. et al. (2000) *Development* 127, 693-702). For transfection, cells were plated on dishes coated with murine laminin (Invitrogen, Carlsbad, Calif.) at 70-90% confluency without antibiotics. Transfections were performed with Lipofectamine 2000 (Invitrogen, Carlsbad, Calif.) as directed by the manufacturer. For inhibition of GFP, 1.6 μg CS2+eGFP (Farah, M. H. et al. (2000) *Development* 127, 693-702) was co-transfected with 200 ng siRNAs per 35 mm dish. Cells were fixed 19-20 hr after transfection. For inhibition of neuronal β-tubulin, 1.0 μg biCS2-eGFP/Mash1 was co-transfected with either 200 ng siRNAs or 0.8 μg of each U6 siRNA vector per 35 mm dish. Media was replaced with OPTI-MEM1 (Invitrogen, Carlsbad, Calif.) supplemented with 1% fetal bovine serum 8-14 hr after transfection and changed 3 days after transfection. Cells were fixed 3.5-4 days after transfection.

Expression Plasmids

Plasmids were constructed using standard techniques. The mouse U6 promoter (Reddy, R. (1988) *J Biol Chem* 263, 15980-4) was isolated by PCR from mouse genomic DNA with the oligonucleotides CCCAAGCTTATCCGACGC-CGCCATCTCTA (SEQ ID NO:1) and GGGATCC GAAGACCACAAACAAGGCTTTTCTCCAA (SEQ ID NO:2). An introduced Bbs1 site (underlined) was introduced to allow insertion of siRNA sequences at the first nucleotide of the U6 transcript. The U6 promoter was cloned into the vector RARE3E (Davis, R. L. et al. (2001) *Dev Cell* 1, 553-65). siRNA and hairpin siRNA sequences were synthesized as two complementary DNA oligonucleotides, annealed, and ligated between the Bbs1 and Xba1 sites (see FIG. 4A and FIG. 5 for sequences). The biCS2+MASH1/eGFP vector is a variant of CS2 (Rupp, R. A. et al. (1994) *Genes Dev* 8, 1311-1323; and Turner, D. L. & Weintraub, H. (1994) *Genes Dev* 8, 1434-1447) that contains both the rat MASH1 (Johnson, J. E., Birren, S. J. & Anderson, D. J. (1990) *Nature* 346, 858-61) and the EGFP (BD Sciences ClonTech, Palo Alto, Calif.) coding sequence, expressed in divergent orientations by two promoters and a shared simian CMV IE94 enhancer. CS2+luc contains the luciferase gene from pGL3 (Promega, Madison, Wis.) inserted into the CS2+vector (Rupp, R. A. et al. (1994) *Genes Dev* 8, 1311-1323; and Turner, D. L. & Weintraub, H. (1994) *Genes Dev* 8, 1434-1447).

Reporter Assays

Approximately 500 nucleotides from the 3' end of the EGFP coding region was inserted into CS2+luc plasmid after the luciferase stop codon in sense (CS2+luc-GFP-S) and antisense (CS2+luc-GFP-AS) orientation. In 12-well plates, 500 ng CS2+luc, CS2+luc-GFP-S, or CS2+luc-GFP-AS were cotransfected with 150 ng siRNAs and 500 ng CS2+cβgal (Turner, D. L. & Weintraub, H. (1994) *Genes Dev* 8, 1434-1447) per well. 150-200 ng of siRNA gave near maximal inhibition based on dose response tests. Reporter activity was assayed 19-20 hr after transfection using the Dual-Light system (Applied Biosystems/Tropix, Foster City, Calif.). Luciferase activity was normalized to β-galactosidase activity to control for transfection efficiency. To test the effect of denaturation on siRNA function, siRNAs were diluted to 3 ng/μl, heated to 95° C. for 5 minutes, cooled on ice and diluted for transfection.

Immunohistochemistry and Antibodies

Cells were fixed for 10 min with 3.7% formaldehyde in phosphate-buffered saline (PBS) as described (Farah, M. H. et al. (2000) *Development* 127, 693-702). Antibody dilutions: mouse monoclonal TuJ1 antibody (CRP, Cumberland, Va.) against neuronal class III β-tubulin 1:2000, mouse monoclonal 16A11 (Molecular Probes) against HuC/D 1:500, and Alexa Fluor 546 goat anti-mouse IgG secondary antibody (Molecular Probes) 1:4000. Cells were photographed with a video camera on an inverted microscope and the images digitized. Cell counts for GFP and HuC/D were performed using NIH Image software. TuJ1-labeled cells were counted manually. The number of antibody labeled cells was normalized to the number of GFP expressing cells for each field of view.

Example 2

Inhibition of Reporter Gene Expression by ds siRNAs Synthesized by In Vitro Transcription To test the ability of RNAs generated by in vitro transcription to function as siRNAs, complementary pairs of 21-nt RNAs were synthesized with T7 RNA polymerase and partially single-stranded DNA oligonucleotide templates (FIGS. 1A and 1B) (Milligan, J. F. et al. (1987) *Nucleic Acids Res* 15, 8783-98). Each pair of 21-nt siRNA strands was synthesized separately and annealed to create a 19-nt siRNA duplex (ds siRNA), with two nt 3' overhangs at each end as previously described (see Example 1, Materials and Methods, for details of synthesis, purification, and quantitation).

As a rapid assay for siRNA function, the ability of either T7 or chemically synthesized siRNA duplexes to inhibit the expression of Green Fluorescent Protein (GFP) in a transient transfection was tested. siRNAs and an expression vector for GFP were cotransfected into mouse P19 cells, and GFP expression was assessed by epifluorescence. DhGFP1, a duplex of chemically-synthesized siRNAs, and GFP5, a T7 synthesized siRNA duplex, both efficiently reduced GFP expression.

To confirm that inhibition was sequence specific, GFP5m1, a T7 synthesized siRNA duplex with a two base mismatch in each strand located at the presumptive cleavage site in the GFP target (Elbashir, S. M. et al. (2001) *Genes Dev* 15, 188-200; and Elbashir, S. M. et al. (2001) *Embo J* 20, 6877-88), was tested. GFP fluorescence was effectively reduced by co-transfection of either the DhGFP1 or GFP5 siRNAs with a GFP expression vector, but not by the GFP5m1 siRNA. Thus, the GFP5m1 siRNA duplex did not reduce GFP fluorescence.

To quantify siRNA-mediated inhibition, part of the GFP gene was inserted into the 3' untranslated region of the luciferase reporter in the CS2+luc expression vector, in both sense (CS2+luc-GFP-S) and antisense (CS2+luc-GFP-AS) orientations (FIG. 1D). Based on studies in *Drosophila* extracts, it was expected that siRNA duplexes would inhibit a mammalian mRNA containing either sense or antisense target sequences. While co-transfection of the DhGFP1 or GFP5 siRNA duplexes did not inhibit luciferase activity from the CS2+luc vector (which does not contain matching sequences), both siRNA duplexes reduced luciferase expression by 5-7 fold from the CS2+luc-GFP-S and CS2+luc-GFP-AS vectors (FIG. 1C). This indicates that a T7 synthesized siRNA can inhibit gene expression in mammalian cells as effectively as a chemically synthesized siRNA. GFP2, another T7 synthesized siRNA duplex directed against a different sequence in GFP (partially overlapping the DhGFP1 target), also reduced luciferase activity, although slightly less effectively than the other siRNAs. Co-transfection of the mismatched GFP5m1 siRNA duplex did not inhibit luciferase activity from CS2+luc-GFP-S at all, consistent with its lack of effect on GFP fluorescence, while it inhibited luciferase activity from CS2+luc-GFP-AS only slightly.

Example 3

Inhibition of Reporter Gene Expression by Hairpin siRNAs Synthesized by In Vitro Transcription The next step was to determine whether a short hairpin RNA could function like a siRNA duplex composed of two siRNA strands. The T7 in vitro transcription was used to synthesize variants of the GFP5 siRNAs in which the two siRNA strands were contained within a single hairpin RNA (hp siRNA), with the sequence for each strand connected by a loop of three nucleotides (FIG. 2A). In GFP5HP1, the GFP5 antisense siRNA (corresponding to the antisense strand of GFP) is located at the 5' end of the hairpin RNA, while in GFP5HP1S, the GFP5 sense siRNA is at the 5' end of the hairpin RNA. The loop sequence for each vector is a continuation of the 5' end siRNA in the hairpin. Each hairpin RNA ended with two unpaired U residues that did not match the target strand. As a control for sequence specificity, the GFP5HP1m1 hairpin RNA was also synthesized; GFP5HP1m1 has a two base mismatch with GFP (analogous to the GFP5 m1 siRNA duplex). All hairpin RNAs migrated on a non-denaturing gel with the same mobility as the annealed DhGFP1 or GFP5 siRNA duplexes, consistent with synthesis of the full-length RNA.

Hairpin siRNA Inhibits Gene Expression

Figure 2:
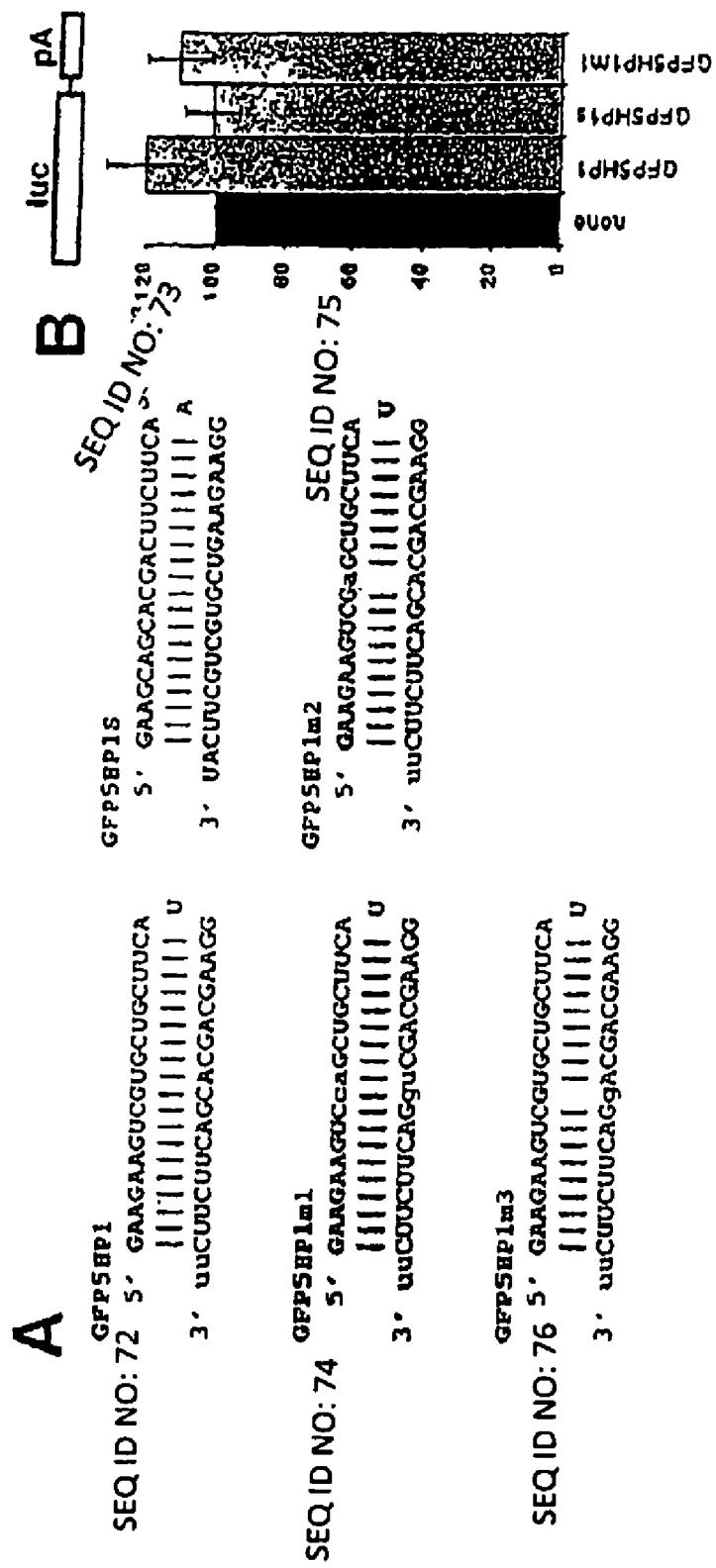
FIG. 2 shows RNA interference using hairpin siRNAs synthesized by in vitro transcription. Panel A (SEQ ID NOS:72-76) shows sequences and expected structures for the hairpin siRNAs to GFP (notation as in FIG. 1). GFP5HP1m2 and GFP5HP1m3 contain single base mismatches with the sense and antisense strands of GFP respectively, while GFP5HP1m1 contains a two base mismatch identical to GFP5m1 (see FIG. 1A). Panels B-D show quantitation of hairpin siRNA inhibition of luciferase activity (see legend for FIG. 1D). Panel B shows that CS2+luc is not inhibited by the hairpin siRiNAs. Panel C shows that GFP5HP1 and GFP5HP1S inhibit luciferase from both sense and antisense targets. The GFP5HP1m1 hairpin cannot inhibit effectively luciferase activity from vectors containing either strand of GFP in the luciferase mRNA, while GFP5HP1m2 and GFP5HP1m3 have reduced inhibition only for the mismatched strand. Panel D shows that denaturation (dn) of the GFP5 siRNA reduces inhibition of a luciferase-GFP target, while denaturation of GFP5HP1 does not significantly alter inhibition.
Figure 2:
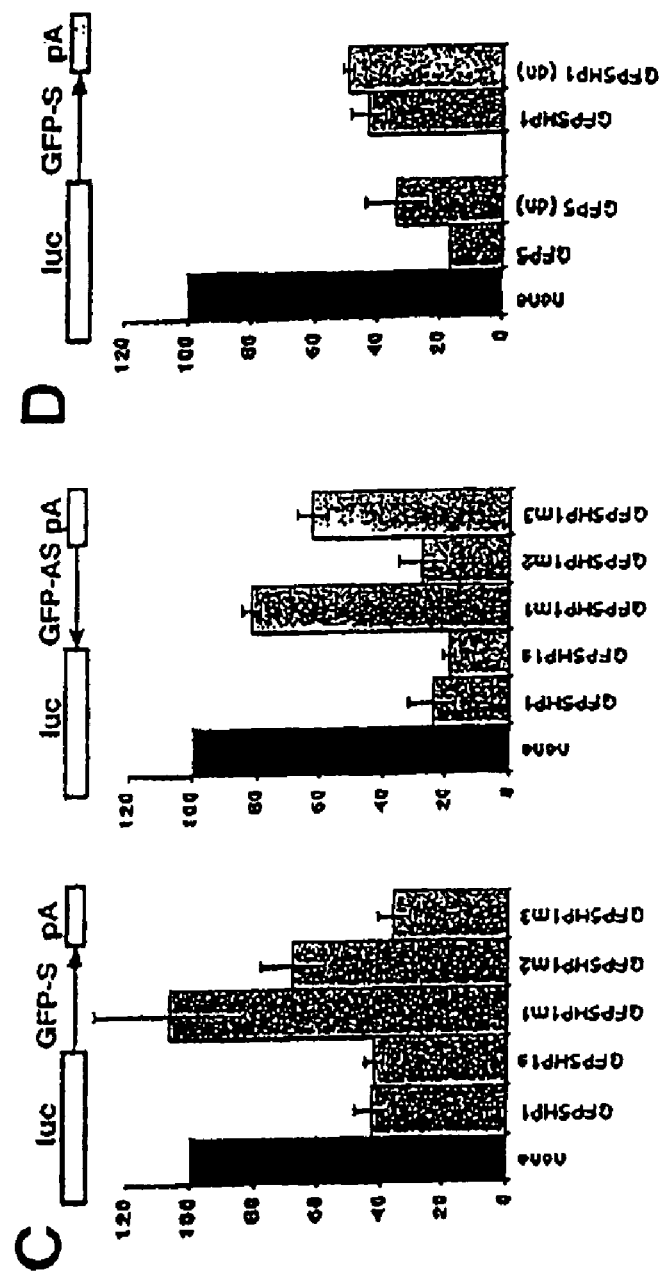

When cotransfected into cells with luciferase vectors, both the GFP5HP1 and GFP5HP1S hairpin RNAs inhibited luciferase activity from the CS2+luc-GFP-S and CS2+luc-GFP-AS vectors, but not the CS2+luc vector (FIG. 2, panels B and C). The order of the sense and antisense strands within the hairpin RNA did not alter inhibition, although neither hairpin RNA was as effective as the GFP5 siRNA duplex. As expected, the GFP5HP1m1 hairpin RNA was completely ineffective in inhibiting luciferase expression from CS2+luc-GFP-S, and it inhibited luciferase expression from CS2+luc-GFP-AS only slightly. This is identical to the effects of the GFP5m1 siRNA on luciferase activity from these two vectors (FIG. 1C). These observations, as well as additional observations described below, suggest that a hairpin siRNA molecule functions similarly to a siRNA duplex (ds siRNA), and that hairpin siRNAs have the same sequence specificity as a duplex siRNA.

Hairpin siRNA Functions as a Single Molecule

The possibility that two hairpin siRNA molecules might function as a longer siRNA duplex, rather than as a single molecule hairpin siRNA, was considered. If the hairpin RNA functioned primarily as a single RNA molecule, it should be resistant to denaturation, since both "strands" of the siRNA are covalently linked, while denaturation of the GFP5 siRNA should reduce inhibition. The inhibition of luciferase activity from CS2+luc-GFP-S by the GFP5 siRNA duplex and the GFP5HP1 hairpin siRNA after denaturation immediately prior to transfection were compared (FIG. 2D). While inhibition by the GFP5 duplex decreased, GFP5HP1 inhibition remained unchanged, consistent with the hypothesis that GFP5HP1 functions primarily as a single RNA molecule. Although it is not necessary to understand the underlying mechanism, and the invention is not intended to be limited to any particular theory of any mechanism, it is speculated that the failure of denaturation to completely prevent GFP5 siRNA duplex inhibition may reflect reannealing of the two strands during transfection or inside cells.

Strand Specificity of Hairpin siRNA

Like siRNA duplexes, hairpin siRNAs can inhibit either the sense or antisense sequences of a target (FIG. 2C). It is contemplated to be useful to inhibit only the one strand of a target RNA, and not the complementary strand (for example, to prevent self-targeting of a vector expressing the siRNA hairpin). The effect of single base changes in either the antisense (GFP5HP1m2) or sense (GFP5HP1m3) sequences of the GFP5HP1 hairpin (FIG. 2A) on the inhibition of luciferase activity from CS2+luc-GFP-S and CS2+luc-GFP-AS was tested. In each case, the ability of the hairpin to inhibit the GFP strand complementary to the mismatched sequence was reduced, while inhibition of the perfectly matched GFP strand was unaffected (FIG. 2C). Thus, a hairpin siRNA can preferentially inhibit one strand of a target gene, and base pairing within the hairpin siRNA duplex need not be perfect to trigger inhibition. Although a single base mismatch in the hairpin siRNA provided only partial strand specificity, it is contemplated that increased specificity is achieved with additional mismatched bases.

Example 4

Inhibition of Endogenous Gene Expression by ds siRNAs and by Hairpin siRNAs, Both Synthesized by In Vitro Transcription The ability of T7 synthesized siRNAs and hairpin siRNAs to inhibit endogenous gene expression was tested using a cell culture model of neuronal differentiation. The inventors have previously shown that uncommitted mouse P19 cells can be converted into differentiated neurons by the transient expression of neural basic helix-loop-helix (bHLH) transcription factors (Farah, M. H. et al. (2000) *Development* 127, 693-702). An abundant and readily detectable protein marker of neuronal differentiation expressed in these neurons is the neuron-specific β-tubulin type III recognized by the monoclonal antibody TuJ1 (Lee, M. K. et al. (1990) *Cell Motil Cytoskeleton* 17, 118-32), referred to here as neuronal β-tubulin.

Figure 3:
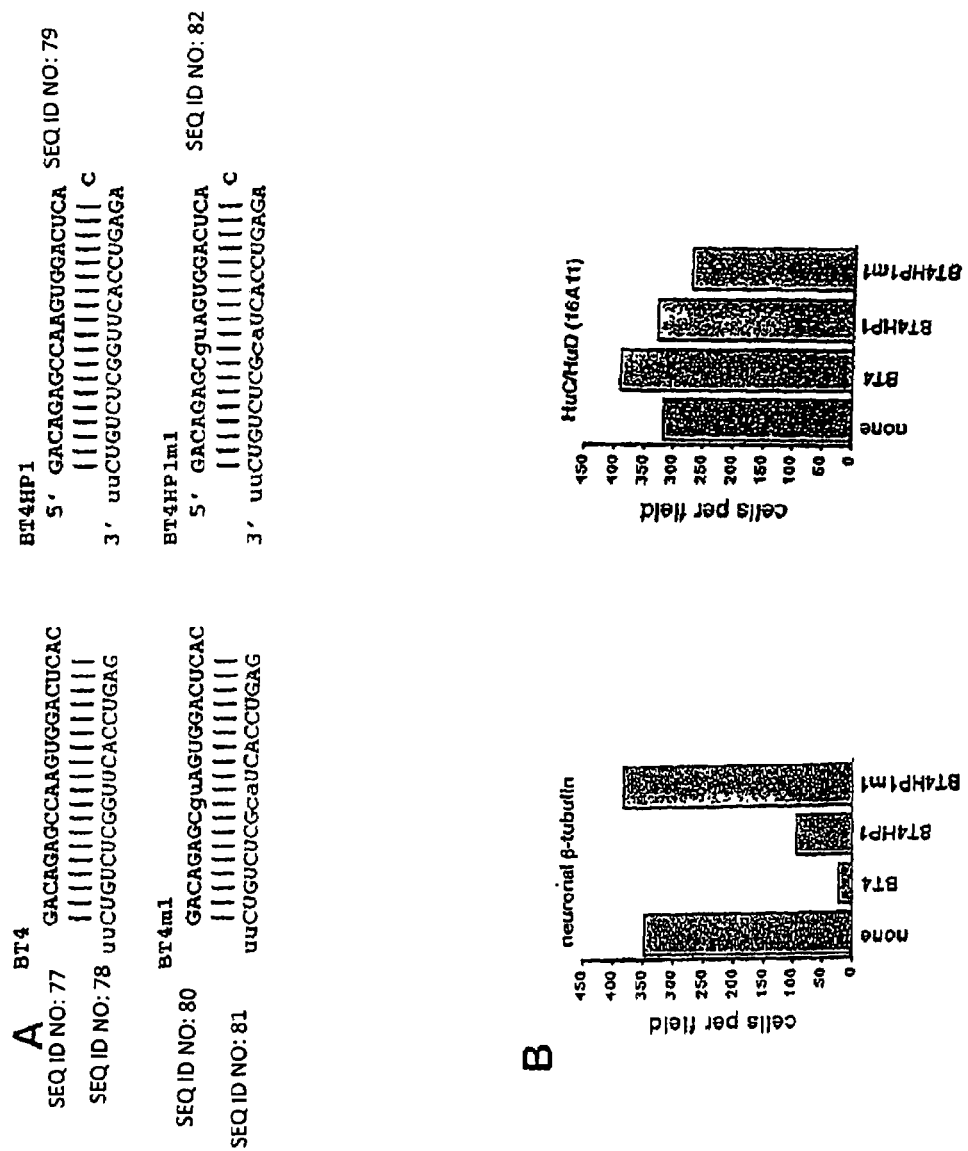
FIG. 3 shows RNAi with neuronal β-tubulin using in vitro synthesized ds siRNAs and hairpin siRNAs. Panel A (SEQ ID NOS:77-82) shows sequences and expected structures for the ds siRNAs and hairpin siRNAs against neuronal β-tubulin (notation as in FIG. 1). Panel B shows cells per field expressing detectable neuronal β-tubulin or the HuC/HuD neuronal RNA binding proteins detected by indirect immunofluorescence after co-transfection of biCS2+MASH1/GFP and BT4, BT4HP1, or BT4HP1ml siRNAs. Standard error per field is shown. Neuronal β-tubulin and HuC/HuD were scored in parallel transfections and cell numbers were normalized to the number of GFP expressing cells in each field to control for transfection efficiency.
Figure 6:
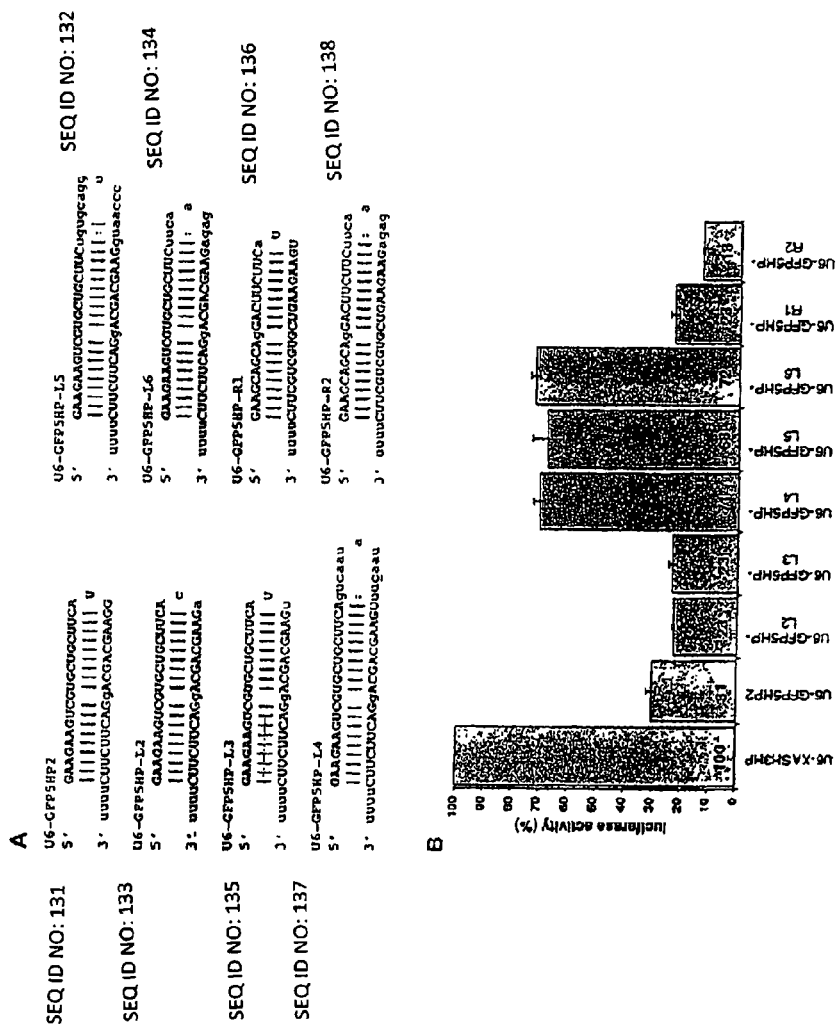
FIG. 6 shows the effects of loop sequences on inhibition by hairpin siRNA vectors. (A) The loop sequence of the hairpin siRNA in the U6-GFP5HP2 vector was replaced with various sequences (SEQ ID NOS:131-138). Bases shown in bold are from the antisense strand of the GFP target (i.e. complementary to the GFP mRNA), while non-bold capital letters indicate bases from the sense strand of GFP. Lower case bases do not match either strand. Solid lines denote Watson-Crick base pairs; GU base pairs are indicated by two dots. The loop in U6-GFP5-L4, derived from miR29, includes a U to C substitution (underlined) to disrupt an RNA polymerase III terminator. (B) Inhibition of luciferase activity from an inducible luciferase-GFP target was assessed for each U6 GFP hairpin siRNA vector, relative to the control vector U6-XASH3HP. Expression of the luciferase-target was induced 14 hours after transfection and luciferase activity was measured 14 hours later (see Materials and Methods). Numerical values (%) for luciferase activity are listed within each bar. Data shown is an average of three transfections with standard errors indicated.
Figure 7:
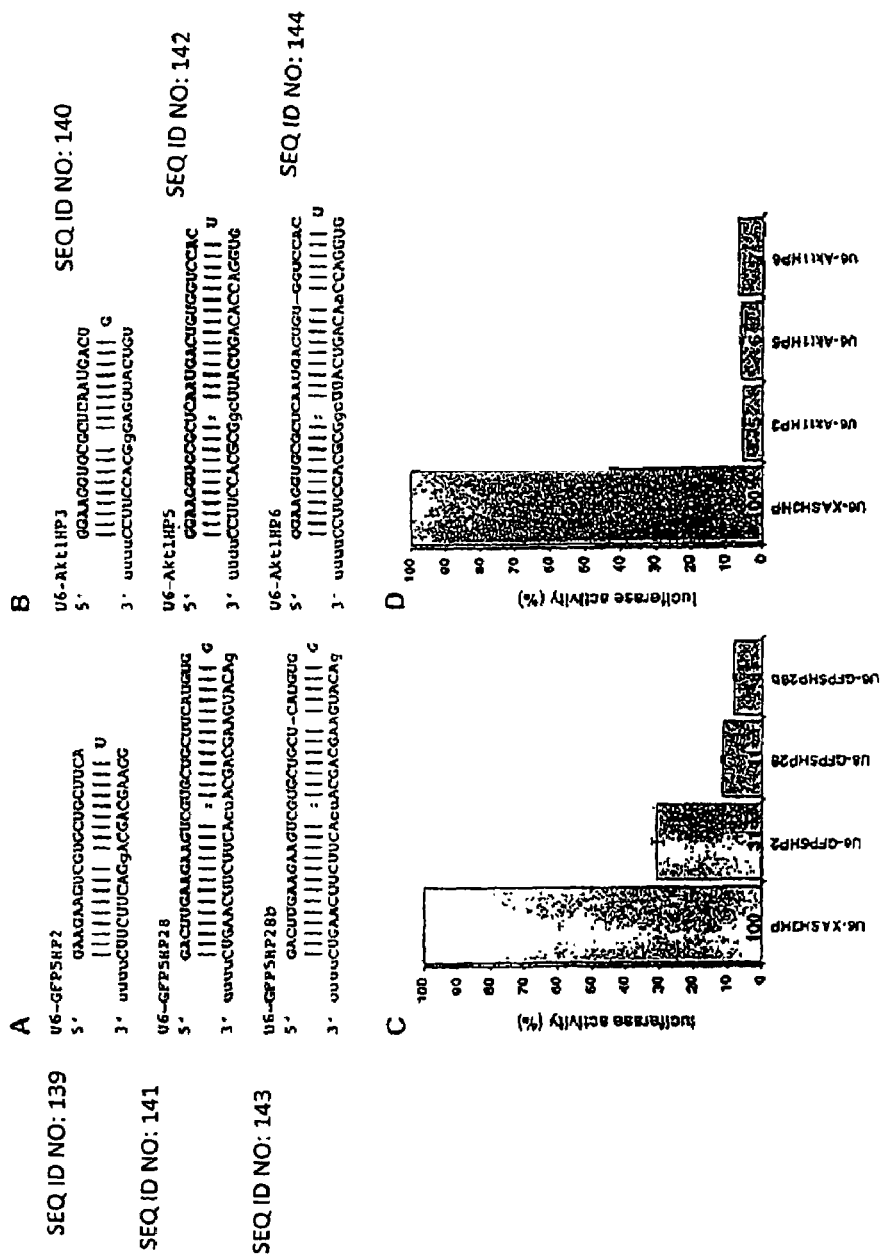
FIG. 7. Effect of duplex length on inhibition by hairpin siRNA vectors. The length of the duplex regions for the hairpin siRNA in the U6-GFP5HP2 (A) and U6-Akt1HP3 vectors (B) were increased to 28 nucleotides, with or without an internal unpaired base (SEQ ID NOS:139-144). Sequence notation as in FIG. 1. Inhibition of luciferase activity from the inducible luciferase-GFP target (C) or a luciferase-Akt1 target (D) was assessed for each U6 hairpin siRNA vector as described for FIG. 1.
Figure 8:
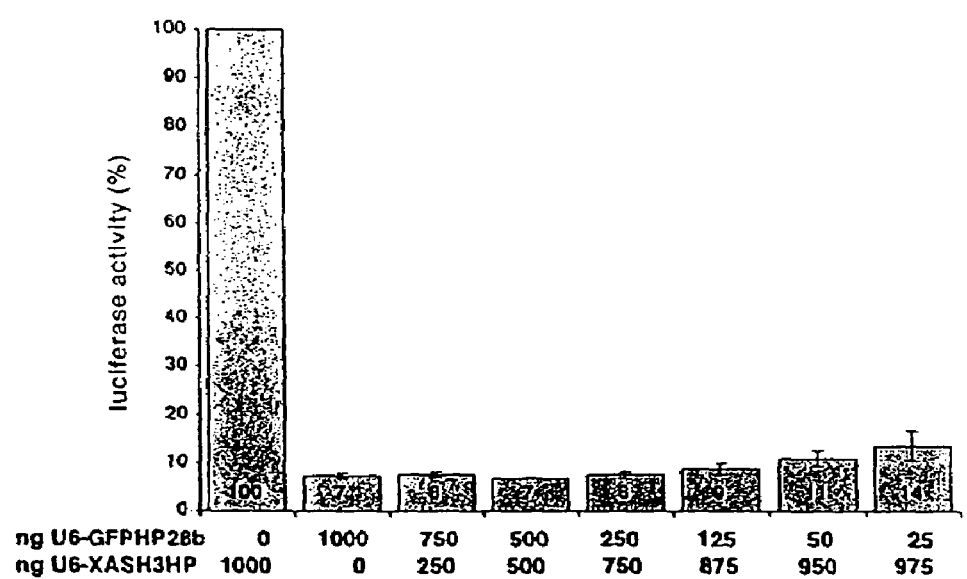
FIG. 8. Cotransfection of two U6 hairpin siRNA vectors does not reduce RNAi. The U6-XASH3HP control vector and the U6-GFP28b vector were cotransfected in varying ratios with a constant total amount of DNA. Inhibition of luciferase activity from the inducible luciferase-GFP target was determined as described for FIG. 1.
Figure 10:
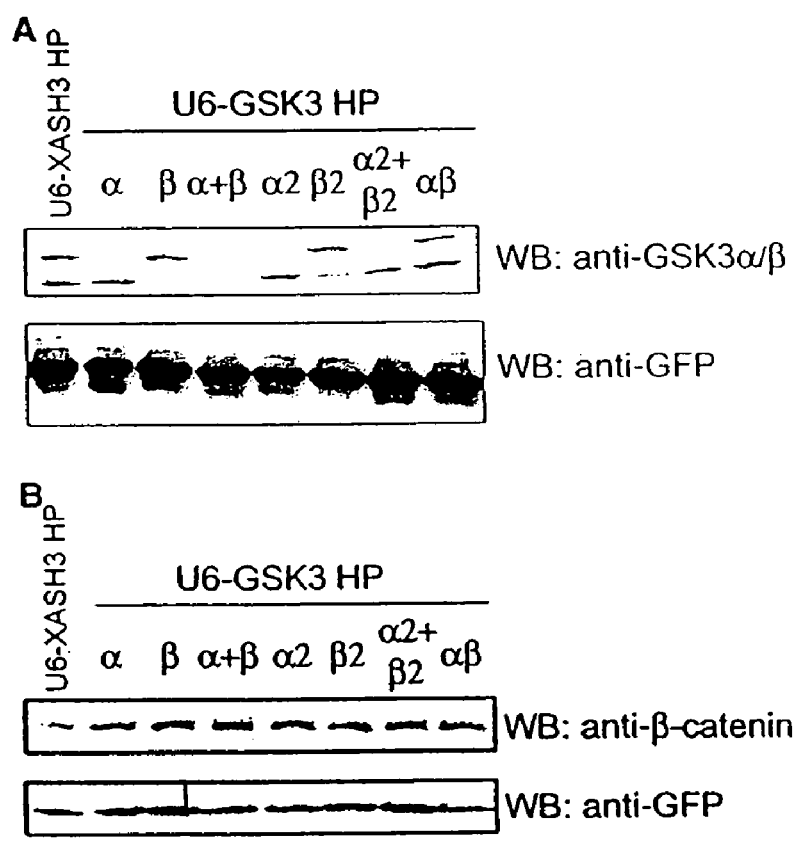
FIG. 10. Inhibition of GSK3α and GSK3β expression and upregulation of β-catenin levels by hairpin siRNAs against GSK3α and GSK3β. (A) Western blot analysis of the expression of GSK3α, GSK3β, and GFP in whole cell extracts from mouse P19 cells transiently transfected with U6 hairpin siRNA expression vectors targeted against each kinase or the U6-XASH3HP control vector. Cells were cotransfected with a vector that expresses the puromycin resistance gene and GFP, allowing transiently selection with puromycin (see text). The anti-GSK3 antisera recognizes both GSK3α and GSK3 β; the upper band is GSK3α while the lower band is GSK3β. (B) Western blot analysis of β-catenin and GFP expression in P19 cells transfected with the indicated U6-expression vectors as described for (A).

Both a siRNA duplex and a hairpin siRNA directed against the same target sequence in the 3' untranslated region of the mRNA for neuronal β-tubulin (GenBank Accession number AF312873) was synthesized (FIG. 3A). Mouse P19 cells were cotransfected with the siRNAs and biCS2MASH1/eGFP, a vector that expresses both the neural bHLH protein MASH1 and GFP from a shared enhancer. GFP fluorescence and neuronal β-tubulin expression were detected by indirect immunofluorescence in mouse P19 cells 4 days after co-transfection with biCS2+MASH1/GFP and various siRNAs. The results indicated that GFP5 reduced GFP expression to undetectable levels in most cells without altering detected levels of neuronal β-tubulin (NT) expression, while BT4 and BT4HP1 reduced the number of neuronal β-tubulin expressing cells without altering GFP expression. The mismatched siRNA BT4HP1m1 had no effect on GFP or neuronal β-tubulin.

Thus, co-transfection of the siRNA duplex against neuronal β-tubulin substantially reduced the number of neuronal β-tubulin expressing cells detected by indirect immunofluorescence (~7-fold), but it did not alter GFP expression FIGS. 3B). In contrast, co-transfection of the GFP5 siRNA duplex reduced GFP expression, but it did not alter neuronal β-tubulin expression.

Moreover, co-transfection of the hairpin siRNA against neuronal β-tubulin also reduced the number of neuronal β-tubulin expressing cells detected by indirect immunofluorescence (~4-fold), although not as effectively as the double-stranded siRNA. The decrease in the number of neuronal β-tubulin expressing cells did not reflect either cell death or a failure of the transfected cells to differentiate, since the number of transfected cells expressing the HuC/HuD RNA binding proteins (markers of neuronal differentiation recognized by the monoclonal antibody 16A11) did not. Co-transfection of either a siRNA duplex or a hairpin siRNA against neuronal β-tubulin where the siRNA contained a two base-mismatch with the target prevented inhibition (FIGS. 3A and 3B).

Example 5

Inhibition of Endogenous Gene Expression by ds siRNA and by Hairpin siRNA, Both Expressed In Vivo This set of experiments describes the inhibition of an endogenous gene, neuronal β-tubulin, with siRNA expressed in vivo from U6 siRNA expression vectors.

An initial concern was that sequence extensions at either end of a siRNA of siRNAs and hairpin siRNAs expressed in mammalian cells might prevent inhibition. Therefore, an expression vector was constructed based upon the mouse U6 promoter, in which a sequence could be inserted after the first nucleotide of the U6 transcript (a G). By selecting siRNA sequences that begin with G, it is possible to express siRNAs in this vector that precisely match the target gene, except for the four 3' end U residues from RNA polymerase III termination (FIGS. 4A and 4B). The terminal U residues were used as 3' overhanging ends for both siRNAs and hairpin siRNAs, since the overhanging ends of a siRNA need not match its target sequence, and their length can be varied from at least 2 to 4 nucleotides (Elbashir, S. M. et al. (2001) *Genes Dev* 15, 188-200; Elbashir, S. M. et al. (2001) *Embo J* 20, 6877-88; and Lipardi, C. et al. (2001) *Cell* 107, 297-307). All of the T7 synthesized siRNAs began with G (FIG. 3A), so the same sequences were used to target neuronal β-tubulin in the U6 expression system. The U6-BT4s and U6-BT4 as vectors were expected to express 21-nucleotide complementary single-stranded RNAs with 19 nucleotide corresponding to the sense or antisense strands of the BT4 siRNA duplex (each U6 vector expresses one siRNA strand), while the U6-BT4HP1, U6-BT4HP2, and U6-BT4HP2m1 vectors are expected to express 45 nucleotide hairpin siRNAs (FIG. 4B). The U6-BT4HP2 contains a one base mismatch in the sense strand of the hairpin siRNA, analogous to the GFP5HP1m3 siRNA (FIG. 2A), while the antisense strand of U6-BT4HP2m1 contains an two base mismatch with GFP. GFP fluorescence and indirect immunofluorescence for neuronal β-tubulin (NT) were examined 4 days after co-transfection of the indicated U6 vectors and biCS2+MASH1/GFP.

Co-transfection of the U6-BT4 as and U6-BT4s vectors reduced the number of neuronal β-tubulin expressing cells generated by biCS2MASH1/eGFP about four-fold (FIG. 4D). In addition, the intensity of fluorescence was reduced for most cells with detectable neuronal β-tubulin by indirect immunofluorescence, suggesting decreased levels of expression. The U6-BT4 as and U6-BT4s vectors had little or no effect on the number of neuronal β-tubulin expressing cells when cotransfected individually with biCS2MASH1/eGFP, indicating that both U6 driven siRNA strands are required for effective inhibition (FIG. 4C). A vector in which the two siRNA strands were expressed from tandem U6 promoters on a single plasmid was also examined. This vector inhibited neuronal β-tubulin with approximately the same efficiency as was observed for co-transfection with the U-BT4 as and U6-BT4s vectors, suggesting that co-transfection efficiency is not a limiting factor for inhibition. Co-transfection of the U6-BT5 as and U6-BT5s vectors (FIG. 4B), which express two complementary siRNA strands targeted against a different sequence in neuronal β-tubulin, reduced the number of expressing cells with similar efficiency to U6-BT4 as and U6-BT4s (FIG. 4C).

Co-transfection of either of the hairpin siRNA expression vectors (U6-BT4HP1 or U6-BT4HP2) with biCS2MASH1/eGFP resulted in a 100-fold reduction in cells with detectable neuronal β-tubulin staining (FIG. 4C). This was more effective inhibition than either co-transfection of the U6-BT4 as and U6-BT4s vectors together, or co-transfection of in vitro synthesized siRNAs (compare with FIG. 3B). Similar results also were obtained with a variant of U6-BT4HP2 in which the loop sequence was extended to four nucleotides. In contrast, neuronal β-tubulin expression was only slightly reduced by co-transfection of the mismatched hairpin expression vector U6-BT4HP2m1 (FIG. 4C). In addition, expression of the HuC/HuD neuronal RNA binding proteins and GFP were not altered by any of the U6 siRNA or hairpin siRNA expression vectors (FIG. 4C), indicating that the inhibition of neuronal β-tubulin by the U6-BT4HP1 and U6-BT4HP2 vectors is specific.

Example 6

Inhibition of Exogenous Gene Expression by Hairpin siRNA Synthesized and Accumulated In Vivo This experiment describes the inhibition of an exogenous gene after the synthesis and accumulation of siRNA in vivo, where the exogenous gene and expression cassette encoding the siRNA are co-transfected into a host cell at the same time.

The experiment was performed by cotransfection of P19 cells with 3EUAS-Luciferase-GFPs (100 ng/well), the target exogenous gene, CS2+G4D-ER™-G4A, a DNA-binding activator protein, and the mU6 hairpin siRNA expression vectors (400 ng/well) shown below. 3EUAS expression is activated by gal4 DNA-binding activator proteins. G4D-ER™-G4A is a gal4 activator protein that is dependent on the steroid hormone 4-OH tamoxifen for function. Thus, expression of the luciferase-GFPs target mRNA can be initiated subsequent to transfection by addition of 4-OH tamoxifen. This system allows a hairpin siRNA to be synthesized and accumulate in the transfected cells prior to the expression of target mRNA. The target (luciferase-GFPs) of the hairpin interfering RNA was induced at 25 hours after transfection. The luciferase assay was conducted 49 hours after the transfection, or 24 hours after induction of the target RNA. Other details of the assay are as described above.

All hairpin siRNAs are expressed from the mouse U6 promoter, with the expected structures shown below. The antisense strand of each siRNA is in bold. The two U6GFP5HP28 hairpins contain 27-28 nucleotide duplexes with some mismatched bases.

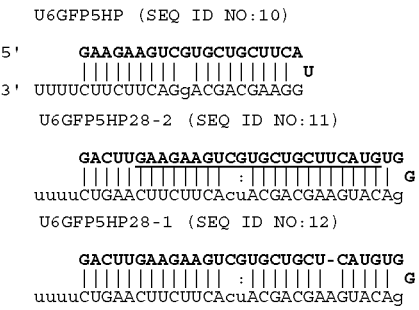

| U6-hairpin Vector | Results<br>Luciferase activity<br>% of control |
|---|---|
| Control | 100.00 |
| GFP5HP | 18.67 |
| GFP5HP28-1 | 6.97 |
| GFP5HP28-2 | 9.06 |

The increased length of U6GFP5HP28-2 improves inhibition relative to the shorter U6GFP5HP (the U6GFP5HP antisense sequence is contained within the longer U6GFP5HP28-2 duplex, as shown by the underline). The U6GFP5HP28-1 variant contains an unpaired nucleotide in the sense strand (with no corresponding nucleotide in the antisense strand). This further improves inhibition of the target gene. Although it is not necessary to understand the underlying mechanism, and the invention is not intended to be limited to any particular mechanism, it is contemplated that improved inhibition of the target gene reflects improved processing of the hairpin at the site of the mismatch. Other similar mismatch hairpin designs are also contemplated, which include one or more unpaired bases (contiguous or not) in either strand.

Example 7

Inhibition of Gene Expression by Multi-plex Hairpin siRNA Expressed In Vivo

Two multiplex hairpin siRNAs are designed, where the siRNA molecules are targeted against a different target gene. The first siRNA is targeted against an exogeneous gene, the reporter protein GFP, as described in Example 3, and the second siRNA is targeted against an endogenous gene, neuronal β-tubulin, as described in Example 5. In both multiplex molecules, the hairpin siRNAs are linked by an 8 nucleotide sequence; in a second experiment, the linking sequence comprises a cleavage site. In the first multiplex molecule, the first duplex region of the first siRNA and the third duplex region of the second siRNA are antisense regions, in that they are complementary to the target genes, where by "first region" it is meant that the duplex region occurs first in the polynucleotide siRNA sequence from 5' to 3', and by "third region" it is meant that the duplex region occurs third in the polynucleotide sequence from 5' to 3', where the second region is the loop region. In the second multiplex molecule, the first duplex region of the first siRNA and the first duplex region of the second siRNA are antisense regions.

The multiplex siRNAs are encoded by DNA molecules, where the multiplex coding sequence is operably linked to the mouse U6 promoter, as described in Example 5. These molecules are used to transfect mouse P19 cells as described above and in particular in Examples 1 and 5, and the inhibition of the target genes monitored, as described above and in particular in Examples 3 and 5. It is contemplated that both multiplex siRNA molecules result in inhibition of either or both target genes. It is further contemplated that the multiplex siRNA molecule comprising a cleavage site in the linking sequence is more effective in inhibiting both genes.

Example 8

Inhibition of Exogenous Gene Expression by Foldback Hairpin siRNAs Synthesized In Vitro The following experiments describe the inhibition of exogenous gene expression by foldback hairpin siRNAs that are synthesized in vitro.

Methods

T7 Synthesis of RNAs RNAs for foldback (fb) siRNAs and double stranded (ds) siRNAs were synthesized in vitro using high-yield T7 reaction kits (Epicentre). In most cases, 40-50 ng of synthetic DNA oligos encoding a T7 promoter and the RNA template were used. The template region was singled stranded after the first base of the RNA.

GFP Assay in Mammalian Cells

Mouse P19 cells in 35 mm cell culture dishes were cotransfected with a GFP expression plasmid (1-2 μg of CS2+eGFPBgl2) and either fb siRNA or ds siRNAs (usually 100 or 200 ng total) using Lipofectamine 2000 according to the manufacturer's directions. At approximately 16 hours after transfection, cells were scored with an inverted microscope for green fluorescence. Scale: 5, no inhibition; 1, strong inhibition (1 is equal to siRNA inhibition with the GFP5 ds siRNA, below). The GFP intensity listed with the sequence for a specific fb siRNA or ds siRNA is in most cases based upon multiple experiments. The level of inhibition may be a range due to experimental variation.

Luciferase Assays in Mammalian Cells

Mouse P19 cells were cotransfected with a luciferase expression plasmid that contains part of the eGFP coding region in antisense or sense orientation inserted after the luc coding region. This region contains the target sequences for the fb siRNA or ds siRNAs tested (usually 100 or 200 ng per 35 mm dish). Transfections were performed using Lipofectamine 2000 according to the manufacturer's directions. At approximately 16 hours after transfection, cells were processed to detect luciferase activity using a commercial detection system (Tropix).

Results siRNA Inhibition of eGFP

As a baseline for comparing the efficiency of fbRNA-meditated inhibition, various ds siRNAs were tested in mammalian cells. Specific fb siRNAs shown later are targeted against the same sequences as these siRNAs.

Double-stranded siRNAs ds siRNAs were generated by annealing two separately synthesized RNAs. Nucleotide numbering is based upon the CS2+eGFPBgl2 vector. For inhibition of eGFP mRNA, the antisense siRNA strand is the active strand.

eGFPS ds siRNA (Formerly eGFP3/4)

Lower case letters do not match the complementary strand of eGFP.

```
nt 322-344 of CS2 + eGFPBgl2

GAAGAAGUCGUGCUGCUUCAU  = antisense strand of eGFP
  |||||||||||||||||||||    (SEQ ID NO:13)
uuCUUCUUCAGCACGACGAAG    = sense strand of eGFP
                           (SEQ ID NO:14)
```

GFP intensity: 1 (=strong inhibition)

eGFP5m1 ds siRNA (Formerly eGFP3/4m1)

Two nucleotide target mismatch mutation in bold. The lack of inhibition by this mutant siRNA demonstrates the specificity of siRNA inhibition.

```
322-344

GAAGAAGUCcaGCUGCUUCAU  = antisense strand of eGFP
  |||||||||||||||||||||    (SEQ ID NO:15)
uuCUUCUUCAGguCGACGAAG    = sense strand of eGFP
                           (SEQ ID NO:16)
```

GFP intensity: 5 (=no inhibition)

eGFP2 ds siRNA (Formerly eGFP1/2)

An siRNA directed against a distinct sequence in eGFP. Less inhibitory than the GFP5 siRNA.

```
nt 727-749 of CS2 + eGFPBgl2
  GACCAUGUGAUCGCGCUUCUC  = antisense strand of eGFP
  |||||||||||||||||||||    (SEQ ID NO:17)
uuCUGGUACACUAGCGCGAAG    = sense strand of eGFP
                           (SEQ ID NO:18)
```

GFP intensity: 2

Alignment of GFP2 and GFP5 Sequences to eGFP

Many of the fb siRNAs are based upon the same eGFP sequences as the above ds siRNAs. For reference, these siRNAs are aligned to the appropriate regions of the eGFP sequence below.

```
eGFP (CS2+eGFPBgl2 vector)

310       320       330       340       350
  TACCCCGACCACATGAAGCAGCACGACTTCTTCAAGTCCGC      (SEQ ID NO: 19)
  ATGGGGCTGGTGTACTTCGTCGTGCTGAAGAAGTTCAGGCG
    Y  P  D  H  M  K  Q  H  D  F  F  K  S  A>    (SEQ ID NO:20)

eGFP5as    UACUUCGUCGUGCUGAAGAAG 5'               (SEQ ID NO:21)

eGFP5m1as  UACUUCGUCGacCUGAAGAAG 5'               (SEQ ID NO:22)
``` eGFP (CS2+eGFPBgl2 Vector) (Nucleic Acid (SEQ ID NO:23) and Amino Acid (SEQ Id NO:24)

```
       720       730       740       750       760       770
GACCCCAACGAGAAGCGCGATCACATGGTCCTGCTGGAGTTCGTGACCGCCGC
CTGGGGTTGCTCTTCGCGCTAGTGTACCAGGACGACCTCAAGCACTGGCGGCG
  D   P   N   E   K   R   D   H   M   V   L   L   E   F   V   T   A   A>
``` eGFP2as CUCUUCGCGCUAGUGUACCAG (SEQ ID NO:25)

Examples of the different fb hairpin siRNA are described below. Models are presented to show potential folding/base-pairing. Note that fb siRNAs with GFP5 in the name have the same core antisense RNA strand as the GFP5 ds siRNAs, while fb siRNAs with GFP2 in the name have the same core antisense RNA as the GFP2 ds siRNAs.

Partial Foldback Hairpin siRNAs

These foldback hairpin siRNAs have short foldback sequences at both ends, where the ends are not abutted.

GFP2HP1

5' most nucleotide is bold, dashes separate 21 nt core from short extension sequences.

```
GAU-GACCAUGUGAUCGCGCUUCUC-GGAA (SEQ ID NO :26)
``` potential fold:

```
     UGUGAUCGCGCUUCU
   A  |  |||    |||  C
     CCAGUAG   AAAGG
         5'    3'
```

GFP intensity: 3

GFP2HP3

5' most nucleotide is bold, dashes separate 21 nt core from short extension sequences.

```
GGUAG-GACCAUGUGAUCGCGCUUCUC-GGAA (SEQ ID NO: 27)
``` potential fold:

```
     GACCAUGUGAUCGCGCUUCU
   G  |||              |||  C
     AUGG              AAGG
         5'            3'
```

GFP intensity: 1.5-2

GFP2HP3m1

5' most nucleotide and mutation (ag) in bold, dashes separate 21 nt core from short extension sequences.

```
GGUAG-GACCAUGUagUCGCGCUUCUC-GGAA (SEQ ID NO: 28)
``` potential fold:

```
     GACCAUGUagUCGCGCUUCU
   G  |||              |||  C
     AUGG              AAGG
         5'            3'
```

GFP intensity: 5

Demonstrates Sequence Specificity of GFP2HP3.

Partial Foldback Hairpin siRNAs with 3' Extensions

These foldback hairpin siRNAs have their 3' end foldback regions created from non-target matched sequences.

GFP2HP5

```
                                           (SEQ ID NO: 29)
GAU-GACCAUGUGAUCGCGCUUCUC-GUUAUGAACuuuu
``` potential fold:

```
     UGUGAUCGCGCUUCUGUUA
   A  |  |||         |||  U
     CCAgUAG       uuuuCAAG
         5'            3'
```

GFP intensity: 3.5

GFP2HP6

```
                                           (SEQ ID NO:30)
GGUAG-GACCAUGUGAUCGCGCUUCUC-GUUAUGAACuuuu
``` potential fold:

```
     GACCAUGUGAUCGCGCUUCUCGUUA
   G  |||                   |||  U
     AUGG                uuuuCAAG
         5'                  3'
```

GFP intensity: 3

GFP2HP6 m1

```
                                           (SEQ ID NO:31)
GGUAG-GACCAUGUagUCGCGCUUCUC-GUUAUGAACuuuu
``` potential fold:

GFP intensity: 5

Demonstrates sequence specificity of GFP2HP6.

GFP2HP7

```
                                              (SEQ ID NO:32)
GAU-GACCAUGUGAUCGCGCUUCUC-GAAAAGAUGCuuuu
``` potential fold:

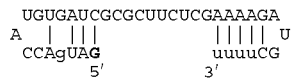

GFP intensity: 3.5

GFP2HP8

A design with a different and longer 3' extension sequence.

```
                                              (SEQ ID NO:33)
GGUAG-GACCAUGUGAUCGCGCUUCUC-GAAAAGAUGCuuuu
``` potential fold:

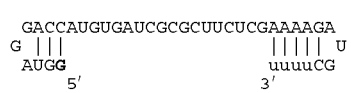

GFP intensity: 4.5

Complete Foldback Hairpin siRNAs

These foldback hairpin siRNAs form a partial duplex with the 5' and 3' ends adjacent to each other.

GFP5HP60tr3

5' most nucleotide is bold. 3 nucleotide complementary strand.

```
      GAAGAAGUCGUGCUGCUUCAU-GGAA    (SEQ ID NO:34)
    5'   GAAGAAGUCGUGCUGCUUCA       (SEQ ID NO:34)
                            ||| U
                        3' AAGG
``` potential fold:

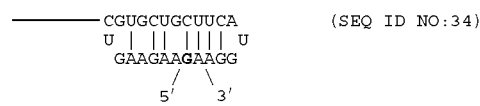

(SEQ ID NO:34)

GFP intensity: 0.5-1

Complete Foldback Hairpin siRNAs with Extensions

These complete foldback hairpin siRNAs have extensions of added bases to create the 5' end foldback.

GFP2HP2

5' most nucleotide is bold, dashes separate 21 nt core from short extension sequences. Note that this design has abutted 5' and 3' ends.

```
5'  GAU-GACCAUGUGAUCGCGCUUCUC-GC 3'   (SEQ ID NO:36)
     |---21nt GFP2 RNA----|
``` potential fold:

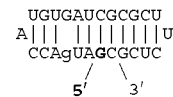

GFP intensity: 1.5

GFP2HP2m1

5' most nucleotide is bold; mismatch mutation in bold (uc) to demonstrate sequence specificity of GFP2HP2. Dashes separate 21 nucleotide core from short extension sequences. Note that this design has abutted 5' and 3' ends and that the mutation is a different sequence than HP3m1 or other GFP2 derived m1 mutations.

```
5'  GGA-GACCAUGUGucCGCGCUUCUC-GC 3'   (SEQ ID NO:37)
     |---21nt GFP2 RNA----|
``` potential fold:

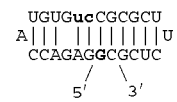

GFP intensity: 5

Example 9

Inhibition of Endogenous Gene Expression by Foldback Hairpin siRNAs Synthesized In Vitro The following experiments show that foldback hairpin siRNA synthesized in vitro can inhibit endogenous genes. The targeted gene is an endogenous neuronal tubulin gene in mouse P19 cells, mouse neuronal beta-tubulin (Beta3 isoform/TuJ1 epitope).

Neuronal tubulin expression was activated by transfection of DNA expression vectors for neural basic-helix-loop-helix transcription factors as described (Farah et al. (2000) Development 127:693-702). Foldback hairpin siRNAs and ds siRNAs were cotransfected with the expression vectors. Expression of the beta-tubulin was assessed by immunohistochemistry of transfected cells with the monoclonal antibody TuJ1 four days after transfection.

Mouse beta3 Tubulin (Also Known as beta4 Tubulin in Humans/Chickens) 3' UTR

```
1550
                                              (SEQ ID NO:38)
...UGUGAGUCCACUUGGCUCUGUCUU...   (mRNA)
   ||||||||||||||||||||||||
3' CACUCAGGUGAACCGAGACAG 5'       (tcRNA)
                                              (SEQ ID NO:39)
```

BT4-1HP3

A partial foldback hairpin siRNA design analogous to GFP2HP3.

GUCGA-GGACAGAGCCAAGUGGACUCA-GUC (SEQ ID NO: 40)

potential fold:

```
        GGACAGAGCCAAGUGGACU
   A |||                 ||| C
     GCUG                CUGA
      5'                  3'
```

TuJ1 inhibition: strong

BT4-1HP3m1

A mismatch mutant to demonstrate the sequence specificity of BT4-1HP3. The 5' end and three base target mismatch (ggu) mutation are shown in bold.

GTCGA-GGACAGAGGGTAGTGGACTCA-GTC (SEQ ID NO: 41)

potential fold:

```
        GGACAGAGgguAGUGGACU
   A |||                 ||| C
     GCUG                CUGA
      5'                  3'
```

TuJ1 inhibition: none

BT4-1HP3U

A partial foldback hairpin siRNA design identical to BT4-1HP3, except it has a 3' extension.

GUCGA-GGACAGAGCCAAGUGGACUCA-GUCuuu (SEQ ID NO: 42)

potential fold:

```
        GGACAGAGCCAAGUGGACU
   A |||        |   ||| C
     GCUG           UUUUCUGA
      5'             3'
```

TuJ1 inhibition: moderate to strong

BT4-1HP6

A different partial foldback hairpin siRNA design.

(SEQ ID NO: 43)
GUCGA-GGACAGAGCCAAGUGGACUCA-GUUAUGAACuuuu potential fold:

```
        GGACAGAGCCAAGUGGACUCAGUUA
   A |||                     |||| U
     GCUG                    UUUUCAAG
      5'                      3'
```

TuJ1 inhibition: slight

BT4-1HP6m1

Mismatch mutation (ggu) in bold. Abolishes inhibition (compare with BT4-1HP6).

(SEQ ID NO: 44)
GUCGA-GGACAGAGgguAGUGGACUCA-GUUAUGAACuuuu potential fold:

```
        GGACAGAGgguAGUGGACUCAGUUA
   A |||                     |||| U
     GCUG                    UUUUCAAG
      5'                      3'
```

TuJ1 inhibition: none

Example 10

Inhibition of Gene Expression by miRNA Precursor-derived siRNAs

In developing a pol II-based system for in vivo expression of an siRNA, microRNA (miRNA) hairpin precursor system was used. The miRNA sequence and its complement was replaced with an siRNA against a target gene of interest.

miRNAs are a class of noncoding RNAs that are encoded as short inverted repeats in the genomes of both invertebrates and vertebrates. These small RNAs are believed to modulate translation of their target RNAs by binding to sites of antisense complementarity in 3' untranslated regions of the targets. miRNAs are typically excised form 60 to 70 nt precursor RNAs, which fold back to form hairpin precursor structures (e.g., as shown in FIG. 11B.) Generally, one of the strands of the hairpin precursor is excised to form the mature miRNA.

The BIC gene was used as one exemplary miRNA. The methods of the present invention may be applied to a variety of miRNAs. Part of the third exon of the BIC gene was used as a starting point for making a miRNA expression vector for siRNAs. The BIC gene is well characterized and has been known to give rise to a noncoding RNA for several years (Tam et al., Mol. Cell. Biol. 17:1490 [1997]; Tam, Gene 274:157 [2001]; Tam et al., J. Virol 76:4275 [2002]). The BIC RNA appears to be a conventional RNA pol II transcribed gene with a poly A tail, although it does not encode a protein. The gene functions as an oncogene in chickens, and expression of the third exon of the gene has been shown to be sufficient for this function. The third exon also has been ectopically expressed using retroviral vectors, indicating that derivatives of this sequence are likely to be suitable for delivery in retroviral vectors. BIC mRNA was recently identified as the probable precursor for the 22 nt miR155 miRNA (Lagos-Quintana et al., Curr Biol. 12:735 [2002]). The miR155 precursor hairpin loop and the conserved sequences near it map to the same region in the third exon that is associated with the oncogene function (Tam, 2001, supra). The hairpin loop containing the miR155 sequence was previously recognized as the most evolutionarily conserved region within the functional domain of BIC (Tam, 2001, supra), consistent with the idea that the BIC oncogene function occurs primarily or exclusively through expression of the encoded miRNA. Because the nucleotide sequences flanking the miR155 hairpin are conserved, these sequences may contribute to the processing of the miR155 precursor. While the present invention is not limited to any particular mechanism, one model is that that a short hairpin precursor containing the miR155 sequence and adjacent sequences is excised from the initial BIC transcript, with the excised hairpin being essentially analogous to the U6-expressed hairpin siRNAs described above. This precursor is likely processed by the Dicer endonuclease to release the miR155 miRNA.

In constructing the siRNA expression construct, the portion of third exon of the mouse BIC gene comprising the miR155 hairpin precursor and the conserved flanking sequences was isolated by PCR from genomic DNA. FIG. 11 (A) shows the primers used for amplifying a 471 nt fragment (457 nt+restriction sites) from mouse BIC exon 3.

A DNA expression vector, CS2+BIC, was constructed that contains the third exon of mouse BIC in an unmodified form under the control of a simian CMV (sCMV) promoter, followed by an SV40 late polyadenylation site in the CS2 vector (Turner and Weintraub, Genes Dev. 8:1434 [1994]). The RNA from the CS2+BIC vector is processed to release the miR155 miRNA. A target for the miR155 miRNA was also constructed, wherein the complement of the miR155 RNA was inserted into the 3' untranslated region of a luciferase gene in the CS2 vector, denoted "CS2+luc-miR155 as."

A lucifierase reporter construct (See Example 6) was used to assess the effect of the miR155 miRNA on the expression of the luciferase reporter. The CS2+luc-miR155 as target vector was cotransfected with either the CS2-BIC vector, or with the eGFPbgl2 vector, as a control. Expression from the eGFPbgl2 vector would not be expected to have any affect on luciferase activity. The luciferase activity was reduced by cotransfection of the target vector with the CS2-+BIC vector, compared to the control. (FIG. 13A). This indicates that the CS2+BIC vector is functional and produces the miR155 miRNA, and that this miRNA can inhibit a target gene that contains a matching sequence. While the invention is not limited to any particular mechanism, we expect that this inhibition is an siRNA-like effect (i.e., destruction of the target RNA), rather than inhibition of translation as has generally been reported for miRNAs. miRNA inhibition typically works through partially matched sequences, and does not involve RNA destruction. In contrast, the CS2+luc-miR155 as target created for miR155 is an exact sequence match, which would be expected to lead to RNA destruction of the target message by the miRNA.

The effects of variations in the conserved sequences flanking the miR155 precursor were examined. Truncation of the BIC exon sequences in CS2+BIC by removal of sequences 3' to the Stu1 site located just after the hairpin precursor (see FIG. 11C) to create the vector "CS2+BIC-short" substantially reduced inhibition of the luciferase activity expressed from the CS2+luc-miR155 as target (FIG. 13C), indicating that sequences outside of the short hairpin precursor for miR155 are required for efficient function. While the invention is not limited to any particular mecha-nism, these sequences may contribute to the processing of the long RNA containing BIC to lead to release of a short hairpin precursor.

This approach to expression of siRNAs can be generalized to target other RNAs in vivo. This was demonstrated as follows.

A derivative of the CS2+BIC vector was made, wherein the hairpin loop containing the miR155 sequence was replaced by two inverted Bbs1 restriction sites (FIG. 11C). This allows other hairpin sequences to be precisely inserted into the BIC RNA, replacing the original miR155 hairpin precursor sequence. This vector is designated "CS2+BIC23." (While the vector also includes about 100 nucleotides of phage lambda DNA inserted 5' to the BIC sequences, these lambda sequences apper to have no effect on function.)

A sequence complementary to a 22 nt sequence in the 3' untranslated region (UTR) of the mouse neuroD1 mRNA was inserted in the CS2+BIC23 vector, in place of the miR155 sequence (CS2+BIC23-ND1BHP1) (FIG. 12). The sequence of the complementary strand of the hairpin precursor was adjusted to match the neuroD1 sense sequence, but mismatches and missing bases analogous to those present in the miR155 hairpin precursor were included (as indicated in "ND1BHP1," FIG. 12). A second version was created in which most of the missing bases and mismatches from the sense sequence of the hairpin precursor were replaced with precisely matched bases (CS2+BIC23-ND1BHP2) (as shown in "N1BHP2," FIG. 12). A luciferase reporter was also constructed wherein the 3' UTR from the neuroD1 mRNA was inserted 3' of the luciferase coding region (CS2+luc-ND1UTR). When this reporter construct was co-transfected with either the CS2+BIC23-ND1BHP1 or the CS2+BIC23-ND1BHP2 vector, luciferase activity was decreased, indicating that these vectors are producing the desired siRNAs against the neuroD1 gene (FIG. 13B). This inhibition is specific, since luciferase expression from the CS2+luc-miR155 as vector, which lacks the ND1UTR target sequence, was not inhibited by cotransfection with the CS2+BIC23-ND1BHP1 vector (FIG. 13A).

The CS2+BIC23 vector has also been used to construct a vector that includes a 22 nt siRNA targeted a neuronal specific tubulin and have observed inhibition of the endogenous neuronal specific tubulin protein in transfected mouse P19 cells, essentially as we have previously described for the U6 promoter-driven hairpin siRNA vectors.

Beyond the advantages of using RNA pol II, this should also allow the production of multiple siRNAs from a single transcript, since there are examples of multiple miRNA hairpin precursors embedded within a single long RNA. It is also expected that the coding region for a marker gene (e.g GFP or lacZ) can be incorporated into the same RNA pol II RNA as the miRNA/siRNA precursors (e.g., an mRNA for GFP could also encode an siRNA precursor). This would facilitate identification of the cells in which the siRNA was expressed.

Expression of one (or several) BIC siRNA cassettes from the 3' UTR of an mRNA for a selectable marker protein (e.g. puromycin resistance) allows direct selection of cells expressing the siRNA(s) with an appropriate drug (e.g., puromycin). This is useful for producing cell lines that have specific genes inhibited.

This approach can also be extended to other applications, including gene replacement. For example, the coding region of the mRNA can encode a modified version of the endogenous gene targeted by the siRNA, but without the siRNA target sequence (the target sequence could either be altered or deleted to prevent inhibition of the introduced version). For example, siRNAs targeted against the 3' UTR of the endogenous gene are present on a transcript that contains a modified coding region for the target gene's product, without the 3' UTR.

Alternately, other functional protein(s) might be expressed from the same transcript as one or more BIC siRNA cassettes, unrelated to either selection or gene replacement.

The 471 nt fragment from BIC was inserted into the 3' UTR of the GFP gene in CS2+eGFPbgl2. This construct still produces GFP by fluorescence, and it can inhibit the CS2+ luc-miR155 as target in a cotransfection assay (FIG. 3C).

The BIC23-ND1BHP1 sequence (without the lambda 5' extension) and other BIC23 derivatives producing siRNAs against other target sequences were inserted into a retroviral vector that also expresses a GFP marker, RG3, and we are presently testing the ability of these vectors to inhibit specific target genes in infected cells. We expect that these vectors will allow efficient transfer of hairpin siRNAs into mammalian cells in vitro and in vivo, and will permit the production of stable cell lines.

A plasmid vector that contains the 471 nt BIC/miR155 precursor in tandem with the ND1BHP1 sequence for inhibition of both the miR155 target (CS2+luc-miR155as) and (CS2+luc-ND1UTR) is also tested. It is contemplated that this type of vector will be able to be used to inhibit two or more target genes simultaneously.

In some embodiments, the complimentary strand for an siRNA is designed to mimic the structure and base-pairing of the original miR-155 hairpin precursor (or other construct) (see experiments on pages 123-129). The data generated with such constructs highlights that the antisense strand bulges (e.g., the two missing bases in the sense strand), showing a contribution to strand specificity for the siRNA, although the present invention is not limited to any particular mechanism of action. In some embodiments, G:U base pairs or similar mismatches are used in this region.

Example 11

A Smaller Domain of BIC RNA is Sufficient for miR155 or Synthetic siRNA inhibition Initial constructs based on the mouse BIC gene included BIC sequences from ~163 nt 5' to the miR155 miRNA sequence to ~372 nt 3' to miR155. Standard molecular biology techniques were used to construct shorter versions of this region in the CS2+ expression vector. Their ability to inhibit a reporter gene was assessed in a cotransfection assay. A construct, CS2+BICsh ("short"), with only 150 nt of the BIC RNA (28 nt 5' to the miR155 sequence, the 22 nt miR155 sequence, and 100 nt 3' to miR155) was able to inhibit the reporter as or more effectively than the original longer BIC construct. Deletion of the last 50 nt of this construct (at the Stu1 site as described above) greatly reduces its inhibition of the reporter, indicating that functionally required sequences exist between nt 100 and 150. The sequence of this region is shown below (SEQ ID NO:45):

```
CUGGAGGCUUGCUGAAGGCUGUAUGCUGUUAAUGCUAAUUGUGAUAGGGG

UUUUGGCCUCUGACUGACUCCUACCUGUUAGCAUUAACAGGACACAAGGC

CUGUUACUAGCACUCACAUGGAACAAAUGGCCACCGUGGGAGGAUGACAA
```

This is a BIC sequence that is expressed in the CS2+BICsh vector. The miR155 sequence is underlined. The expressed RNA also includes additional vector derived sequences both 5' and 3' to the above sequence.

A derivative of CS2+BIC23-ND1BHP1 in which the BIC sequences flanking the modified ND1BHP1 hairpin were reduced to the shorter sequences as described above was constructed by PCR amplifcation of CS2+BIC23-ND1BHP1 with appropriate primers and insertion of this product into CS2+. This CS2+BIC23-ND1BHP1sh construct inhibited luciferase expression from a reporter gene contruct more effectively than the original CS2+BIC23-ND1BHP1 in a cotransfection assay. Transfections were performed essentially as described in Yu et al., PNAS 99:6047 [2002] or Yu et al., Mol. Therapy 7:228 [2003].

CS2+BIC23-ND1BHP3, a similar construct to CS2+BIC23-ND1BHP1, but targeted against a different sequence in the neuroD mRNA, also inhibited luciferase expression from a reporter gene construct in a cotransfection assay, to a similar degree as CS2+BIC23-ND1BHP1. The shorter version of this construct, CS2+BIC23-ND1BHP3sh, created PCR as described above for CS2+BIC23-ND1BHP1sh, also inhibited luciferase in a cotransfection assay, more effectively than the original CS2+BIC23-ND1BHP3.

(SEQ ID NO:46)
```
UUUCUAAGCACUUUUCUGCUGGUU--UUGGC
|||||||||||| : | ||||:||:  |::| C
AAAGAUUCGUG-GCA-ACGAUCAGUCAGUCU
```

This is the predicted folded structure of the hairpin region of the BIC23-ND1BHP3 precursor RNA. The siRNA sequence complementary to the neuroD13' UTR is underlined.

Cooperative Inhibition of a Single Gene with Two BIC-Derived siRNAs

It is expected that production of siRNAs/hairpin siRNAs/BIC-derived siRNAs directed against two different sequences within the same target gene will increase the inhibition of that target gene. Cotransfection of the CS2+BIC23-ND1BHP1 and CS2+BIC23-ND1BHP3 vectors with a reporter construct inhibited expression to a greater degree than either of the individual CS2+BIC23-ND1BHP1 and CS2+BIC23-ND1BHP3 vectors. A similar cooperative inhibition was observed by cotransfection of CS2+BIC23-ND1BHP1sh and CS2+BIC23-ND1BHP3sh with the reporter.

Example 12

Additional Mapping of the Minimal Domain of BIC Required for miRNA Production

Expression of a 150 nt fragment of BIC in mammalian cells is sufficient for production of miR-155 and this fragment can be engineered to produce siRNAs (the SIBR cassette). A 99 nt version, truncated on the 3' end, is not effective.

Additional 3' end truncations were generated by standard molecular biology techniques. Production of miR-155 was assessed by cotransfection of the new vectors with a luciferase miR-155 antisense reporter (luc-miR155 as) followed by a luciferase assay, as we have described for previous deletion analysis of BIC. The shortest new deletion tested, a 111 nt version of BIC, led to inhibition of the luc-miR155 as reporter to a similar extent as the 150 nt version of BIC. This indicates that some of the evolutionarily conserved sequences located 3' to the miR-155 hairpin precursor within the 150 nt fragment are not required for miR-155 production/function. The 111 nt fragment is the smallest domain of BIC tested that is sufficient for miR-155 production, and shows that the minimal effective fragment typically has a 3' end at most 11 nt shorter than this fragment. This 111 nt domain contains a predicted duplex region adjacent to the predicted miR-155 hairpin that is partially disrupted in the 99 nt version of BIC. The putative extended duplex structure may be necessary for Drosha processing in cells, although other explanations are also possible, although the present invention is not so limited.

It is contemplated that the 111 nt BIC sequence is able to produce siRNAs if the miR-155 sequence and its complement are replaced with an appropriate sequence, as we have described for the 150 nt and longer fragments of BIC. We expect that such siRNA cassettes will function in any context in which the larger BIC-derived cassettes can function.

The 150 nt "short BIC" domain (basis for SIBR cassette) sequence is shown below (SEQ ID NO:47):

CTGGAGGCTTGCTGAAGGCTGTATGCTGTTAATGCTAATTGTGATAGGGG

TTTTGGCCTCTGACTGACTCCTACCTGTTAGCATTAACAGGACACAAGGC

CTGTTACTAGCACTCACATGGAACAAATGGCCACCGTGGGAGGATGACAA

The sequence of the 99 nt non-functional version (also known as BIC deletion or BICstu), with the 3' end at the Stu1 cut site, is shown below (SEQ ID NO: 48'):

CTGGAGGCTTGCTGAAGGCTGTATGCTGTTAATGCTAATTGTGATAGGGG

TTTTGGCCTCTGACTGACTCCTACCTGTTAGCATTAACAGGACACAAGG

The sequence of the 111 nt shortest functional version of BIC is (SEQ ID NO:49):

CTGGAGGCTTGCTGAAGGCTGTATGCTGTTAATGCTAATTGTGATAGGGG

TTTTGGCCTCTGACTGACTCCTACCTGTTAGCATTAACAGGACACAAGGC

CTGTTACTAGC

Similar techniques may be used to generate constructs for other miRNAs.

Example 13

Inhibition of Two Genes with a Dual BIC Construct

It is expected that expression of two or more copies of BIC-derived hairpin precursors (and flanking sequences) can be expressed within a single RNA to generate two or more siRNAs simultaneously. Such a vector can be used to inhibit two or more target genes simultaneously, and/or to produce multiple siRNAs against a single target, to increase the efficiency of inhibition of that target.

To test the feasibility of this approach, a vector was constructed that could inhibit two different genes simultaneously. The BIC sequences from the CS2+BIC vector were inserted immediately after (3') to the BIC23-ND1BHP1 insert in CS2+BIC23-ND1BHP1. The resulting vector, CS2+BIC23-ND1BHP1-BIC, expresses both the ND1BHP1 version of BIC and the original BIC in tandem from a single RNA. This vector can effectively inhibit a reporter construct in a cotransfection assay. This experiments demonstrates that the dual construct can inhibit reporters for either of two different targets: the luc-neuro-D-UTR reporter or the BIC (luc-miR155 as).

Transfections were performed essentially as described in Yu et al., PNAS 99:6047 [2002] or Yu et al., Mol. Therapy 7:228 [2003].

Typical DNA amounts for one well of 12 well cluster are:
BIC constructs: 200-400 ng
Gal4-UAS or CS2+luciferase reporter (with or without siRNA target sequences): 100-250 ng
Gal4-ER activator plasmid (for inducible reporter): 100 ng
LacZ plasmid (for transfection normalization): 50 ng
Other amounts may also be used.

In some experiments, inducible luciferase reporters driven by a Gal4 UAS rather than the CS2 luciferase reporter constructs are used. The inducible reporters are activated by a cotransfected gal4-ER activator plasmid that produces a gal4 activator that is active in the presence of 4-OH tamoxifen (Yu et al., 2003, supra). The inducible luciferase reporters allow the siRNA to be expressed prior to target RNA expression, thereby more accurately reflecting target inhibition. However, inhibition can be demonstrated with either inducible or constitutive (e.g., CS2) reporters.

Example 14

RNA pol II miRNA/siRNA Expression Vector Design

This Example describes exemplary designs for RNA polII expression vectors.

Shown below is miR155 precursor (mBIC) folded hairpin (located within a much longer RNA polII transcript); miR155 is underlined (SEQ ID NO:50):

```
5'   ...GCUGUUAAUGCUAAUUGUGAUAGGGGUU--UUGGC
        ||||||||||||||: : |  ||||:||:   |::| C
3'   ...GGACAAUUACGAUUG-UCC-AUCCUCAGUCAGUCU
```

ND1BHP1 RNA Folded (an Effective neuroD siRNA Replaces miR155) (SEQ ID NO: 51):

```
5'   ...UUGCAGCAAUCUUAGCAAAAGGUU--UUGGC
        ||||||||||||| :|| ||||:||:   |::| C
3'   ...AACGUCGUUAG-gUC-UUUUuCAGUCAGUCU
```

Both the miRNA sequence and its complementary sequence have been changed, but not the loop sequence. In some embodiments, a UUN$_{18}$GG format for siRNAs is used (SEQ ID NO:52):

```
5'   ...UUNNNNNNNNNNNNNNNNNNNGGUU--UUGGC
        ||||||||||||| :|| ||||:||:   |::| C
3'   ...AANNNNNNNNNN-NNN-NNNNUCAGUCAGUCU
```

The underlined sequence is the antisense siRNA. The UU and/or GG at the ends and/or the G:U basepair near the 3' end may contribute to efficiency of processing. UN$_{18}$AG also works, while UCN$_{18}$AG does not work well. The gaps (missing bases) in the complementary "sense" strand are not required, but including the gaps improved efficacy. The position of the central G:U basepair is moved to accommodate the particular siRNA sequence. It is preferred that the G:U is away from the 5' end of the siRNA.

It is preferred that the DNA template include both strands of the hairpin (underlined), the loop, and overhangs compatible with the Bbs1 cloning sites at each end:

64 nt DNA template oligos:

```
(miRNA/siRNA strand; (SEQ ID NO:53) (complementary strand; SEQ ID NO:54)
5' GCTGTTNNNNNNNNNNNNNNNNNNNGGTTTTGGCCTCTGACTGACTNNNN-NNN-NNNNNNNNNAAC    3'
3'     AANNNNNNNNNNNNNNNNNNNCCAAAACCGGAGACTGACTGANNNN-NNN-NNNNNNNNNNTTGTCCT 5'
```

The 4 nt overhangs match the inverted Bbs1 sites in the vector (below). No 5' phosphates are required for the oligos since the cut vector has 5' phosphates. The G-C basepair (bold) at the 3' end of this cassette is part of the BIC stem-loop structure and should be included in the oligo sequences. The miRNA/siRNA and its complement are underlined.

Example: ND1BHP1 DNA template oligos (SEQ ID NO:55 (sense strand) and SEQ ID NO:56 (complementary strand)

```
5' GCTGTTGCAGCAATCTTAGCAAAAGGTTTTGGCCTCTGACTGACTTTTT-CTG-GATTGCTGCAAC    3'
3'     AACGTCGTTAGAATCGTTTTCCAAAACCGGAGACTGACTGAAAAA-GAC-CTAACGACGTTGTCCT 5'
``` mBIC siRNA hairpin cloning site (uses 2 inverted Bbs1 sites) (SEQ ID NO: 57):

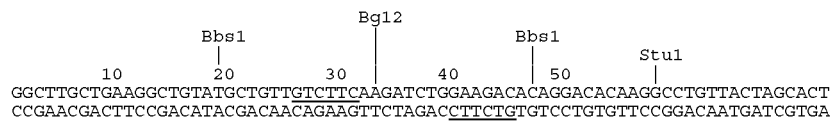

```
           Bbs1        Bgl2          Bbs1
            |           |             |           Stu1
     10    20    30    40    50      |
GGCTTGCTGAAGGCTGTATGCTGTTGTCTTCAAGATCTGGAAGACACAGGACACAAGGCCTGTTACTAGCACT
CCGAACGACTTCCGACATACGACAACAGAAGTTCTAGACCTTCTGTGTCCTGTGTTCCGGACAATGATCGTGA
```

Bbs1 cut:

```
                                       (SEQ ID NO:58)
        GGCTTGCTGAAGGCTGTAT (SEQ ID NO:60)
        AGGACACAAGGCCTGTTACTAGCACT (SEQ ID NO:59)
        CCGAACGACTTCCGACATACGAC (SEQ ID NO:170)
        GTGTTCCGGACAATGATCGTGA (SEQ ID NO:171)
            GCTGNNNNNNNNNNN . . . NNNNNNNNNNNC (SEQ ID NO:172)
                NNNNNNNNNNN . . . NNNNNNNNNNNNGTCCT
```

(miRNA/siRNA DNA template with compatible ends)

The two Bbs1 sites (recognition sites underlined) yield non-compatible overhanging ends, so the vector cannot recircularize when completely digested with Bbs1. Digestion with Bgl2 can be used to reduce any background arising from incomplete Bbs1 digestion of the vector if needed.

Bgl2 (and Stu1) are unique in the vector. For colony testing, the band from PCRing across the cloning site will increase by ~35 nt after correct insertion of a DNA template for an siRNA.

These constructs are suitable for targeting coding regions or UTRs. When using the UUN$_{18}$GG format, target sites within the gene of interest of the form CCN$_{18}$AA in the sense strand are used for targeting. If CCN$_{18}$AA is not suitable, CTN$_{18}$AA can be used.

Example 15

The SIBR Cassette Functions Within an Intron or Within the Untranslated Region of a Protein-encoding mRNA Predicted miRNA precursors are known to be located in introns for several spliced RNAs. Since the first step of miRNA processing is believed to occur in the nucleus, it is plausible that miRNAs can be derived from intronic sequences within transcribed RNAs by processing (by Drosha) before, or more likely after, splicing. One or two SIBR cassettes is located within an intron of a spliced mRNA or within the untranslated region of an mRNA that encodes a protein. Expression leads to effective inhibition of a target gene. In both situations, a protein encoded by the same transcript is also expressed, although the protein level may be decreased. Location of the SIBR cassette(s) within in an intron interferes with protein expression to a lesser extent than location within the untranslated region. In some embodiments, more than two SIBR cassettes within a single transcript are used, including within an intron or untranslated region.

The utility of these two types of designs is that either can be used to express a protein in the same cells in which the SIBR cassette is used to inhibit gene expression. The combination of one (or more) SIBR cassettes with a protein allows concomitant SIBR expression/inhibition and protein expression. These approaches are extended to the expression of multiple proteins from the single transcription unit by using internal ribosome entry site(s) to express additional proteins from the mature mRNA.

Example 16

Use of BIC Based Vectors

SiRNA expression vectors based upon BIC RNA that utilize RNA pol II promoters (SIBR vectors) were generated. A simian CMV promoter was utilized. The vectors were used to express siRNAs against POSH, an SH3 containing protein that mediates interactions between Akt2 and the JNK signaling pathways (Tapon et al., EMBO J. 17:395 [1998]; Figueroa et al., J. Biol. Chem. 278:47922 [2003]). The C-terminus of POSH also interacts with actin binding proteins. POSH mRNA is expressed during neural development in the mouse.

The vectors were found to inhibit expression of endogenous POSH protein in mouse P19 cells. The expression of tandem SIBR cassettes with different siRNAs against POSH (POSH 1+2) from a single vector further reduces expression.

Reduction of POSH expression using RNAi during neuronal differentiation of P19 cells cotransfected with expression vectors for the bHLH protein ngn1 and GFP leads to enhanced neurite/axon outgrowth (faster growth and longer processes).

Coexpression of a POSH cDNA without the 3' UTR in combination with the POSH 1+2 SIBR vector was found to return process lengths to near wild-type levels.

Expression of SIBR POSH 1+2 was also shown to lead to enhanced process outgrowth in primary neurons derived from embryonic mouse cortical progenitors differentiated in vitro.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant field are intended to be within the scope of the following claims.

SEQUENCE LISTING

```
<160> NUMBER OF SEQ ID NOS: 172

<210> SEQ ID NO 1
<211> LENGTH: 29
<212> TYPE: DNA
<213> ORGANISM: Mus musculus

<400> SEQUENCE: 1
cccaagctta tccgacgccg ccatctcta                                    29

<210> SEQ ID NO 2
<211> LENGTH: 35
<212> TYPE: DNA
<213> ORGANISM: Mus musculus

<400> SEQUENCE: 2
gggatccgaa gaccacaaac aaggcttttc tccaa                             35

<210> SEQ ID NO 3
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: These residues represent ribonucleotides
      complementary to target RNA
<220> FEATURE:
<221> NAME/KEY: misc_feature
<222> LOCATION: (20)..(22)
<223> OTHER INFORMATION: n is a, c, g, or u
<220> FEATURE:
<221> NAME/KEY: misc_feature
<222> LOCATION: (23)..(41)
<223> OTHER INFORMATION: These residues represent ribonucleotides
      complementary to the N-strand.
<220> FEATURE:
<221> NAME/KEY: misc_feature
<222> LOCATION: (42)..(43)
<223> OTHER INFORMATION: n is a, c, g, or u
```

-continued

```
<400> SEQUENCE: 3
nnnnnnnnnn nnnnnnnnnn nnnnnnnnnn nnnnnnnnnn nnn         43

<210> SEQ ID NO 4
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: These residues are representative of added
      nucleotides in each addition.
<220> FEATURE:
<221> NAME/KEY: misc_feature
<222> LOCATION: (4)..(27)
<223> OTHER INFORMATION: n is a, c, g, or u
<220> FEATURE:
<221> NAME/KEY: misc_feature
<222> LOCATION: (28)..(30)
<223> OTHER INFORMATION: These residues are representative of added
      nucleotides in each addition.

<400> SEQUENCE: 4
nnnnnnnnnn nnnnnnnnnn nnnnnnnnnn                         30

<210> SEQ ID NO 5
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: These residues represent ribonucleotides added
      to create base pairs near the ends of the foldback RNA and which
      are not necessarily complementary to the target RNA.
<220> FEATURE:
<221> NAME/KEY: misc_feature
<222> LOCATION: (4)..(6)
<223> OTHER INFORMATION: These residues represent ribonucleotides of a
      loop region, which are not necessarily complementary to the target
      RNA.
<220> FEATURE:
<221> NAME/KEY: misc_feature
<222> LOCATION: (7)..(9)
<223> OTHER INFORMATION: These residues represent ribonucleotides added
      to create base pairs near the ends of the foldback RNA and which
      are not necessarily complementary to the target RNA.
<220> FEATURE:
<221> NAME/KEY: misc_feature
<222> LOCATION: (10)..(33)
<223> OTHER INFORMATION: n is a, c, g, or u
<220> FEATURE:
<221> NAME/KEY: misc_feature
<222> LOCATION: (34)..(36)
<223> OTHER INFORMATION: These residues represent ribonucleotides added
      to create base pairs near the ends of the foldback RNA and which
      are not necessarily complementary to the target RNA.
<220> FEATURE:
<221> NAME/KEY: misc_feature
<222> LOCATION: (37)..(39)
<223> OTHER INFORMATION: These residues represent ribonucleotides of a
      loop region, which are not necessarily complementary to the target
      RNA.
<220> FEATURE:
<221> NAME/KEY: misc_feature
<222> LOCATION: (40)..(42)
<223> OTHER INFORMATION: These residues represent ribonucleotides added
      to create base pairs near the ends of the foldback RNA and which
      are not necessarily complementary to the target RNA.

<400> SEQUENCE: 5
```

```
nnnnnnnnnn nnnnnnnnnn nnnnnnnnnn nnnnnnnnnn nn          42

<210> SEQ ID NO 6
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: n is a, c, g, or u

<400> SEQUENCE: 6
nnnnnnnnnn nnnnnnnnnn nn                                 22

<210> SEQ ID NO 7
<211> LENGTH: 26
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(26)
<223> OTHER INFORMATION: n is a, c, g, or u

<400> SEQUENCE: 7
nnnnnnnnnn nnnnnnnnnn nnnnnn                             26

<210> SEQ ID NO 8
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: n is a, c, g, or u

<400> SEQUENCE: 8
nnnnnnnnnn nnnnnnnnnn nnnnnnnnnn nnnn                    34

<210> SEQ ID NO 9
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: n is a, c, g, or u
<220> FEATURE:
<221> NAME/KEY: misc_feature
<222> LOCATION: (32)..(32)
<223> OTHER INFORMATION: This residue is a non-paired base.
<220> FEATURE:
<221> NAME/KEY: misc_feature
<222> LOCATION: (42)..(43)
<223> OTHER INFORMATION: n is a, c, g, or u

<400> SEQUENCE: 9
nnnnnnnnnn nnnnnnnnnn nnccccccccc cncccccccc cnn         43

<210> SEQ ID NO 10
<211> LENGTH: 47
<212> TYPE: RNA
```

```
<213> ORGANISM: Artificial Sequence
<220> FEATURE:
<223> OTHER INFORMATION: Synthetic

<400> SEQUENCE: 10
gaagaagucg ugcugcuuca ugggggaagca gcaggacuuc uucuuuu          47

<210> SEQ ID NO 11
<211> LENGTH: 63
<212> TYPE: RNA
<213> ORGANISM: Artificial Sequence
<220> FEATURE:
<223> OTHER INFORMATION: Synthetic

<400> SEQUENCE: 11
gacuugaaga agucgugcug cuucaugugg gacaugaagc agcaucacuu cuucaagucu    60
uuu                                                                 63

<210> SEQ ID NO 12
<211> LENGTH: 62
<212> TYPE: RNA
<213> ORGANISM: Artificial Sequence
<220> FEATURE:
<223> OTHER INFORMATION: Synthetic

<400> SEQUENCE: 12
gacuugaaga agucgugcug cucaugugggg acaugaagca gcaucacuuc uucaagucuu   60
uu                                                                  62

<210> SEQ ID NO 13
<211> LENGTH: 21
<212> TYPE: RNA
<213> ORGANISM: Artificial Sequence
<220> FEATURE:
<223> OTHER INFORMATION: Synthetic

<400> SEQUENCE: 13
gaagaagucg ugcugcuuca u                                             21

<210> SEQ ID NO 14
<211> LENGTH: 21
<212> TYPE: RNA
<213> ORGANISM: Artificial Sequence
<220> FEATURE:
<223> OTHER INFORMATION: Synthetic

<400> SEQUENCE: 14
gaagcagcac gacuucuucu u                                             21

<210> SEQ ID NO 15
<211> LENGTH: 21
<212> TYPE: RNA
<213> ORGANISM: Artificial Sequence
<220> FEATURE:
<223> OTHER INFORMATION: Synthetic

<400> SEQUENCE: 15
gaagaagucc agcugcuuca u                                             21

<210> SEQ ID NO 16
<211> LENGTH: 21
<212> TYPE: RNA
<213> ORGANISM: Artificial Sequence
<220> FEATURE:
<223> OTHER INFORMATION: Synthetic
```

```
<400> SEQUENCE: 16
gaagcagcug gacuucuucu u                                              21

<210> SEQ ID NO 17
<211> LENGTH: 21
<212> TYPE: RNA
<213> ORGANISM: Artificial Sequence
<220> FEATURE:
<223> OTHER INFORMATION: Synthetic

<400> SEQUENCE: 17
gaccauguga ucgcgcuucu c                                              21

<210> SEQ ID NO 18
<211> LENGTH: 21
<212> TYPE: RNA
<213> ORGANISM: Artificial Sequence
<220> FEATURE:
<223> OTHER INFORMATION: Synthetic

<400> SEQUENCE: 18
uucugguaca cuagcgcgaa g                                              21

<210> SEQ ID NO 19
<211> LENGTH: 41
<212> TYPE: DNA
<213> ORGANISM: Artificial Sequence
<220> FEATURE:
<223> OTHER INFORMATION: Synthetic

<400> SEQUENCE: 19
taccccgacc acatgaagca gcacgacttc ttcaagtccg c                        41

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

Tyr Pro Asp His Met Lys Gln His Asp Phe Phe Lys Ser Ala
1               5                   10

<210> SEQ ID NO 21
<211> LENGTH: 21
<212> TYPE: RNA
<213> ORGANISM: Artificial Sequence
<220> FEATURE:
<223> OTHER INFORMATION: Synthetic

<400> SEQUENCE: 21
gaagaagucg ugcugcuuca u                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic

<400> SEQUENCE: 22
gaagaagucc agcugcuuca u                                              21
```

<210> SEQ ID NO 23
<211> LENGTH: 53
<212> TYPE: DNA
<213> ORGANISM: Artificial Sequence
<220> FEATURE:
<223> OTHER INFORMATION: Synthetic

<400> SEQUENCE: 23
gaccccaacg agaagcgcga tcacatggtc ctgctggagt tcgtgaccgc cgc          53

<210> SEQ ID NO 24
<211> LENGTH: 18
<212> TYPE: PRT
<213> ORGANISM: Artificial Sequence
<220> FEATURE:
<223> OTHER INFORMATION: Synthetic

<400> SEQUENCE: 24

Asp Pro Asn Glu Lys Arg Asp His Met Val Leu Leu Glu Phe Val Thr
1                 5                   10                 15

Ala Ala

<210> SEQ ID NO 25
<211> LENGTH: 21
<212> TYPE: RNA
<213> ORGANISM: Artificial Sequence
<220> FEATURE:
<223> OTHER INFORMATION: Synthetic

<400> SEQUENCE: 25
cucuucgcgc uaguguacca g                                            21

<210> SEQ ID NO 26
<211> LENGTH: 28
<212> TYPE: RNA
<213> ORGANISM: Artificial Sequence
<220> FEATURE:
<223> OTHER INFORMATION: Synthetic

<400> SEQUENCE: 26
gaugaccaug ugaucgcgcu ucucggaa                            28

<210> SEQ ID NO 27
<211> LENGTH: 30
<212> TYPE: RNA
<213> ORGANISM: Artificial Sequence
<220> FEATURE:
<223> OTHER INFORMATION: Synthetic

<400> SEQUENCE: 27
gguaggacca ugugaucgcg cuucucggaa                        30

<210> SEQ ID NO 28
<211> LENGTH: 30
<212> TYPE: RNA
<213> ORGANISM: Artificial Sequence
<220> FEATURE:
<223> OTHER INFORMATION: Synthetic

<400> SEQUENCE: 28
gguaggacca uguagucgcg cuucucggaa                        30

<210> SEQ ID NO 29
<211> LENGTH: 37
<212> TYPE: RNA
<213> ORGANISM: Artificial Sequence

```
<220> FEATURE:
<223> OTHER INFORMATION: Synthetic

<400> SEQUENCE: 29
gaugaccaug ugaucgcgcu ucucguuaug aacuuuu                                37

<210> SEQ ID NO 30
<211> LENGTH: 39
<212> TYPE: RNA
<213> ORGANISM: Artificial Sequence
<220> FEATURE:
<223> OTHER INFORMATION: Synthetic

<400> SEQUENCE: 30
gguaggacca ugugaucgcg cuucucguua ugaacuuuu                              39

<210> SEQ ID NO 31
<211> LENGTH: 39
<212> TYPE: RNA
<213> ORGANISM: Artificial Sequence
<220> FEATURE:
<223> OTHER INFORMATION: Synthetic

<400> SEQUENCE: 31
gguaggacca uguagucgcg cuucucguua ugaacuuuu                              39

<210> SEQ ID NO 32
<211> LENGTH: 38
<212> TYPE: RNA
<213> ORGANISM: Artificial Sequence
<220> FEATURE:
<223> OTHER INFORMATION: Synthetic

<400> SEQUENCE: 32
gaugaccaug ugaucgcgcu ucucgaaaag augcuuuu                               38

<210> SEQ ID NO 33
<211> LENGTH: 40
<212> TYPE: RNA
<213> ORGANISM: Artificial Sequence
<220> FEATURE:
<223> OTHER INFORMATION: Synthetic

<400> SEQUENCE: 33
gguaggacca ugugaucgcg cuucucgaaa agaugcuuuu                             40

<210> SEQ ID NO 34
<211> LENGTH: 25
<212> TYPE: RNA
<213> ORGANISM: Artificial Sequence
<220> FEATURE:
<223> OTHER INFORMATION: Synthetic

<400> SEQUENCE: 34
gaagaagucg ugcugcuuca uggaa                                             25

<210> SEQ ID NO 35

<400> SEQUENCE: 35

000

<210> SEQ ID NO 36
<211> LENGTH: 26
<212> TYPE: RNA
<213> ORGANISM: Artificial Sequence
```

```
<220> FEATURE:
<223> OTHER INFORMATION: Synthetic

<400> SEQUENCE: 36
gaugaccaug ugaucgcgcu ucucgc                                         26

<210> SEQ ID NO 37
<211> LENGTH: 26
<212> TYPE: RNA
<213> ORGANISM: Artificial Sequence
<220> FEATURE:
<223> OTHER INFORMATION: Synthetic

<400> SEQUENCE: 37
ggagaccaug uguccgcgcu ucucgc                                         26

<210> SEQ ID NO 38
<211> LENGTH: 24
<212> TYPE: RNA
<213> ORGANISM: Artificial Sequence
<220> FEATURE:
<223> OTHER INFORMATION: Synthetic

<400> SEQUENCE: 38
ugugagucca cuuggcucug ucuu                                           24

<210> SEQ ID NO 39
<211> LENGTH: 21
<212> TYPE: RNA
<213> ORGANISM: Artificial Sequence
<220> FEATURE:
<223> OTHER INFORMATION: Synthetic

<400> SEQUENCE: 39
gacagagcca aguggacuca c                                              21

<210> SEQ ID NO 40
<211> LENGTH: 29
<212> TYPE: RNA
<213> ORGANISM: Artificial Sequence
<220> FEATURE:
<223> OTHER INFORMATION: Synthetic

<400> SEQUENCE: 40
gucgaggaca gagccaagug gacucaguc                                      29

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
gtcgaggaca gagggtagtg gactcagtc                                      29

<210> SEQ ID NO 42
<211> LENGTH: 33
<212> TYPE: RNA
<213> ORGANISM: Artificial Sequence
<220> FEATURE:
<223> OTHER INFORMATION: Synthetic

<400> SEQUENCE: 42
gucgaggaca gagccaagug gacucagucu uuu                                 33
```

<210> SEQ ID NO 43
<211> LENGTH: 39
<212> TYPE: RNA
<213> ORGANISM: Artificial Sequence
<220> FEATURE:
<223> OTHER INFORMATION: Synthetic

<400> SEQUENCE: 43
gucgaggaca gagccaagug gacucaguua ugaacuuuu                    39

<210> SEQ ID NO 44
<211> LENGTH: 39
<212> TYPE: RNA
<213> ORGANISM: Artificial Sequence
<220> FEATURE:
<223> OTHER INFORMATION: Synthetic

<400> SEQUENCE: 44
gucgaggaca gaggguagug gacucaguua ugaacuuuu                    39

<210> SEQ ID NO 45
<211> LENGTH: 150
<212> TYPE: RNA
<213> ORGANISM: Mus musculus

<400> SEQUENCE: 45
cuggaggcuu gcugaaggcu guaugcuguu aaugcuaauu gugauagggg uuuuggccuc     60
ugacugacuc cuaccuguua gcauuaacag gacacaaggc cuguuacuag cacucacaug    120
gaacaaaugg ccaccguggg aggaugacaa                                    150

<210> SEQ ID NO 46
<211> LENGTH: 59
<212> TYPE: RNA
<213> ORGANISM: Artificial Sequence
<220> FEATURE:
<223> OTHER INFORMATION: Synthetic

<400> SEQUENCE: 46
uuucuaagca cuuuucugcu gguuuuggcc ucugacugac uagcaacggu gcuuagaaa     59

<210> SEQ ID NO 47
<211> LENGTH: 150
<212> TYPE: DNA
<213> ORGANISM: Artificial Sequence
<220> FEATURE:
<223> OTHER INFORMATION: Synthetic

<400> SEQUENCE: 47
ctggaggctt gctgaaggct gtatgctgtt aatgctaatt gtgatagggg ttttggcctc     60
tgactgactc ctacctgtta gcattaacag gacacaaggc ctgttactag cactcacatg    120
gaacaaatgg ccaccgtggg aggatgacaa                                    150

<210> SEQ ID NO 48
<211> LENGTH: 99
<212> TYPE: DNA
<213> ORGANISM: Artificial Sequence
<220> FEATURE:
<223> OTHER INFORMATION: Synthetic

<400> SEQUENCE: 48
ctggaggctt gctgaaggct gtatgctgtt aatgctaatt gtgatagggg ttttggcctc     60
tgactgactc ctacctgtta gcattaacag gacacaagg                          99

<210> SEQ ID NO 49
<211> LENGTH: 111
<212> TYPE: DNA
<213> ORGANISM: Artificial Sequence
<220> FEATURE:
<223> OTHER INFORMATION: Synthetic

<400> SEQUENCE: 49
ctggaggctt gctgaaggct gtatgctgtt aatgctaatt gtgataggggg ttttggcctc    60 tgactgactc ctacctgtta gcattaacag gacacaaggc ctgttactag c            111

<210> SEQ ID NO 50
<211> LENGTH: 67
<212> TYPE: RNA
<213> ORGANISM: Artificial Sequence
<220> FEATURE:
<223> OTHER INFORMATION: Synthetic

<400> SEQUENCE: 50
gcuguuaaug cuaauuguga uagggguuuu ggccucugac ugacuccuac cguuuagcau    60
uaacagg                                                              67

<210> SEQ ID NO 51
<211> LENGTH: 59
<212> TYPE: DNA
<213> ORGANISM: Artificial Sequence
<220> FEATURE:
<223> OTHER INFORMATION: Synthetic

<400> SEQUENCE: 51
uugcagcaau cuuagcaaaa gguuuuggcc ucugacugac uuuuucugga uugcugcaa     59

<210> SEQ ID NO 52
<211> LENGTH: 59
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(20)
<223> OTHER INFORMATION: n is a, c, g, or u
<220> FEATURE:
<221> NAME/KEY: misc_feature
<222> LOCATION: (42)..(57)
<223> OTHER INFORMATION: n is a, c, g, or u

<400> SEQUENCE: 52
uunnnnnnnn nnnnnnnnnn gguuuuggcc ucugacugac unnnnnnnnn nnnnnnnaa     59

<210> SEQ ID NO 53
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(24)
<223> OTHER INFORMATION: n is a, c, g, or t
<220> FEATURE:
<221> NAME/KEY: misc_feature
<222> LOCATION: (46)..(61)
<223> OTHER INFORMATION: n is a, c, g, or t

<400> SEQUENCE: 53

```
gctgttnnnn nnnnnnnnnn nnnnggtttt ggcctctgac tgactnnnnn nnnnnnnnnn    60 naac                                                                 64
```

<210> SEQ ID NO 54
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(23)
<223> OTHER INFORMATION: n is a, c, g, or t
<220> FEATURE:
<221> NAME/KEY: misc_feature
<222> LOCATION: (45)..(62)
<223> OTHER INFORMATION: n is a, c, g, or t

<400> SEQUENCE: 54

```
tcctgttnnn nnnnnnnnnn nnnagtcagt cagaggccaa aaccnnnnnn nnnnnnnnnn    60 nnaa                                                                 64
```

<210> SEQ ID NO 55
<211> LENGTH: 64
<212> TYPE: DNA
<213> ORGANISM: Artificial Sequence
<220> FEATURE:
<223> OTHER INFORMATION: Synthetic

<400> SEQUENCE: 55

```
gctgttgcag caatcttagc aaaaggtttt ggcctctgac tgactttttc tggattgctg    60
caac                                                                 64
```

<210> SEQ ID NO 56
<211> LENGTH: 64
<212> TYPE: DNA
<213> ORGANISM: Artificial Sequence
<220> FEATURE:
<223> OTHER INFORMATION: Synthetic

<400> SEQUENCE: 56

```
tcctgttgca gcaatccaga aaagtcagt cagaggccaa aacctttgc taagattgct     60 gcaa                                                                 64
```

<210> SEQ ID NO 57
<211> LENGTH: 73
<212> TYPE: DNA
<213> ORGANISM: Artificial Sequence
<220> FEATURE:
<223> OTHER INFORMATION: Synthetic

<400> SEQUENCE: 57

```
ggcttgctga aggctgtatg ctgttgtctt caagatctgg aagacacagg acacaaggcc    60
tgttactagc act                                                       73
```

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58

```
ggcttgctga aggctgtat                                                 19
```

```
<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
ccgaacgact tccgacatac gac                                              23

<210> SEQ ID NO 60
<211> LENGTH: 26
<212> TYPE: DNA
<213> ORGANISM: Artificial Sequence
<220> FEATURE:
<223> OTHER INFORMATION: Synthetic

<400> SEQUENCE: 60
aggacacaag gcctgttact agcact                                           26

<210> SEQ ID NO 61
<211> LENGTH: 21
<212> TYPE: RNA
<213> ORGANISM: Artificial Sequence
<220> FEATURE:
<223> OTHER INFORMATION: Synthetic

<400> SEQUENCE: 61
caugugaucg cgcuucucgu u                                                21

<210> SEQ ID NO 62
<211> LENGTH: 21
<212> TYPE: DNA
<213> ORGANISM: Artificial Sequence
<220> FEATURE:
<223> OTHER INFORMATION: Synthetic

<400> SEQUENCE: 62
ttguacacua gcgcgaagag c                                                21

<210> SEQ ID NO 63
<211> LENGTH: 21
<212> TYPE: RNA
<213> ORGANISM: Artificial Sequence
<220> FEATURE:
<223> OTHER INFORMATION: Synthetic

<400> SEQUENCE: 63
gaagaagucg ugcugcuuca u                                                21

<210> SEQ ID NO 64
<211> LENGTH: 21
<212> TYPE: RNA
<213> ORGANISM: Artificial Sequence
<220> FEATURE:
<223> OTHER INFORMATION: Synthetic

<400> SEQUENCE: 64
uucuucuuca gcacgacgaa g                                                21

<210> SEQ ID NO 65
<211> LENGTH: 21
<212> TYPE: RNA
<213> ORGANISM: Artificial Sequence
<220> FEATURE:
```

<223> OTHER INFORMATION: Synthetic

<400> SEQUENCE: 65
gaccauguga ucgcgcuucu c                                              21

<210> SEQ ID NO 66
<211> LENGTH: 21
<212> TYPE: RNA
<213> ORGANISM: Artificial Sequence
<220> FEATURE:
<223> OTHER INFORMATION: Synthetic

<400> SEQUENCE: 66
uucugguaca cuagcgcgaa g                                              21

<210> SEQ ID NO 67
<211> LENGTH: 21
<212> TYPE: RNA
<213> ORGANISM: Artificial Sequence
<220> FEATURE:
<223> OTHER INFORMATION: Synthetic

<400> SEQUENCE: 67
gaagaagucc agcugcuuca u                                              21

<210> SEQ ID NO 68
<211> LENGTH: 21
<212> TYPE: RNA
<213> ORGANISM: Artificial Sequence
<220> FEATURE:
<223> OTHER INFORMATION: Synthetic

<400> SEQUENCE: 68
uucuucuuca ggucgacgaa g                                              21

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
ggtaatacga ctcactatag                                                20

<210> SEQ ID NO 70
<211> LENGTH: 21
<212> TYPE: RNA
<213> ORGANISM: Artificial Sequence
<220> FEATURE:
<223> OTHER INFORMATION: Synthetic

<400> SEQUENCE: 70
gaagaagucg ugcugcuuca u                                              21

<210> SEQ ID NO 71
<211> LENGTH: 40
<212> TYPE: DNA
<213> ORGANISM: Artificial Sequence
<220> FEATURE:
<223> OTHER INFORMATION: Synthetic

<400> SEQUENCE: 71
atgaagcagc acgacttctt ctatagtgag tcgtattacc                          40

```
<210> SEQ ID NO 72
<211> LENGTH: 43
<212> TYPE: RNA
<213> ORGANISM: Artificial Sequence
<220> FEATURE:
<223> OTHER INFORMATION: Synthetic

<400> SEQUENCE: 72
gaagaagucg ugcugcuuca uggaagcagc acgacuucuu cuu                    43

<210> SEQ ID NO 73
<211> LENGTH: 43
<212> TYPE: RNA
<213> ORGANISM: Artificial Sequence
<220> FEATURE:
<223> OTHER INFORMATION: Synthetic

<400> SEQUENCE: 73
gaagcagcac gacuucuuca aggaagaagu cgugcugcuu cau                    43

<210> SEQ ID NO 74
<211> LENGTH: 43
<212> TYPE: RNA
<213> ORGANISM: Artificial Sequence
<220> FEATURE:
<223> OTHER INFORMATION: Synthetic

<400> SEQUENCE: 74
gaagaagucc agcugcuuca uggaagcagc uggacuucuu cuu                    43

<210> SEQ ID NO 75
<211> LENGTH: 43
<212> TYPE: RNA
<213> ORGANISM: Artificial Sequence
<220> FEATURE:
<223> OTHER INFORMATION: Synthetic

<400> SEQUENCE: 75
gaagaagucg agcugcuuca uggaagcagc acgacuucuu cuu                    43

<210> SEQ ID NO 76
<211> LENGTH: 43
<212> TYPE: RNA
<213> ORGANISM: Artificial Sequence
<220> FEATURE:
<223> OTHER INFORMATION: Synthetic

<400> SEQUENCE: 76
gaagaagucg ugcugcuuca uggaagcagc aggacuucuu cuu                    43

<210> SEQ ID NO 77
<211> LENGTH: 21
<212> TYPE: RNA
<213> ORGANISM: Artificial Sequence
<220> FEATURE:
<223> OTHER INFORMATION: Synthetic

<400> SEQUENCE: 77
gacagagcca aguggacuca c                                            21

<210> SEQ ID NO 78
<211> LENGTH: 21
<212> TYPE: RNA
<213> ORGANISM: Artificial Sequence
<220> FEATURE:
<223> OTHER INFORMATION: Synthetic
```

```
<400> SEQUENCE: 78
uucugucucg guucaccuga g                                          21

<210> SEQ ID NO 79
<211> LENGTH: 43
<212> TYPE: RNA
<213> ORGANISM: Artificial Sequence
<220> FEATURE:
<223> OTHER INFORMATION: Synthetic

<400> SEQUENCE: 79
gacagagcca aguggacuca cagaguccac uuggcucugu cuu                  43

<210> SEQ ID NO 80
<211> LENGTH: 21
<212> TYPE: RNA
<213> ORGANISM: Artificial Sequence
<220> FEATURE:
<223> OTHER INFORMATION: Synthetic

<400> SEQUENCE: 80
gacagagcgu aguggacuca c                                          21

<210> SEQ ID NO 81
<211> LENGTH: 21
<212> TYPE: RNA
<213> ORGANISM: Artificial Sequence
<220> FEATURE:
<223> OTHER INFORMATION: Synthetic

<400> SEQUENCE: 81
uucugucucg caucaccuga g                                          21

<210> SEQ ID NO 82
<211> LENGTH: 43
<212> TYPE: RNA
<213> ORGANISM: Artificial Sequence
<220> FEATURE:
<223> OTHER INFORMATION: Synthetic

<400> SEQUENCE: 82
gacagagcgu aguggacuca cagaguccac uacgcucugu cuu                  43

<210> SEQ ID NO 83
<211> LENGTH: 23
<212> TYPE: RNA
<213> ORGANISM: Artificial Sequence
<220> FEATURE:
<223> OTHER INFORMATION: Synthetic

<400> SEQUENCE: 83
gacagagcca aguggacucu uuu                                        23

<210> SEQ ID NO 84
<211> LENGTH: 34
<212> TYPE: DNA
<213> ORGANISM: Artificial Sequence
<220> FEATURE:
<223> OTHER INFORMATION: Synthetic

<400> SEQUENCE: 84
tgtttgacag agccaagtgg actctttttc taga                            34

<210> SEQ ID NO 85
<211> LENGTH: 34
```

```
<212> TYPE: DNA
<213> ORGANISM: Artificial Sequence
<220> FEATURE:
<223> OTHER INFORMATION: Synthetic

<400> SEQUENCE: 85
acaaactgtc tcggttcacc tgagaaaaag atct                              34

<210> SEQ ID NO 86
<211> LENGTH: 23
<212> TYPE: RNA
<213> ORGANISM: Artificial Sequence
<220> FEATURE:
<223> OTHER INFORMATION: Synthetic

<400> SEQUENCE: 86
gacagagcca aguggacucu uuu                                          23

<210> SEQ ID NO 87
<211> LENGTH: 23
<212> TYPE: RNA
<213> ORGANISM: Artificial Sequence
<220> FEATURE:
<223> OTHER INFORMATION: Synthetic

<400> SEQUENCE: 87
gaguccacuu ggcucugucu uuu                                          23

<210> SEQ ID NO 88
<211> LENGTH: 23
<212> TYPE: RNA
<213> ORGANISM: Artificial Sequence
<220> FEATURE:
<223> OTHER INFORMATION: Synthetic

<400> SEQUENCE: 88
gacagagcgu aguggacucu uuu                                          23

<210> SEQ ID NO 89
<211> LENGTH: 23
<212> TYPE: RNA
<213> ORGANISM: Artificial Sequence
<220> FEATURE:
<223> OTHER INFORMATION: Synthetic

<400> SEQUENCE: 89
gaguccacua cgcucugucu uuu                                          23

<210> SEQ ID NO 90
<211> LENGTH: 23
<212> TYPE: RNA
<213> ORGANISM: Artificial Sequence
<220> FEATURE:
<223> OTHER INFORMATION: Synthetic

<400> SEQUENCE: 90
ggacuuuaac cugggagccu uuu                                          23

<210> SEQ ID NO 91
<211> LENGTH: 23
<212> TYPE: RNA
<213> ORGANISM: Artificial Sequence
<220> FEATURE:
<223> OTHER INFORMATION: Synthetic

<400> SEQUENCE: 91
```

-continued

| | |
|---|---|
| ggcucccagg uuaaaguccu uuu | 23 |

<210> SEQ ID NO 92
<211> LENGTH: 45
<212> TYPE: RNA
<213> ORGANISM: Artificial Sequence
<220> FEATURE:
<223> OTHER INFORMATION: Synthetic

<400> SEQUENCE: 92

| | |
|---|---|
| gacagagcca aguggacuca cagaguccac uuggcucugu cuuuu | 45 |

<210> SEQ ID NO 93
<211> LENGTH: 45
<212> TYPE: RNA
<213> ORGANISM: Artificial Sequence
<220> FEATURE:
<223> OTHER INFORMATION: Synthetic

<400> SEQUENCE: 93

| | |
|---|---|
| gacagagcca aguggacuca cagaguccac uucgcucugu cuuuu | 45 |

<210> SEQ ID NO 94
<211> LENGTH: 45
<212> TYPE: RNA
<213> ORGANISM: Artificial Sequence
<220> FEATURE:
<223> OTHER INFORMATION: Synthetic

<400> SEQUENCE: 94

| | |
|---|---|
| gacagagcgu aguggacuca cagaguccac uaggcucugu cuuuu | 45 |

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95

| | |
|---|---|
| ggtaatacga ctcactatag | 20 |

<210> SEQ ID NO 96
<211> LENGTH: 40
<212> TYPE: DNA
<213> ORGANISM: Artificial Sequence
<220> FEATURE:
<223> OTHER INFORMATION: Synthetic

<400> SEQUENCE: 96

| | |
|---|---|
| aagaagaagt cgtgctgctt ctatagtgag tcgtattacc | 40 |

<210> SEQ ID NO 97
<211> LENGTH: 40
<212> TYPE: DNA
<213> ORGANISM: Artificial Sequence
<220> FEATURE:
<223> OTHER INFORMATION: Synthetic

<400> SEQUENCE: 97

| | |
|---|---|
| atgaagcagc acgacttctt ctatagtgag tcgtattacc | 40 |

<210> SEQ ID NO 98
<211> LENGTH: 40
<212> TYPE: DNA
<213> ORGANISM: Artificial Sequence

```
<220> FEATURE:
<223> OTHER INFORMATION: Synthetic

<400> SEQUENCE: 98
aagaagaagt ccagctgctt ctatagtgag tcgtattacc                    40

<210> SEQ ID NO 99
<211> LENGTH: 40
<212> TYPE: DNA
<213> ORGANISM: Artificial Sequence
<220> FEATURE:
<223> OTHER INFORMATION: Synthetic

<400> SEQUENCE: 99
atgaagcagc tggacttctt ctatagtgag tcgtattacc                    40

<210> SEQ ID NO 100
<211> LENGTH: 40
<212> TYPE: DNA
<213> ORGANISM: Artificial Sequence
<220> FEATURE:
<223> OTHER INFORMATION: Synthetic

<400> SEQUENCE: 100
aagaccatgt gatcgcgctt ctatagtgag tcgtattacc                    40

<210> SEQ ID NO 101
<211> LENGTH: 40
<212> TYPE: DNA
<213> ORGANISM: Artificial Sequence
<220> FEATURE:
<223> OTHER INFORMATION: Synthetic

<400> SEQUENCE: 101
gagaagcgcg atcacatggt ctatagtgag tcgtattacc                    40

<210> SEQ ID NO 102
<211> LENGTH: 60
<212> TYPE: DNA
<213> ORGANISM: Artificial Sequence
<220> FEATURE:
<223> OTHER INFORMATION: Synthetic

<400> SEQUENCE: 102
aagaagaagt cgtgctgctt ccatgaagca gcacgacttc ttctatagtg agtcgtatta    60

<210> SEQ ID NO 103
<211> LENGTH: 60
<212> TYPE: DNA
<213> ORGANISM: Artificial Sequence
<220> FEATURE:
<223> OTHER INFORMATION: Synthetic

<400> SEQUENCE: 103
atgaagcagc acgacttctt ccttgaagaa gtcgtgctgc ttctatagtg agtcgtatta    60

<210> SEQ ID NO 104
<211> LENGTH: 60
<212> TYPE: DNA
<213> ORGANISM: Artificial Sequence
<220> FEATURE:
<223> OTHER INFORMATION: Synthetic

<400> SEQUENCE: 104
aagaagaagt ccagctgctt ccatgaagca gctggacttc ttctatagtg agtcgtatta    60
```

```
<210> SEQ ID NO 105
<211> LENGTH: 60
<212> TYPE: DNA
<213> ORGANISM: Artificial Sequence
<220> FEATURE:
<223> OTHER INFORMATION: Synthetic

<400> SEQUENCE: 105
aagaagaagt cgtgctgctt ccatgaagca gctcgacttc ttctatagtg agtcgtatta    60

<210> SEQ ID NO 106
<211> LENGTH: 60
<212> TYPE: DNA
<213> ORGANISM: Artificial Sequence
<220> FEATURE:
<223> OTHER INFORMATION: Synthetic

<400> SEQUENCE: 106
aagaagaagt cctgctgctt ccatgaagca gcacgacttc ttctatagtg agtcgtatta    60

<210> SEQ ID NO 107
<211> LENGTH: 40
<212> TYPE: DNA
<213> ORGANISM: Artificial Sequence
<220> FEATURE:
<223> OTHER INFORMATION: Synthetic

<400> SEQUENCE: 107
aagacagagc caagtggact ctatagtgag tcgtattacc                          40

<210> SEQ ID NO 108
<211> LENGTH: 40
<212> TYPE: DNA
<213> ORGANISM: Artificial Sequence
<220> FEATURE:
<223> OTHER INFORMATION: Synthetic

<400> SEQUENCE: 108
gtgagtccac ttggctctgt ctatagtgag tcgtattacc                          40

<210> SEQ ID NO 109
<211> LENGTH: 40
<212> TYPE: DNA
<213> ORGANISM: Artificial Sequence
<220> FEATURE:
<223> OTHER INFORMATION: Synthetic

<400> SEQUENCE: 109
aagacagagc gtagtggact ctatagtgag tcgtattacc                          40

<210> SEQ ID NO 110
<211> LENGTH: 40
<212> TYPE: DNA
<213> ORGANISM: Artificial Sequence
<220> FEATURE:
<223> OTHER INFORMATION: Synthetic

<400> SEQUENCE: 110
gtgagtccac tacgctctgt ctatagtgag tcgtattacc                          40

<210> SEQ ID NO 111
<211> LENGTH: 62
<212> TYPE: DNA
<213> ORGANISM: Artificial Sequence
<220> FEATURE:
<223> OTHER INFORMATION: Synthetic
```

<400> SEQUENCE: 111
aagacagagc caagtggact ctgtgagtcc acttggctct gtctatagtg agtcgtatta    60
cc    62

<210> SEQ ID NO 112
<211> LENGTH: 62
<212> TYPE: DNA
<213> ORGANISM: Artificial Sequence
<220> FEATURE:
<223> OTHER INFORMATION: Synthetic

<400> SEQUENCE: 112
aagacagagc gtagtggact ctgtgagtcc actacgctct gtctatagtg agtcgtatta    60
cc    62

<210> SEQ ID NO 113
<211> LENGTH: 27
<212> TYPE: DNA
<213> ORGANISM: Artificial Sequence
<220> FEATURE:
<223> OTHER INFORMATION: Synthetic

<400> SEQUENCE: 113
tttgagtcca cttggctctg tctttt    27

<210> SEQ ID NO 114
<211> LENGTH: 27
<212> TYPE: DNA
<213> ORGANISM: Artificial Sequence
<220> FEATURE:
<223> OTHER INFORMATION: Synthetic

<400> SEQUENCE: 114
tcaggtgaac cgagacagaa aaagatc    27

<210> SEQ ID NO 115
<211> LENGTH: 27
<212> TYPE: DNA
<213> ORGANISM: Artificial Sequence
<220> FEATURE:
<223> OTHER INFORMATION: Synthetic

<400> SEQUENCE: 115
tttgacagag ccaagtggac tctttt    27

<210> SEQ ID NO 116
<211> LENGTH: 27
<212> TYPE: DNA
<213> ORGANISM: Artificial Sequence
<220> FEATURE:
<223> OTHER INFORMATION: Synthetic

<400> SEQUENCE: 116
tgtctcggtt cacctgagaa aaagatc    27

<210> SEQ ID NO 117
<211> LENGTH: 27
<212> TYPE: DNA
<213> ORGANISM: Artificial Sequence
<220> FEATURE:
<223> OTHER INFORMATION: Synthetic

<400> SEQUENCE: 117

```
tttgagtcca cttccctctg tctttttt                                27
```

<210> SEQ ID NO 118
<211> LENGTH: 27
<212> TYPE: DNA
<213> ORGANISM: Artificial Sequence
<220> FEATURE:
<223> OTHER INFORMATION: Synthetic

<400> SEQUENCE: 118

```
tcaggtgaag ggagacagaa aaagatc                                 27
```

<210> SEQ ID NO 119
<211> LENGTH: 27
<212> TYPE: DNA
<213> ORGANISM: Artificial Sequence
<220> FEATURE:
<223> OTHER INFORMATION: Synthetic

<400> SEQUENCE: 119

```
tttgacagag ggaagtggac tcttttt                                 27
```

<210> SEQ ID NO 120
<211> LENGTH: 27
<212> TYPE: DNA
<213> ORGANISM: Artificial Sequence
<220> FEATURE:
<223> OTHER INFORMATION: Synthetic

<400> SEQUENCE: 120

```
tgtctccctt cacctgagaa aaagatc                                 27
```

<210> SEQ ID NO 121
<211> LENGTH: 27
<212> TYPE: DNA
<213> ORGANISM: Artificial Sequence
<220> FEATURE:
<223> OTHER INFORMATION: Synthetic

<400> SEQUENCE: 121

```
tttggacttt aacctgggag cctttttt                                27
```

<210> SEQ ID NO 122
<211> LENGTH: 27
<212> TYPE: DNA
<213> ORGANISM: Artificial Sequence
<220> FEATURE:
<223> OTHER INFORMATION: Synthetic

<400> SEQUENCE: 122

```
ctgaaattgg accctcggaa aaagatc                                 27
```

<210> SEQ ID NO 123
<211> LENGTH: 27
<212> TYPE: DNA
<213> ORGANISM: Artificial Sequence
<220> FEATURE:
<223> OTHER INFORMATION: Synthetic

<400> SEQUENCE: 123

```
tttggctccc aggttaaagt cctttttt                                27
```

<210> SEQ ID NO 124
<211> LENGTH: 27
<212> TYPE: DNA
<213> ORGANISM: Artificial Sequence

```
<220> FEATURE:
<223> OTHER INFORMATION: Synthetic

<400> SEQUENCE: 124
cgagggtcca atttcaggaa aaagatc                                       27

<210> SEQ ID NO 125
<211> LENGTH: 49
<212> TYPE: DNA
<213> ORGANISM: Artificial Sequence
<220> FEATURE:
<223> OTHER INFORMATION: Synthetic

<400> SEQUENCE: 125
tttgacagag ccaagtggac tcacagagtc cacttggctc tgtctttt               49

<210> SEQ ID NO 126
<211> LENGTH: 49
<212> TYPE: DNA
<213> ORGANISM: Artificial Sequence
<220> FEATURE:
<223> OTHER INFORMATION: Synthetic

<400> SEQUENCE: 126
tgtctcggtt cacctgagtg tctcaggtga accgagacag aaaaagatc               49

<210> SEQ ID NO 127
<211> LENGTH: 49
<212> TYPE: DNA
<213> ORGANISM: Artificial Sequence
<220> FEATURE:
<223> OTHER INFORMATION: Synthetic

<400> SEQUENCE: 127
tttgacagag ccaagtggac tcacagagtc cacttcgctc tgtctttt               49

<210> SEQ ID NO 128
<211> LENGTH: 49
<212> TYPE: DNA
<213> ORGANISM: Artificial Sequence
<220> FEATURE:
<223> OTHER INFORMATION: Synthetic

<400> SEQUENCE: 128
tgtctcggtt cacctgagtg tctcaggtga agcgagacag aaaaagatc               49

<210> SEQ ID NO 129
<211> LENGTH: 49
<212> TYPE: DNA
<213> ORGANISM: Artificial Sequence
<220> FEATURE:
<223> OTHER INFORMATION: Synthetic

<400> SEQUENCE: 129
tttgacagag cgtagtggac tcacagagtc cactaggctc tgtctttt               49

<210> SEQ ID NO 130
<211> LENGTH: 49
<212> TYPE: DNA
<213> ORGANISM: Artificial Sequence
<220> FEATURE:
<223> OTHER INFORMATION: Synthetic

<400> SEQUENCE: 130
tgtctcgcat cacctgagtg tctcaggtga tccgagacag aaaaagatc               49
```

```
<210> SEQ ID NO 131
<211> LENGTH: 45
<212> TYPE: RNA
<213> ORGANISM: Artificial Sequence
<220> FEATURE:
<223> OTHER INFORMATION: Synthetic

<400> SEQUENCE: 131
gaagaagucg ugcugcuuca uggaagcagc aggacuucuu cuuuu            45

<210> SEQ ID NO 132
<211> LENGTH: 58
<212> TYPE: RNA
<213> ORGANISM: Artificial Sequence
<220> FEATURE:
<223> OTHER INFORMATION: Synthetic

<400> SEQUENCE: 132
gaagaagucg ugcugcuucu gugcaggucc caauggaagc agcaggacuu cucuuuu   58

<210> SEQ ID NO 133
<211> LENGTH: 45
<212> TYPE: RNA
<213> ORGANISM: Artificial Sequence
<220> FEATURE:
<223> OTHER INFORMATION: Synthetic

<400> SEQUENCE: 133
gaagaagucg ugcugcuuca cagaagcagc aggacuucuu cuuuu            45

<210> SEQ ID NO 134
<211> LENGTH: 51
<212> TYPE: RNA
<213> ORGANISM: Artificial Sequence
<220> FEATURE:
<223> OTHER INFORMATION: Synthetic

<400> SEQUENCE: 134
gaagaagucg ugcugcuucu ucaagagaga agcagcagga cuucuucuuu u     51

<210> SEQ ID NO 135
<211> LENGTH: 45
<212> TYPE: RNA
<213> ORGANISM: Artificial Sequence
<220> FEATURE:
<223> OTHER INFORMATION: Synthetic

<400> SEQUENCE: 135
gaagaagucg ugcugcuuca uugaagcagc aggacuucuu cuuuu            45

<210> SEQ ID NO 136
<211> LENGTH: 45
<212> TYPE: RNA
<213> ORGANISM: Artificial Sequence
<220> FEATURE:
<223> OTHER INFORMATION: Synthetic

<400> SEQUENCE: 136
gaagcagcag gacuucuuca uugaagaagu cgugcugcuu cuuuu            45

<210> SEQ ID NO 137
<211> LENGTH: 57
<212> TYPE: RNA
<213> ORGANISM: Artificial Sequence
<220> FEATURE:
<223> OTHER INFORMATION: Synthetic
```

```
<400> SEQUENCE: 137
gaagaagucg ugcugcuuca gucaauauaa cuuugaagca gcaggacuuc uucuuuu      57

<210> SEQ ID NO 138
<211> LENGTH: 51
<212> TYPE: RNA
<213> ORGANISM: Artificial Sequence
<220> FEATURE:
<223> OTHER INFORMATION: Synthetic

<400> SEQUENCE: 138
gaagcagcag gacuucuucu ucaagagaga agaagucgug cugcuucuuu u            51

<210> SEQ ID NO 139
<211> LENGTH: 45
<212> TYPE: RNA
<213> ORGANISM: Artificial Sequence
<220> FEATURE:
<223> OTHER INFORMATION: Synthetic

<400> SEQUENCE: 139
gaagaagucg ugcugcuuca uggaagcagc aggacuucuu cuuuu                   45

<210> SEQ ID NO 140
<211> LENGTH: 45
<212> TYPE: RNA
<213> ORGANISM: Artificial Sequence
<220> FEATURE:
<223> OTHER INFORMATION: Synthetic

<400> SEQUENCE: 140
ggaaggugcg cucaaugacu gugucauuga gggcaccuuc cuuuu                   45

<210> SEQ ID NO 141
<211> LENGTH: 63
<212> TYPE: RNA
<213> ORGANISM: Artificial Sequence
<220> FEATURE:
<223> OTHER INFORMATION: Synthetic

<400> SEQUENCE: 141
gacuugaaga agucgugcug cuucaugugg gacaugaagc agcaucacuu cuucaagucu   60
uuu                                                                63

<210> SEQ ID NO 142
<211> LENGTH: 63
<212> TYPE: RNA
<213> ORGANISM: Artificial Sequence
<220> FEATURE:
<223> OTHER INFORMATION: Synthetic

<400> SEQUENCE: 142
ggaaggugcg cucaaugacu gugguccacu guggaccaca gucauucggc gcaccuuccu   60
uuu                                                                63

<210> SEQ ID NO 143
<211> LENGTH: 62
<212> TYPE: RNA
<213> ORGANISM: Artificial Sequence
<220> FEATURE:
<223> OTHER INFORMATION: Synthetic

<400> SEQUENCE: 143
```

-continued

```
gacuugaaga agucgugcug cucaugugg acaugaagca gcaucacuuc uucaagucuu    60
uu                                                                  62

<210> SEQ ID NO 144
<211> LENGTH: 64
<212> TYPE: RNA
<213> ORGANISM: Artificial Sequence
<220> FEATURE:
<223> OTHER INFORMATION: Synthetic

<400> SEQUENCE: 144
ggaaggugcg cucaaugacu gugguccacu guggaccaac agucauucgg cgcaccuucc    60
uuuu                                                                64

<210> SEQ ID NO 145
<211> LENGTH: 45
<212> TYPE: RNA
<213> ORGANISM: Artificial Sequence
<220> FEATURE:
<223> OTHER INFORMATION: Synthetic

<400> SEQUENCE: 145
guggauguag gccaagcucc gggagcuugg ccuacaucca cuuuu                    45

<210> SEQ ID NO 146
<211> LENGTH: 45
<212> TYPE: RNA
<213> ORGANISM: Artificial Sequence
<220> FEATURE:
<223> OTHER INFORMATION: Synthetic

<400> SEQUENCE: 146
gaucuggagc ucucgguucu uagaaccgag agcuccagau cuuuu                    45

<210> SEQ ID NO 147
<211> LENGTH: 47
<212> TYPE: RNA
<213> ORGANISM: Artificial Sequence
<220> FEATURE:
<223> OTHER INFORMATION: Synthetic

<400> SEQUENCE: 147
gaugguugga uggacaguuc acugaacugu ccauccaacc aucuuuu                  47

<210> SEQ ID NO 148
<211> LENGTH: 45
<212> TYPE: RNA
<213> ORGANISM: Artificial Sequence
<220> FEATURE:
<223> OTHER INFORMATION: Synthetic

<400> SEQUENCE: 148
guguugcuga guggcacuca aggagugcca gucagcaaca cuuuu                    45

<210> SEQ ID NO 149
<211> LENGTH: 45
<212> TYPE: RNA
<213> ORGANISM: Artificial Sequence
<220> FEATURE:
<223> OTHER INFORMATION: Synthetic

<400> SEQUENCE: 149
guaguaccga gagcagaugu aucaucugcu gucgguacua cuuuu                    45
```

```
<210> SEQ ID NO 150
<211> LENGTH: 24
<212> TYPE: RNA
<213> ORGANISM: Artificial Sequence
<220> FEATURE:
<223> OTHER INFORMATION: Synthetic

<400> SEQUENCE: 150
ccuacaucug cucucgguac uacc                                              24

<210> SEQ ID NO 151
<211> LENGTH: 22
<212> TYPE: RNA
<213> ORGANISM: Artificial Sequence
<220> FEATURE:
<223> OTHER INFORMATION: Synthetic

<400> SEQUENCE: 151
guaguaccga gagcagaugu au                                                22

<210> SEQ ID NO 152
<211> LENGTH: 24
<212> TYPE: RNA
<213> ORGANISM: Artificial Sequence
<220> FEATURE:
<223> OTHER INFORMATION: Synthetic

<400> SEQUENCE: 152
cauauaucug uucucgguac uaca                                              24

<210> SEQ ID NO 153
<211> LENGTH: 29
<212> TYPE: DNA
<213> ORGANISM: Artificial Sequence
<220> FEATURE:
<223> OTHER INFORMATION: Synthetic

<400> SEQUENCE: 153
gggatccgtg gtttaagttg catatccct                                         29

<210> SEQ ID NO 154
<211> LENGTH: 30
<212> TYPE: DNA
<213> ORGANISM: Artificial Sequence
<220> FEATURE:
<223> OTHER INFORMATION: Synthetic

<400> SEQUENCE: 154
ggtctagagt gcattcattt tgtattctgg                                        30

<210> SEQ ID NO 155
<211> LENGTH: 59
<212> TYPE: RNA
<213> ORGANISM: Artificial Sequence
<220> FEATURE:
<223> OTHER INFORMATION: Synthetic

<400> SEQUENCE: 155
uuaaugcuaa uugugauagg gguuuuggcc ucugacugac uccaccugu uagcauuaa         59

<210> SEQ ID NO 156
<211> LENGTH: 73
<212> TYPE: DNA
<213> ORGANISM: Artificial Sequence
<220> FEATURE:
<223> OTHER INFORMATION: Synthetic
```

```
<400> SEQUENCE: 156
ggcttgctga aggctgtatg ctgttgtctt caagatctgg aagacacagg acacaaggcc      60
tgttactagc act                                                          73

<210> SEQ ID NO 157
<211> LENGTH: 19
<212> TYPE: DNA
<213> ORGANISM: Artificial Sequence
<220> FEATURE:
<223> OTHER INFORMATION: Synthetic

<400> SEQUENCE: 157
ggcttgctga aggctgtat                                                    19

<210> SEQ ID NO 158
<211> LENGTH: 23
<212> TYPE: DNA
<213> ORGANISM: Artificial Sequence
<220> FEATURE:
<223> OTHER INFORMATION: Synthetic

<400> SEQUENCE: 158
ccgaacgact tccgacatac gac                                               23

<210> SEQ ID NO 159
<211> LENGTH: 15
<212> TYPE: DNA
<213> ORGANISM: Artificial Sequence
<220> FEATURE:
<223> OTHER INFORMATION: Synthetic

<400> SEQUENCE: 159
aggacacaag gcctg                                                        15

<210> SEQ ID NO 160
<211> LENGTH: 11
<212> TYPE: DNA
<213> ORGANISM: Artificial Sequence
<220> FEATURE:
<223> OTHER INFORMATION: Synthetic

<400> SEQUENCE: 160
gtgttccgga c                                                            11

<210> SEQ ID NO 161
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(25)
<223> OTHER INFORMATION: n is a, c, g, or t

<400> SEQUENCE: 161
gctgnnnnnn nnnnnnnnnn nnnnnc                                            26

<210> SEQ ID NO 162
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(21)
<223> OTHER INFORMATION: n is a, c, g, or t

<400> SEQUENCE: 162
nnnnnnnnnn nnnnnnnnnn ngtcct                                          26

<210> SEQ ID NO 163
<211> LENGTH: 59
<212> TYPE: RNA
<213> ORGANISM: Artificial Sequence
<220> FEATURE:
<223> OTHER INFORMATION: Synthetic

<400> SEQUENCE: 163
uuaaugcuaa uugugauagg gguuuuggcc ucugacugac uccuaccugu uagcauuaa       59

<210> SEQ ID NO 164
<211> LENGTH: 59
<212> TYPE: RNA
<213> ORGANISM: Artificial Sequence
<220> FEATURE:
<223> OTHER INFORMATION: Synthetic

<400> SEQUENCE: 164
uugcagcaau cuuagcaaaa gguuuuggcc ucugacugac uuuuucugga uugcugcaa       59

<210> SEQ ID NO 165
<211> LENGTH: 64
<212> TYPE: DNA
<213> ORGANISM: Artificial Sequence
<220> FEATURE:
<223> OTHER INFORMATION: Synthetic

<400> SEQUENCE: 165
gctgttgcag caatcttagc aaaaggtttt ggcctctgac tgacttttc tggattgctg       60 caac                                                                  64

<210> SEQ ID NO 166
<211> LENGTH: 64
<212> TYPE: DNA
<213> ORGANISM: Artificial Sequence
<220> FEATURE:
<223> OTHER INFORMATION: Synthetic

<400> SEQUENCE: 166
aacgtcgtta gaatcgtttt ccaaaaccgg agactgactg aaaaagacct aacgacgttg      60
tcct                                                                  64

<210> SEQ ID NO 167
<211> LENGTH: 61
<212> TYPE: RNA
<213> ORGANISM: Artificial Sequence
<220> FEATURE:
<223> OTHER INFORMATION: Synthetic

<400> SEQUENCE: 167
uugcagcaau cuuagcaaaa gguuuuggcc ucugacugac cuuuugcugg gauugcugca      60
a                                                                     61

<210> SEQ ID NO 168
<211> LENGTH: 457
<212> TYPE: DNA
<213> ORGANISM: Artificial Sequence
<220> FEATURE:
```

<223> OTHER INFORMATION: Synthetic

<400> SEQUENCE: 168

```
gtggtttaag ttgcatatcc cttatcctct ggctgctgga ggcttgctga aggctgtatg     60
ctgttaatgc taattgtgat aggggttttg gcctctgact gactcctacc tgttagcatt    120
aacaggacac aaggcctgtt actagcactc acatggaaca aatggccacc gtgggaggat    180
gacaagtcca agagtcaccc tgctggatga acgtagatgt cagactctat catttaatgt    240
gctagtcata acctggttac taggatagtc cactgtaagt gttacgataa atgtcattta    300
aaagatagat cagcagtatc ctaaacaaca tctcaacttc aagcccacat gtttattttt    360
tatcttgaat ggaaagtgaa acttgtatca tttttatttc aaaattatgt tcataaccat    420
cttcaatgat tcaaccagaa tacaaaatga atgcact                             457
```

<210> SEQ ID NO 169
<211> LENGTH: 421
<212> TYPE: DNA
<213> ORGANISM: Artificial Sequence
<220> FEATURE:
<223> OTHER INFORMATION: Synthetic

<400> SEQUENCE: 169

```
gtggtttaag ttgcatatcc cttatcctct ggctgctgga ggcttgctga aggctgtatg     60
ctgttgtctt caagatctgg aagacacagg acacaaggcc tgttactagc actcacatgg    120
aacaaatggc caccgtggga ggatgacaag tccaagagtc accctgctgg atgaacgtag    180
atgtcagact ctatcattta atgtgctagt cataacctgg ttactaggat agtccactgt    240
aagtgttacg ataaatgtca tttaaaagat agatcagcag tatcctaaac aacatctcaa    300
cttcaagccc acatgtttat ttttatcttg aatggaaagt gaaacttgt atcatttta    360
tttcaaaatt atgttcataa ccatcttcaa tgattcaacc agaatacaaa atgaatgcac    420
t                                                                    421
```

<210> SEQ ID NO 170
<211> LENGTH: 22
<212> TYPE: DNA
<213> ORGANISM: Artificial Sequence
<220> FEATURE:
<223> OTHER INFORMATION: Synthetic

<400> SEQUENCE: 170

```
gtgttccgga caatgatcgt ga                                              22
```

<210> SEQ ID NO 171
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(26)
<223> OTHER INFORMATION: n is a, c, g, or t

<400> SEQUENCE: 171

```
gctgnnnnnn nnnnnnnnnn nnnnnnc                                         27
```

<210> SEQ ID NO 172
<211> LENGTH: 27
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(22)
<223> OTHER INFORMATION: n is a, c, g, or t

<400> SEQUENCE: 172
nnnnnnnnnn nnnnnnnnnn nngtcct                                       27
```

We claim:

1. A composition comprising a vector, said vector comprising a sequence encoding at least a portion of a BIC miRNA precursor molecule operably linked to a promoter, wherein said portion comprises at least nucleotides 1-111 of SEQ ID NO:47, and wherein said promoter permits expression of said miRNA in a cell.

2. The composition of claim 1, wherein said portion comprises SEQ ID NO: 49.

3. The composition of claim 1, wherein said miRNA is produced from said DNA molecule as a hairpin RNA.

4. The composition of claim 1, wherein said miRNA includes at least a portion of a miR155 miRNA.

5. A composition comprising a vector, said vector comprising a sequence encoding at least a portion of a BIC miRNA precursor molecule operably linked to a promoter, wherein said portion comprises SEQ ID NO:47, wherein approximately bases 29-50 or 68-87 of SEQ ID NO:47 are replaced with sequences complementary to a target mRNA, and wherein said bases 29-50 are at least partially complementary to said bases 68-87.

6. The composition of claim 5, wherein said miRNA is produced from said DNA molecule as a hairpin RNA.

7. The composition of claim 5, wherein said miRNA includes at least a portion of a miR155 miRNA.

8. A method for inhibiting the function of a target RNA molecule, comprising transfecting a cell with a DNA molecule comprising a sequence encoding at least a portion of a BIC miRNA precursor molecule operably linked to a promoter, wherein said portion comprises at least nucleotides 1-111 of SEQ ID NO:47, and wherein the promoter can be expressed in the cell, wherein said BIC miRNA encodes an miRNA complementary to a portion of said target RNA molecule.

9. The method of claim 8, wherein said portion comprises SEQ ID NO: 49.

10. The method of claim 8, wherein said miRNA is produced from said DNA molecule as a hairpin RNA.

11. The method of claim 8, wherein said miRNA includes at least a portion of a miR155 miRNA.

12. The method of claim 8, wherein said cell is in an organism.

13. A method for inhibiting the function of a target RNA molecule, comprising transfecting a cell with a DNA molecule comprising a sequence encoding at least a portion of a BIC miRNA precursor molecule operably linked to a promoter, wherein said portion comprises SEQ ID NO:47, wherein approximately bases 29-50 or 68-87 of SEQ ID NO:47 are replaced with sequences complementary to said target mRNA, and wherein said bases 29-50 are at least partially complementary to said bases 68-87.

14. The method of claim 13, wherein said miRNA is produced from said DNA molecule as a hairpin RNA.

15. The method of claim 13, wherein said miRNA includes at least a portion of a miR155 miRNA.

16. The method of claim 13, wherein said cell is in an organism.

* * * * *